US009050368B2

(12) United States Patent
Phillips et al.

(10) Patent No.: US 9,050,368 B2
(45) Date of Patent: Jun. 9, 2015

(54) CORTICOSTEROID COMPOSITIONS

(75) Inventors: Elaine Phillips, San Diego, CA (US); Malcolm Hill, Solana Beach, CA (US); Hemant Deshmukh, San Diego, CA (US); Keith Johnson, Durham, NC (US); Cynthia Licalsi, San Diego, CA (US)

(73) Assignee: Meritage Pharma, Inc., San Diego, CA (US)

( * ) Notice: Subject to any disclaimer, the term of this patent is extended or adjusted under 35 U.S.C. 154(b) by 262 days.

(21) Appl. No.: 12/269,816

(22) Filed: Nov. 12, 2008

(65) Prior Publication Data

US 2009/0123550 A1   May 14, 2009

Related U.S. Application Data

(60) Provisional application No. 61/035,348, filed on Mar. 10, 2008, provisional application No. 61/054,103, filed on May 16, 2008, provisional application No. 61/054,105, filed on May 16, 2008, provisional application No. 61/012,012, filed on Dec. 6, 2007, provisional application No. 61/054,107, filed on May 16, 2008, provisional application No. 61/015,998, filed on Dec. 21, 2007, provisional application No. 61/019,818, filed on Jan. 8, 2008, provisional application No. 61/034,941, filed on Mar. 7, 2008, provisional application No. 61/054,106, filed on May 16, 2008, provisional application No. 61/090,568, filed on Aug. 20, 2008, provisional application No. 61/987,720, filed on Nov. 13, 2007, provisional application No. 61/054,104, filed on May 16, 2008.

(51) Int. Cl.
| | |
|---|---|
| *A61K 9/14* | (2006.01) |
| *A01N 45/00* | (2006.01) |
| *A61K 31/56* | (2006.01) |
| *A61K 47/38* | (2006.01) |
| *A61K 9/00* | (2006.01) |
| *A61K 31/58* | (2006.01) |
| *A61K 31/575* | (2006.01) |
| *A61K 45/06* | (2006.01) |
| *A61K 47/32* | (2006.01) |
| *A61K 47/36* | (2006.01) |

(52) U.S. Cl.
CPC .............. *A61K 47/38* (2013.01); *A61K 9/006* (2013.01); *A61K 9/0065* (2013.01); *A61K 31/58* (2013.01); *A61K 9/0053* (2013.01); *A61K 31/575* (2013.01); *A61K 45/06* (2013.01); *A61K 47/32* (2013.01); *A61K 47/36* (2013.01)

(58) Field of Classification Search
CPC ...... A61K 31/58; A61K 9/006; A61K 9/0065
USPC .......................................... 424/489; 514/171
See application file for complete search history.

(56) References Cited

U.S. PATENT DOCUMENTS

| | | | |
|---|---|---|---|
| 2,861,920 A | 11/1958 | Dale et al. | |
| 4,684,534 A | 8/1987 | Valentine | |
| 4,880,796 A * | 11/1989 | Yamahira et al. | 514/206 |
| 4,900,552 A | 2/1990 | Sanvordeker et al. | |
| 4,985,418 A | 1/1991 | Richards | |
| 5,254,594 A * | 10/1993 | Niikura et al. | 514/648 |
| 5,288,497 A | 2/1994 | Stanley et al. | |
| 5,380,535 A | 1/1995 | Geyer et al. | |
| 5,446,070 A | 8/1995 | Mantelle | |
| 5,585,108 A | 12/1996 | Ruddy | |
| 5,607,662 A | 3/1997 | Baskeyfield et al. | |
| 5,643,602 A | 7/1997 | Ulmius | |
| 5,679,390 A * | 10/1997 | Conover | 426/96 |
| 5,711,936 A | 1/1998 | Hill et al. | |
| 5,763,910 A | 6/1998 | Ema | |
| 5,814,330 A | 9/1998 | Putteman et al. | |
| 5,837,713 A | 11/1998 | Gleich | |
| 5,840,332 A | 11/1998 | Lerner et al. | |
| 5,855,913 A | 1/1999 | Hanes et al. | |
| 5,863,910 A | 1/1999 | Bolonick et al. | |
| 5,889,028 A | 3/1999 | Sandborn et al. | |
| 5,985,309 A | 11/1999 | Edwards et al. | |
| 6,028,095 A | 2/2000 | Guglietta | |
| 6,248,363 B1 * | 6/2001 | Patel et al. | 424/497 |
| 6,291,445 B1 * | 9/2001 | Nilsson et al. | 514/174 |
| 6,306,789 B1 | 10/2001 | Dettmar et al. | |
| 6,348,502 B1 | 2/2002 | Gardiner et al. | |
| 6,387,383 B1 | 5/2002 | Dow et al. | |
| 6,495,167 B2 * | 12/2002 | Yang | 424/491 |
| 6,509,028 B2 | 1/2003 | Williams et al. | |

(Continued)

FOREIGN PATENT DOCUMENTS

| | | |
|---|---|---|
| EP | 1201242 A2 | 5/2002 |
| EP | 1201242 A3 | 5/2002 |

(Continued)

OTHER PUBLICATIONS

Aceves et. al. (J. Allergy Clin. Immunol. (2005) 116:705-706).*
NDB No. 19868 (Exhibit A, 2007).*
Pulmicort Respules® (booklet Approval 2000, pp. 1-23).*
web page: http://www.scientificpsychic.com/blogentries/splenda-sweetener-the-delusion-of-low-calories.html (2007).*
Caro, J.J. et al., "Healing and relapse rates in gastroesophageal reflux disease treated with the newer proton-pump inhibitors lansoprazole, rabeprazole, and pantoprazole compared with omeprazole, ranitidine, and placebo: evidence from randomized clinical trials," Clin. Thera. 23(7):998-1017 (2001).
PCT/US08/83288 Search Report dated May 18, 2009.
PCT/US08/12783 Search Report dated Jun. 16, 2009.
PCT/US08/12781 Search Report dated Jun. 25, 2009.

(Continued)

*Primary Examiner* — Marcos Sznaidman
(74) *Attorney, Agent, or Firm* — Wilson Sonsini Goodrich & Rosati

(57) ABSTRACT

Provided herein are methods for treating, preventing or alleviating the symptoms of and inflammation associated with inflammatory diseases and conditions of the gastrointestinal tract, for example, those involving the esophagus. Also provided herein are pharmaceutical compositions useful for the methods of the present invention.

48 Claims, No Drawings

(56) References Cited

U.S. PATENT DOCUMENTS

| | | | |
|---|---|---|---|
| 6,562,363 B1 | 5/2003 | Mantelle et al. | |
| 6,565,054 B2 | 5/2003 | Weesner et al. | |
| 6,589,551 B1 | 7/2003 | Jolliffe | |
| 6,589,556 B2 | 7/2003 | Cherukuri | |
| 6,596,261 B1 | 7/2003 | Adjei et al. | |
| 6,598,603 B1* | 7/2003 | Andersson et al. | 128/200.24 |
| 6,638,521 B2 | 10/2003 | Dobrozsi | |
| 6,787,529 B2 | 9/2004 | Hoy et al. | |
| 6,899,099 B2 | 5/2005 | Andersson et al. | |
| 6,916,485 B2 | 7/2005 | Aiache et al. | |
| 6,923,988 B2 | 8/2005 | Patel et al. | |
| 6,962,717 B1 | 11/2005 | Huber et al. | |
| 6,986,904 B2* | 1/2006 | Nilsson et al. | 424/489 |
| 7,063,862 B2 | 6/2006 | Lin et al. | |
| 7,229,641 B2 | 6/2007 | Cherukuri | |
| 7,288,267 B2 | 10/2007 | Bosch et al. | |
| 7,361,646 B2 | 4/2008 | Belanoff | |
| 7,544,348 B2 | 6/2009 | Jacob et al. | |
| 7,547,433 B2 | 6/2009 | Jacob et al. | |
| 7,799,331 B2 | 9/2010 | Asotra | |
| 8,206,727 B2 | 6/2012 | Asotra | |
| 8,324,192 B2 | 12/2012 | Dohil et al. | |
| 8,497,258 B2 | 7/2013 | Dohil et al. | |
| 8,679,545 B2 | 3/2014 | Dohil et al. | |
| 2001/0016577 A1 | 8/2001 | Dobrozsi et al. | |
| 2001/0029255 A1 | 10/2001 | Lindberg et al. | |
| 2001/0049366 A1 | 12/2001 | Singh | |
| 2002/0128216 A1 | 9/2002 | Dean et al. | |
| 2002/0132803 A1 | 9/2002 | Dedhya et al. | |
| 2002/0168334 A1 | 11/2002 | Jacob et al. | |
| 2003/0013693 A1 | 1/2003 | Guivarc'h et al. | |
| 2003/0017189 A1 | 1/2003 | Wong et al. | |
| 2003/0055028 A1 | 3/2003 | Stergiopoulos et al. | |
| 2003/0073676 A1 | 4/2003 | Biggadike et al. | |
| 2003/0192533 A1 | 10/2003 | Andersson et al. | |
| 2003/0215496 A1 | 11/2003 | Patel et al. | |
| 2004/0023935 A1 | 2/2004 | Banerjee et al. | |
| 2004/0028919 A1 | 2/2004 | Houghton et al. | |
| 2004/0053894 A1 | 3/2004 | Mazess et al. | |
| 2004/0115133 A1 | 6/2004 | Wermeling | |
| 2004/0141949 A1 | 7/2004 | Rosenthal et al. | |
| 2005/0042282 A1 | 2/2005 | Ieni | |
| 2005/0049459 A1 | 3/2005 | Minsk et al. | |
| 2005/0079138 A1 | 4/2005 | Chickering et al. | |
| 2005/0095271 A1* | 5/2005 | Mathewson | 424/439 |
| 2005/0152847 A1 | 7/2005 | Trofast et al. | |
| 2005/0153020 A1* | 7/2005 | Hamre et al. | 426/74 |
| 2005/0153946 A1 | 7/2005 | Hirsh et al. | |
| 2005/0158383 A1 | 7/2005 | Boehm et al. | |
| 2005/0208110 A1 | 9/2005 | Singh et al. | |
| 2005/0239845 A1 | 10/2005 | Proehl et al. | |
| 2005/0281772 A1 | 12/2005 | Bromley et al. | |
| 2005/0287181 A1 | 12/2005 | Murthy | |
| 2006/0013873 A1 | 1/2006 | Yang et al. | |
| 2006/0024238 A1 | 2/2006 | Barth | |
| 2006/0128655 A1 | 6/2006 | Falk et al. | |
| 2006/0193783 A1 | 8/2006 | Bhowmick et al. | |
| 2006/0216353 A1 | 9/2006 | Liversidge et al. | |
| 2006/0235053 A1 | 10/2006 | Gebauer | |
| 2007/0020196 A1* | 1/2007 | Pipkin et al. | 424/45 |
| 2007/0031459 A1 | 2/2007 | Asotra et al. | |
| 2007/0104785 A1 | 5/2007 | Navale et al. | |
| 2007/0111978 A1* | 5/2007 | Dohil et al. | 514/179 |
| 2007/0134280 A1 | 6/2007 | Roman et al. | |
| 2007/0248548 A1 | 10/2007 | Blondino et al. | |
| 2007/0259037 A1 | 11/2007 | Guivarc'h et al. | |
| 2008/0008762 A1 | 1/2008 | Robinson et al. | |
| 2008/0132580 A1 | 6/2008 | Mandavilli et al. | |
| 2008/0207771 A1 | 8/2008 | Dikstein | |
| 2008/0226736 A1* | 9/2008 | Caponetti et al. | 424/489 |
| 2009/0123390 A1 | 5/2009 | Hill et al. | |
| 2009/0123551 A1 | 5/2009 | Phillips et al. | |
| 2009/0131386 A1 | 5/2009 | Phillips et al. | |
| 2009/0137540 A1 | 5/2009 | Phillips et al. | |
| 2009/0143343 A1 | 6/2009 | Hill et al. | |
| 2009/0148554 A1* | 6/2009 | Kataoka et al. | 426/2 |
| 2009/0149433 A1 | 6/2009 | Phillips et al. | |
| 2009/0181099 A1 | 7/2009 | Dohil et al. | |
| 2009/0191275 A1 | 7/2009 | Dohil et al. | |
| 2009/0264392 A1 | 10/2009 | Warndahl | |
| 2010/0216754 A1 | 8/2010 | Hill et al. | |
| 2011/0081411 A1 | 4/2011 | Perrett et al. | |
| 2011/0097401 A1 | 4/2011 | Phillips et al. | |
| 2012/0164080 A1 | 6/2012 | Hill et al. | |
| 2013/0096096 A1 | 4/2013 | Dohil et al. | |
| 2013/0296286 A1 | 11/2013 | Dohil et al. | |

FOREIGN PATENT DOCUMENTS

| | | |
|---|---|---|
| EP | 1428526 | 6/2004 |
| EP | 1795183 A1 | 8/2006 |
| JP | 6-107550 | 4/1994 |
| JP | 2001-523638 | 11/2001 |
| JP | 2001-526210 | 12/2001 |
| JP | 2002-519318 | 7/2002 |
| JP | 2005-507000 | 3/2005 |
| JP | 2005-508976 | 4/2005 |
| WO | WO-99-32156 A2 | 7/1999 |
| WO | WO-99-32156 A3 | 7/1999 |
| WO | WO-99-39699 | 8/1999 |
| WO | WO-99-40906 | 8/1999 |
| WO | WO-00-10528 | 3/2000 |
| WO | WO-01-37808 | 5/2001 |
| WO | WO-01-41748 | 6/2001 |
| WO | WO-02-09637 A2 | 2/2002 |
| WO | WO-02-24205 | 3/2002 |
| WO | WO-02-34235 | 5/2002 |
| WO | WO-02-064113 | 8/2002 |
| WO | WO-02-074316 | 9/2002 |
| WO | WO-03-057194 | 7/2003 |
| WO | WO-2004-030652 | 4/2004 |
| WO | WO-2004-045612 A1 | 6/2004 |
| WO | WO-2004-069225 | 8/2004 |
| WO | WO-2004-082590 | 9/2004 |
| WO | WO-2004-082590 A2 | 9/2004 |
| WO | WO-2005-056066 | 6/2005 |
| WO | WO-2005-065185 | 7/2005 |
| WO | WO-2005-074930 A1 | 8/2005 |
| WO | WO-2005-120517 | 12/2005 |
| WO | WO-2006-009825 | 1/2006 |
| WO | WO-2006-035418 | 4/2006 |
| WO | WO-2006-048736 | 5/2006 |
| WO | WO 2006/051980 * | 5/2006 |
| WO | WO-2006-055954 A2 | 5/2006 |
| WO | WO-2006-085101 A2 | 8/2006 |
| WO | WO-2006-099591 A1 | 9/2006 |
| WO | WO-2006-103702 | 10/2006 |
| WO | WO-2007-061803 | 5/2007 |
| WO | WO-2007-075475 | 7/2007 |
| WO | WO-2007-096906 | 8/2007 |
| WO | WO 2008/005802 * | 1/2008 |
| WO | WO-2008-070129 A2 | 6/2008 |
| WO | WO-2008-091855 | 7/2008 |
| WO | WO-99-18938 | 4/2009 |
| WO | WO-2009-064417 | 5/2009 |
| WO | WO-2009-064819 A2 | 5/2009 |
| WO | WO-2009-132048 | 10/2009 |
| WO | WO-2011-041509 | 4/2011 |

OTHER PUBLICATIONS

PCT/US08/12780 Search Report dated Jun. 25, 2009.
PCT/US08/12712 Search Report dated Jun. 25, 2009.
Zhang, L. and Batchelor, H.K., "A bioadhesive formulation for the delivery of antifungal agents to the oesophagus," JPP 56(Suppl.):Poster Session 1 (2004).
U.S. Appl. No. 12/426,858, filed Apr. 20, 2009.
Ashorn et al., "The Natural Course of Gastroesophageal Reflux Disease in Children," Scand. J. Gastroenterol. 37(6):638-641 (2002).
Campieri et al., "Oral budesonide is as effective as oral prednisolone in active Crohn's disease," Gut 41:209-214 (1997).
Cortina et al., "Caustic esophagitis in children," An Esp Pediatr. 36(3):205-207 (1992).
Hanauer, S.B., "Therapy Update: New steroids for IBD: progress report," Gut 51:182-183 (2002).

(56) References Cited

OTHER PUBLICATIONS

Hellers, et al., "Oral Budesonide for Prevention of Postsurgical Recurrence in Crohn's Disease," Gastroenterol. 116:294-300 (1999).
Khan et al., "Esoinophilic Gastroenteritis. Epidemiology, Diagnosis and Management," Pediatr. Drugs 4(9):563-570 (2002).
Konikoff et al., "A Randomized, Double-Blind, Placebo-Controlled Trial of Fluticasone Propionate for Pediatric Eosinophilic Esophagitis," Gastroenterol. 131:1381-1391 (2006).
Li et al., "Clinical and endoscopic features of Chinese reflux esophagitis patients," World J. Gastroenterol,. 14(12):1866-1871 (2008).
Sharpe, S.A. et al., "Comparison of the Flow Properties of Aqueous Suspension Corticosteroid Nasal Sprays Under Differing Sampling Conditions," Drug Dev. Industrial Pharmacy 29(9):1005-1012 (2003).
Sicherer, S.H., "Clinical Aspects of Gastrointestinal Food Allergy in Childhood," Pediatr. 111(6):1609-1616 (2003).
GB0911779.7 Search Report dated Aug. 18, 2009.
Rowe et al., Handbook of Pharmaceutical Excipients, Jan. 1, 2006, Pharmaceutical Press, pp. 442-445.
PCT/US08/83290 Search Report dated Jul. 15, 2009.
PCT/US09/41316 Search Report dated Oct. 30, 2009.
Wang (Blanchard) et al., "Eotaxin-3 and a uniquely conserved gene-expression profile in eosinophilic esophagitis," J. Clin Invest. 116(2):536-547 (2006).
Watts, et al., "TARGITTM technology coated starch capsules for site-specific drug delivery into the lower gastrointestinal tract," Exp. Op. Drug Delivery 2(1):159-167 (2005) (Abstract).
Neumann et al., "A new therapy for eosinophilic esophagitis in adults: Efficacy of budesonide—Rincinol gel for 6 weeks in patients with dysphagia," Am J Gastroenterology 103(Suppl %):S8-S9 (2008).
Pasha et al., "Current concepts and treatment options in eosinophilic esophagitis," Curr Op Invest Drugs 7(11):992-996 (2006).
EP09734222 Supplementary Search Report and Written Opinion mailed Jul. 4, 2011.
Ciaccio et al., "Effect of the dose of oral hydrocortisone on growth rate during long-term treatment of children with salt losing congenital adrenal hyperplasia," Medicina, Buenos Aires 2002:62:551-554.
Copley et al. (Exhibit B), "Understanding the relationship between formulation viscosity and nebulizer performance," poster presented at DDL 19, Dec. 10-12, 2008 (Edinburg, Scotland) [online][retrieved on Aug. 27, 2012]. Retrieved from the Internet:<URL:http://www.malvern.com/common/downloads/campaign/FormulationViscosity_NebuliserPerformance.pdf>.
DeMuth, "Treatment of Allergic Esophagitis with Budesonide Turbuhaler," J. Allergy Clin. Immunol., 113(2Suppl);S316 (2004)(Abstract Only).
Dobrozsi et al., "Comparative mucoretention of sucralfate suspensions in an everted rat esophagus model," International Journal of Pharmaceutics, 189:81-89 (1999).
Fawcett et al., "Stability of Hydrocortisone Oral Suspensions Prepared from Tablets and Powder," Annals of Pharmacotherapy, 29(10):987-990 (1995).
Furuta et al., "Stability of hydrocortisone oral suspensions prepared from tablets and powder," Journal of Pediatric Gastroenterology & Nutrition, 26(4):468-471 (1998).
Garcia et al., "Viscosity measurements of nectar- and honey-thick liquids: product, liquid, and time comparisons," Dysphagia, 20:325-335 (2005).
Jiang, et al., "Effects of antireflux treatment on bronchial hyper-responsiveness and lung function in asthmatic patients with gastroesophageal reflux disease," World Journal of Gastroenterology 9:1123-1125 (2003).
Lotong et al., "Texture and flavor characteristics of beverage containing commercial thickening agents for dysphagia diets," Journal of Food Science, 68(4):1537-1541 (2003).
Martin, Physical Pharmacy, 4$^{th}$ Ed., p. 423, (1993) published by Lea & Febiger.

McCallion et al. (Exhibit C), "Nebulization of fluids of different physicochemical properties with air-jet and ultrasonic nebulizers," Pharm. Res. 12:1682-1688 (1995).
Noureddini et al., "Viscosities of Vegetable Oils and Fatty Acids," JAOCS, 69(12):1189-1191 (1992).
Pulmicort tubuhaler monograph, AstraZeneca, Dec. 2001.
Noel, et al., "Clinical and Immunopathologic Effects of Swallowed Fluticasone for Eosinophilic Esophagitis," Clinical Gastroenterology and Hepatology, 2004, vol. 2, pp. 568-575.
AU App. No. 2008321030 Examiner's Report dated Apr. 8, 2011.
Blanchard et al., "Eotaxin-3 and a uniquely conserved gene-expression profile in eosinophilic esophagitis," J. Clin Invest., 116(2):536-547 (2006).
CA App. No. 2,704,946 Examiner's Report dated Jun. 18, 2012.
CA App. No. 2,704,946 Examiner's Report dated Nov. 22, 2011.
CN200880125118 Office action mailed Jun. 8, 2013.
CN200880125118 Office action mailed Feb. 7, 2013.
CN200880125118 Office action mailed Jun. 1, 2012.
CN200880125118 Office action mailed Oct. 10, 2011.
Dickman, et al. The American Journal of Gastroenterolgy (2006) 101: 2463-2469.
EP 08876449.3 Exam Report dated Jun. 11, 2013.
EP 08848917.4 Extended European Search Report Dated Aug. 26, 2013.
EP 08850126.7 Extended European Search Report Dated Aug. 28, 2013.
EP 08848597.4 Extended European Search Report Dated Aug. 26, 2013.
Freers, "Maltodextrin," Handbook of Pharmaceutical Excipients, 5th edition, 2006: 442-444.
JP2010-533128 Office Action dated Jul. 23, 2013.
PCT/US10/038411 Search Report dated Mar. 22, 2011.
PCT/US11/41871 Search Report dated Feb. 9, 2012.
PCT/US2008/083290 IPRP dated Feb. 22, 2011.
PCT/US2008/83288 International Preliminary Report dated May 18, 2010.
Suarez et al., "Caustic esophagitis in children," Anales Espanoles de Pediatria, Mar. 1992, 36(3):205-207, Abstract, 1 page.
Szefler, Pharmacodynamics and Pharmacokinetics of budesonide: A new nebulized corticosteroid, Oct. 1999, Journal of Allergy and Clinical Immunology, vol. 104, pp. S175-S182.
U.S. Appl. No. 11/595,513 Office Action mailed Feb. 6, 2012.
U.S. Appl. No. 11/595,513 Office Action mailed May 12, 2011.
U.S. Appl. No. 11/595,513 Office Action mailed Jan. 7, 2010.
U.S. Appl. No. 11/595,513 Office Action mailed Jun. 30, 2010.
U.S. Appl. No. 12/269,693 Office Action mailed Feb. 9, 2012.
U.S. Appl. No. 12/269,693 Office Action mailed Jul. 19, 2012.
U.S. Appl. No. 12/269,693 Office Action mailed Jun. 1, 2011.
U.S. Appl. No. 12/762,222 Office Action mailed Aug. 8, 2012.
U.S. Appl. No. 12/762,222 Office Action mailed Mar. 13, 2013.
U.S. Appl. No. 12/762,222 Office Action mailed May 16, 2013.
U.S. Appl. No. 12/269,572 Office Action mailed Dec. 21, 2012.
U.S. Appl. No. 12/269,572 Office Action mailed Jun. 7, 2012.
U.S. Appl. No. 12/269,572 Office Action mailed Mar. 5, 2010.
U.S. Appl. No. 12/269,572 Office Action mailed Oct. 12, 2011.
U.S. Appl. No. 12/269,572 Office Action mailed Oct. 25, 2010.
U.S. Appl. No. 12/269,740 Office Action mailed Jun. 8, 2011.
U.S. Appl. No. 12/269,740 Office Action mailed Nov. 17, 2010.
U.S. Appl. No. 12/269,821 Office Action mailed Apr. 26, 2011.
U.S. Appl. No. 12/269,832 Office Action mailed May 4, 2011.
U.S. Appl. No. 12/426,858 Office Action mailed Jun. 1, 2011.
U.S. Appl. No. 12/814,335 Office Action mailed Dec. 21, 2011.
U.S. Appl. No. 12/814,335 Office Action mailed Jul. 17, 2012.
U.S. Appl. No. 13/168,601 Office Action mailed Apr. 9, 2013.
U.S. Appl. No. 13/168,601 Office Action mailed Jul. 3, 2012.
CA App. No. 2,705,681 Office Action dated Nov. 21, 2011.
CA App. No. 2,705,681 Office Action dated Jun. 19, 2012.
EP 08876449.3 Office Action Dated Jul. 21, 2011.
EP 10786942.2 Search Report dated Jan. 8, 2014.
EP 11799004.4 Extended European Search Report Dated Oct. 29, 2013.
IL205740 Office Action dated Sep. 19, 2012.
JP2010-533128 Office Action dated Nov. 6, 2012.

(56) References Cited

OTHER PUBLICATIONS

KR10-2010-7010579 Office Action dated Feb. 16, 2012.
NZ585268 Office Action dated Feb. 8, 2011.
NZ585268 Office Action dated May 8, 2012.
PCT/US08/12712 International Preliminary Report on Patentability dated May 18, 2010.
PCT/US2008/12780 International Preliminary Report on Patentability dated May 18, 2010.
PCT/US2008/12781 International Preliminary Report on Patentability dated May 18, 2010.
PCT/US2008/12783 International Preliminary Report on Patentability dated May 18, 2010.
PCT/US2009/41316 International Preliminary Report on Patentability dated Oct. 26, 2010.
PCT/US10/038411 International Preliminary Report on Patentability dated Dec. 12, 2011.
PCT/US11/41871 International Preliminary Report on Patentability dated Dec. 2, 2012.
RU2010119165 Office Action dated Aug. 30, 2012.
RU2010119165 Office Action dated Nov. 3, 2011.
RU2010119165 Office Action dated Apr. 3, 2012.
RU2010119165 Office Action dated Aug. 12, 2010.
U.S. Appl. No. 12/762,222 Office Action mailed Dec. 4, 2013.
U.S. Appl. No. 13/168,601 Office Action mailed Feb. 24, 2014.
U.S. Appl. No. 13/690,807 Office Action mailed Oct. 23, 2013.
U.S. Appl. No. 12/269,650 Office Action mailed Oct. 3, 2013.
U.S. Appl. No. 12/269,650 Office Action mailed Feb. 23, 2012.
U.S. Appl. No. 12/269,650 Office Action mailed Sep. 19, 2012.
Aceves et al., "Prospective Analysis of an Abdominal Symptom Scoring Tool's Efficacy in the Clinical Distinction of Pediatric Eosinophilic Esophagitis from Gastroesophageal Reflux Disease," J. Allergy Clin. Immunol. Feb. 2008, S70 Abstracts No. 270.
Aceves, SS et al., "Oral viscous budesonide: A potential new therapy for eosinophilic esophagitis," Amer. Journal of Gastroenterology 2007; 102:1-9.
Aceves, S et al., "Distinguishing Eosinophilic Esophagitis in pediatric patients: clinical, endoscopic, and histologic features of an emerging disorder," Journal of Clinical Gastroenterology 2006; 41(3):252-6.
Aceves, SS et al. "Topical viscous budesonide suspension for treatment of eosinophilic esophagitis," J. Allergy Clin. Immunol. 2005; 116:705-6.
Batchelor, H.K. et al., "An in vitro mucosal model for prediction of the bioadhesion of alginate solutions to the oesophagus," Intl. J. Pharma. 238:123-132 (2002).
Batchelor, H.K. et al., "Feasibility of a bioadhesive drug delivery system targeted to oesophageal tissue," Eur. J. Pharmaceutics Biopharma. 57:295-298 (2004).
Batchelor, H., "Bioadhesive Dosage Forms for Esophageal Drug Delivery," Pharma. Res. 22(2):175-181 (2005).
Bogaart, H.C.A. et al., "Viscosity Is Not a Parameter of Postdeglutitve Pharyngeal Residue: Quantification and Analysis with Scintigraphy," Dysphagia 22:145-149 (2007).
Bonis, P.A. et al., "Eosinophilic esophagitis," http://www.uptodate.com/online/content/topic.do?topicKey=eso_dis./11927&view=print.
Budin, C et al. "Eosinophilic esophagitis: 3 case reports," Gastroenterol. Clin. Biol. 2005; 29:73-5.
Cheung, K M et al., "Esophageal eosinophilia in children with dysphagia," J. Pediatr. Gastroenterol. Nutr. 2003;37:498-503.
Cherian S et al., "Rapidly increasing prevalence of eosinophilic oesophagitis in Western Australia," Arch. Dis. Child 2006; 91:1000-4.
Christup, L.L. et al., "Deposition of a model substance, $^{99m}$Tc E-HIDA, in the oral cavity after administration of lozenges, chewing gum and sublingual tablets," Intl. J. Pharmaceutics 66:169-174 (1990).
Collaud, S. et al., "Clinical evaluation of bioadhesive hydrogels for topical delivery of hexylaminolevulinate to Barrett's esophagus," J. Controlled Release 123:203-210 (2007).

Croese J et al., "Clinical and endoscopic features of eosinophilic esophagitis in adults," Gastrointest. Endosc. 2003; 58:516-22.
Desai T K et al., "Association of eosinophilic inflammation with esophageal food impaction in adults," Gastrointest. Endosc. 2005; 61:795-801.
Dobroszi, D. et al., "Comparative mucoretention of sucralfate suspensions in an everted rat esophagus model," Intl. J. Pharmaceutics 189:81-89 (1999).
Dohil R et al., "The evaluation and treatment of gastrointestinal disease in children with cystinos is receiving cysteamine," J. Pediatr, 2003; 14:224-30.
Faubion W A, Jr. et al., "Treatment of eosinophilic esophagitis with inhaled corticosteroids," J. Pediatr. Gastroenterol. Nutr. 1998; 27:90-3.
Fogg M I et al., "Pollen and eosinophilic esophagitis," J. Allergy Clin. Immunol. 2003; 112:796-7.
Fox V L et al., "Eosinophilic esophagitis: it's not just kid's stuff," Gastrointest. Endosc. 2002; 56:260-70.
Furuta, GT et al., "Eosiniophilic esophagitis in children and adults: A systematic review and consensus recommendations for diagnosis and treatment," Gastroenterology 2007; 133:1342-1363.
Garrett J K et al., "Anti-interleukin-5 (mepolizumab) therapy for hypereosinophilic syndromes," J. Allergy Clin. Immunol. 2004; 113:115-9.
Gliani, K. et al., "Aerosolisation properties of disodium cromoglycate microparticles spray dried from different water to ethanol ratio," JPP S6(Suppl.):Abstract 043 (2004).
Guajardo J R et al., "Eosinophil-associated gastrointestinal disorders: a world-wide-web based registry," J. Pediatr. 2002; 141:576-81.
Hardy, J.G. et al., "A Comparison of the Gastric Retention of a Sucralate Gel and a Sucralate Suspension," Eur. J. Pharm. Biopharm. 39(2):70-74 (1993).
Honkanen, O. et al., "Bioavailability and in vitro oesophageal sticking tendency of hydroxypropyl methylcellulose capsul formulations and corresponding gelatine capsul formulations," Eur. J. Pharm. Sci. 15:479-488 (2002).
Ishibashi, H. et al., "Oral administration of itraconazole solution has superior efficacy in experimental oral and oesophageal candidiasis in mice than its intragastric administration," J. Antimicrobial Chemotherapy 59:317-320 (2007).
Kagalwalla A F et al., "Effect of six-food elimination diet on clinical and histologic outcomes in eosinophilic esophagitis," Clin. Gastroenterol. Hepatol. 2006; 4:1097-102.
Karnam, U. and Hirano, I., "Effectiveness of Oral Budesonide Suspension in Adult Patients with Eosinophilic Esophagitis," http://download.abstractcentral.com/ddw2008/myddw2008/S1974.html.
Kelly K J et al., "Eosinophilic esophagitis attributed to gastroesophageal reflux: improvement with an amino acid-based formula," Gastroenterology 1995; 109: 1503-12.
Laine, L. and Rabeneck, L., "Prospective study of fluconazole suspension for the treatment of oesophageal candidiasis in patients with AIDS," Ailment Pharmacol.Ther. 9:553-556 (1995).
Liacouras C A., "Eosinophilic esophagitis: treatment in 2005," Curr. Opin. Gastroenterol. 2006; 22:147-152.
Liacouras C A and Ruchelli E., "Eosinophilic esophagitis," Cuff. Opin. Pediatr. 2004; 16:560-6.
Liacouras C A et al., "Primary eosinophilic esophagitis in children: successful treatment with oral corticosteroids," J. Pediatr. Gastroenterol. Nutr. 1998; 26:380-5.
Liacouras C A et al., "Eosinophilic esophagitis: a 10-year experience in 381 children," Clin. Gastroenterol. Hepatol. 2005; 3:1198-206.
Markowitz J E et al., "Elemental diet is an effective treatment for eosinophilic esophagitis in children and adolescents," Am. J. Gastroenterol. 2003; 98:777-82.
Martins, M.D. and Rex, J.H., "Fluconazole Suspension for Oropharyngeal Candidiasis Unresponsive to Tablets," Annals Internal Med. 126(4):332-333 (1997).
Mishra A et al., "An etiological role for aeroallergens and eosinophils in experimental esophagitis," J. Clin. Invest. 2001; 107:83-90.
Mueller S et al., "Eosinophil infiltration and degranulation in oesophageal mucosa from adult patients with eosinophilic oesophagitis: a retrospective comparative study on pathologic biopsy," J. Clin. Pathol. 2006; 59:1175-80.

(56) References Cited

OTHER PUBLICATIONS

Newman, S.P. et al., "New developments in radionuclide imaging for assessing drug delivery in man," Eur. J. Pharma. Sci. 18:19-22 (2003).
Nicolazzo, JA et al., "Buccal penetration enhancers—how do they really work?" J. Controlled Release 2005; 105:1-15.
Noel R J et al., "Clinical and immunopathologic effects of swallowed fluticasone for eosinophilic esophagitis," Clin. Gastroenterol. Hepatol. 2004; 2:568-75.
Noel R J et al., "Eosinophilic esophagitis," N. Engl. J. Med. 2004; 351:940-1.
Oliviera, C. et al., "Eosinophilic esophagitis and intermediate esophagitis after tracheoesophageal fistula repair: a case series," J. Ped. Surg. 43:810-814 (2008).
Orenstein S R et al., "The spectrum of pediatric eosinophilic esophagitis beyond infancy: a clinical series of 30 children," Am. J. Gastroenterol. 2000; 95:1422-30.
Parfitt J R et al., "Eosinophilic esophagitis in adults: distinguishing features from gastroesophageal reflux disease: a study of 41 patients," Mod. Pathol. 2006; 19:90-6.
Plaza-Martin, AM et al., "Polysensitization to aeroallergens and food in eosinophilic esophagitis in a pediatric population," Alergol. Immunopathol. 2007; 35:35-7.
Potter J W et al., "Eosinophilic esophagitis in adults: an emerging problem with unique esophageal features," Gastrointest. Endosc. 2004; 59:355-61.
Potts, A.M. et al., "In vivo determination of the oesophageal retention of smart hydrogel," The 24$^{th}$ International Symposium on Controlled Release of Bioactive Materials, Stockholm Sweden, Jun. 15-19, 1997 #5058, pp. 335-336.
Ravelli A M et al., "Dilated Intercellular Spaces: A Major Morphological Feature of Esophagitis," J. Pediatr. Gastroenterol. Nutr. 2006; 42:510-515.
Remedios M et al., "Eosinophilic esophagitis in adults: clinical, endoscopic, histologic findings, and response to treatment with fluticasone propionate," Gastrointest. Endosc. 2006; 63:3-12.
Richardson, J.C. et al., "Oesophageal bioadhesion of sodium alginate suspensions: particle swelling and mucosal retention," Eur. J. Pharm. Sci. 23:49-56 (2004).
Rothenberg M E., Eosinophilic gastrointestinal disorders, J. Allergy Clin. Immunol. 2004; 113:11-28.
Rothenberg M E, et al., "Pathogenesis and clinical features of eosinophilic esophagitis," J. Allergy Clin. Immunol. 2001; 108: 891-4.
Ruchelli E et al., "Severity of esophageal eosinophilia predicts response to conventional gastroesophageal reflux therapy," Pediatr. Dev. Pathol. 1999; 2:15-8.
Sant'Anna A M et al., "Eosinophilic Esophagitis in Children: Symptoms, Histology and pH Probe Results," J. Pediatr. Gastroenterol. Nutr. 2004; 39:373-377.
Shah, A. and Hirano, I., "Treatment of Eosinophilic Esophagitis: Drugs, Diet, or Dilation?" Curr. Gastroent. Reports 9:181-188 (2007).
Smart, J.D. et al., "The retention of $^{14}$C-labelled poly(acrylic acids) on gastric and oesaphageal mucosa: an in vitro study," Eur. J. Pharma. Sci. 20:83-90 (2003).
Spergel JM., "Eosinophilic esophagitis in adults and children: evidence for a food allergy component in many patients," Curr. Opin. Allergy Clin. Immunol. 2007; 7:274-8.
Spergel J M et al., "Treatment of eosinophilic esophagitis with specific food elimination diet directed by a combination of skin prick and patch tests," Ann. Allergy Asthma Immunol. 2005; 95:336-43.
Spergel J M et al., "The use of skin prick tests and patch tests to identify causative foods in eosinophilic esophagitis," J. Allergy Clin. Immunol. 2002; 109:363-8.
Steiner S J et al., "Correlation between number of eosinophils and reflux index on same day esophageal biopsy and 24 hour esophageal pH monitoring," Am. J. Gastroenterol. 2004; 99:801-5.
Steiner S J et al., "Severity of Basal Cell Hyperplasia Differs in Reflux Versus Eosinophilic Esophagitis," J. Pediatr. Gastroenterol. Nutr. 2006; 42:506-509.
Straumann A and Simon H U, "Eosinophilic esophagitis: escalating epidemiology?" J. Allergy Clin. Immunol. 2005; 115:418-9.
Straumann A et al., "Natural history of primary eosinophilic esophagitis: a follow-up of 30 adult patients for up to 11.5 years," Gastroenterology 2003; 125:1660-9.
Tang, M. et al., "Bioadhesive oesophageal bandages: protection against acid and pepsin injury," Int. J. Pharma. 292:169-177 (2005).
Teitelbaum J E et al., "Eosinophilic esophagitis in children: immunopathological analysis and response to fluticasone propionate," Gastroenterology 2002; 122:1216-25.
Varum, F.J.O. et al., "Mucoadhesion and the Gastrointestinal Tract," Critical Reviews Ther. Drug Carrier Systems 25(3):207-258 (2008).
Wise, J.L. et al., "Regional differences in oesophageal motor function," Neurogastroenterol. Motil 16:31-37 (2004).
Young, S.A. and Smart, J.D., "A novel in-vitro apparatus for evaluating the mucoadhesion of liquid and semi-solid formulations," J. Pharm. Pharmacol. 50(Suppl):167 (1998).

\* cited by examiner

CORTICOSTEROID COMPOSITIONS

CROSS-REFERENCE

This application claims the benefit of U.S. Provisional Application No. 60/987,720, filed Nov. 13, 2007; U.S. Provisional Application No. 61/012,012, filed Dec. 6, 2007; U.S. Provisional Application No. 61/015,998, filed Dec. 21, 2007; U.S. Provisional Application No. 61/019,818, filed Jan. 8, 2008; U.S. Provisional Application No. 61/034,941, filed Mar. 7, 2008; U.S. Provisional Application No. 61/035,348, filed Mar. 10, 2008; U.S. Provisional Application No. 61/054,103, filed May 16, 2008; U.S. Provisional Application No. 61/054,104, filed May 16, 2008; U.S. Provisional Application No. 61/054,105, filed May 16, 2008; U.S. Provisional Application No. 61/054,106, filed May 16, 2008; U.S. Provisional Application No. 61/054,107, filed May 16, 2008; and U.S. Provisional Application No. 61/090,568, filed Aug. 20, 2008, which applications are incorporated herein by reference.

BACKGROUND OF THE INVENTION

Esophageal inflammation disorders are gaining increased recognition in both adults and children. One example is eosinophilic esophagitis (EE or EoE), which is an emerging, and fast-growing disorder characterized by high levels of eosinophils in the esophagus, as well as basal zone hyperplasia. EE (EoE) is thought to be provoked, in at least a subset of patients, by food allergies or airborne allergen exposure (1-5, 44). EE (EoE) diagnosis is often associated with other hypersensitivity disorders, including asthma, rhinitis, and other food and aeroallergen inhalant sensitivities (39-40). Diagnosis is often made, e.g., in young children and depends on the finding of 15 to 20 or more to 24 or more eosinophils per high power field (eos/hpf) within esophageal mucosal biopsies (6-12).

In parallel with other atopic disorders, the incidence of EE (EoE) appears to be increasing (15, 35). The disorder may present with reflux-like symptoms, pain and dysphagia, clinical symptoms similar to the presentation of gastroesophageal reflux disease ("GERD") (42). Symptoms of EE (EoE) include, for example, abdominal pain, chest pain, choking, difficulty swallowing, failure to thrive, nausea, reflux not relieved by standard anti-flux therapy, skin rash or hives, vomiting, and weight loss. In one series, 15% of EE (EoE) patients had concurrent developmental delay (45).

Although EE (EoE) is becoming more frequently diagnosed throughout developing countries (7, 8, 13-16) many aspects of the disease remain unclear including its etiology, natural history and optimal therapy. Symptoms of EE (EoE) often mimic those of GERD and include vomiting, dysphagia, pain and food impaction (8, 14, 17-20). However, treatment of EE (EoE) and GERD differ and it is important to distinguish between them, particularly as untreated EE (EoE) may be associated with esophageal narrowing in 10-30% of cases (14, 18, 20, 21). The overlap of GERD and EE (EoE) symptoms is common; failure to respond to high PPI GERD treatment may be one diagnostic guideline for EE (EoE) (42). The common occurrence regarding misdiagnosis of EE (EoE) for GERD often results in delayed treatment for patients with EE. (42).

Long term systemic steroid therapy can result in significant secondary side effects on growth and bone development. Although treatment with anti-IL-5 monoclonal antibody has been reported to be successful in EE, this therapy is currently not approved for use in children (36).

Current treatments include elimination diets (22, 23), and elemental formulas (2, 24). Identifying true inciting food allergens can be difficult and elemental formulas are often unpalatable, thereby making dietary interventions complicated (1, 22). Improvised puff and swallow techniques may be difficult for patients, especially smaller children, and especially children with developmental delays, to perform efficiently. This may result in a less than effective dose of a topical steroid being delivered to the esophagus.

SUMMARY OF THE INVENTION

Certain embodiments herein provide for a pharmaceutical composition comprising a physically and chemically stable composition comprising:
 a. a therapeutically effective amount of corticosteroid,
 b. edetate,
 c. citrate,
 d. polysorbate 80,
 e. an optional preservative,
 f. an optional flavoring agent,
 g. an optional sweetener,
 h. at least one additional excipient, and
 i. a liquid vehicle.

In some embodiments, a pharmaceutical composition provided herein is suitable for single or multiple dose administration. In certain embodiments, a pharmaceutical composition described herein is in a multiple-unit container and comprising a plurality of unit doses. In some embodiments, a composition described herein remains substantially uniform after storage. In certain embodiments, a pharmaceutical composition described herein remains substantially uniform after storage for the shelf life of the formulation. In some embodiments, a pharmaceutical composition described herein has a fluid, liquid, solution, suspension, solid, semi-solid, gel, cream, ointment, spreadable, flowable, or paste-like consistency. In certain embodiments, a pharmaceutical composition described herein obtains or regains substantial uniformity upon mild or moderate agitation, swirling, gentle swirling or shaking. In some embodiments, a pharmaceutical composition described herein obtains or regains substantial uniformity upon mild or moderate agitation, swirling, gentle swirling or shaking. In certain embodiments, after mild or moderate agitation, swirling, gentle swirling or shaking, the pharmaceutical composition described herein remains substantially uniform for a convenient period of time, including, by way of non-limiting example, for at least 1, 2, 4, 6, 12, 18, or 24 hours, or 2, 3, 4, 5 or more days.

In certain embodiments, a pharmaceutical composition described herein is a multiple dose formulation. In certain embodiments, each dose (e.g., from a multiple unit container containing a plurality of doses of the pharmaceutical composition) of the formulation is substantially uniform with regard to one another. In some embodiments, the first and final dose (e.g., from a multiple unit container containing a plurality of doses of the pharmaceutical composition) are substantially uniform.

In some embodiments, a pharmaceutical composition described herein comprises a corticosteroid that is readily dispersed throughout the composition upon agitation (e.g., mild or moderate). In certain embodiments, a pharmaceutical composition described herein comprises a corticosteroid that is readily dispersed throughout the composition upon mild or moderate agitation after storage. In some embodiments, a pharmaceutical composition described herein comprises a corticosteroid that is easily resuspended in the composition upon mild or moderate agitation. In certain embodiments, a pharmaceutical composition described herein comprises a corticosteroid that is easily resuspended in the composition upon mild or moderate agitation after storage. In some embodiments, a pharmaceutical composition described herein comprises a corticosteroid that is readily dispersed throughout the composition upon mild or moderate agitation. In certain embodiments, a pharmaceutical composition described herein comprises a corticosteroid that is readily dispersed throughout the composition upon mild or moderate agitation after storage. In certain embodiments, the ability of the compositions described herein are able to be easily resuspended and/or readily redispersed after storage under ambient conditions. In other embodiments, the storage is under an inert atmosphere, increased temperature and/or increased relative humidity. In certain embodiments, the ability of the compositions described herein are able to be easily resuspended and/or readily redispersed after storage for, by way of non-limiting example, 1 day, 2 days, 3 days, 1 week, 2 weeks, 3 weeks, 1 month, 3 months, 6 months, 1 year, 2 years, or the time of the shelf life.

In certain embodiments, a pharmaceutical composition described herein does not cake or aggregate during or after storage (e.g., the corticosteroid does not sediment and form a solid cake or fuse).

In some embodiments, a pharmaceutical composition described herein is a dispersion, suspension or solution. In certain embodiments, a pharmaceutical composition described herein is a solution, except that substantially all of the corticosteroid is dispersed or suspended as particles in the solution (e.g., less than about 36 µg of budesonide is in solution). In some embodiments, the at least one excipient does not enhance the solubility of the corticosteroid in the liquid vehicle.

In certain embodiments, a pharmaceutical composition described herein is a non-Newtonian fluid. In some embodiments, the non-Newtonian fluid is selected from, by way of non-limiting example, a plastic, a pseudo-plastic and a dilatant. In certain embodiments, the non-Newtonian fluid is pseudo-plastic. In some embodiments, the non-Newtonian fluid is thixotropic.

In certain embodiments, the corticosteroid is topically active (e.g., topically active on a gastrointestinal surface, such as the esophageal surface). In some embodiments, the corticosteroid is budesonide. In other embodiments, the corticosteroid is fluticasone propionate. In some embodiments, the corticosteroid is a particle (e.g., a microparticle or a nanoparticle).

In certain embodiments, the additional excipient is selected from, by way of non-limiting example, cellulose (including derivatives thereof), one or more maltodextrin, dextrose, hydroxyethylcellulose (HEC), hydroxypropylmethyl-cellulose (HPMC), carboxymethyl-cellulose (CMC), microcrystalline cellulose (MCC), carbomer and combinations thereof. In more specific embodiments, the at least one additional excipient comprises hydroxyethylcellulose (HEC), hydroxypropylmethyl-cellulose (HPMC), carboxymethyl-cellulose (CMC), microcrystalline cellulose (MCC), carbomer and combinations thereof, and the at least one additional excipient is present in the pharmaceutical composition in an amount of about 5 mg/mL to about 100 mg/mL. In some specific embodiments, the at least one additional excipient comprises, by way of non-limiting example, maltodextrin, dextrose and combinations thereof, and the at least one additional excipient is present in an amount of about 1 mg/mL to about 1.5 g/mL.

In certain embodiments, the liquid vehicle comprises an aqueous medium.

In some embodiments, a pharmaceutical composition described herein comprises corticosteroid particles suspended in the aqueous medium. In certain embodiments, the corticosteroid particles are microparticles having a mean diameter of, by way of non-limiting example, about 0.1 microns to about 50 microns. In some embodiments, at least 95%, at least 97%, at least 98%, or at least 99% of the corticosteroid particles are microparticles having a diameter of less than about 10 microns.

In certain embodiments, provided herein is a pharmaceutical composition wherein corticosteroid is present in an amount of about 0.01 mg/mL to about 1 mg/mL. In certain embodiments, the pharmaceutical composition has a total volume of about 1 mL to about 20 mL, about 1 mL to about 10 mL, about 1 mL to about 15 mL, or about 3 mL to about 7 mL, about 5 mL, about 10 mL, about 15 mL, or about 20 mL. In specific embodiments, a pharmaceutical composition described herein comprises about 0.1 mg to about 5 mg, about 0.25 mg to about 5 mg, about 0.3 to about 2 mg, or about 0.5 mg to about 5 mg.

In some embodiments, the at least one additional excipient comprises CMC, and the CMC is present in the pharmaceutical composition in an amount of about 5 mg/mL to about 30 mg/mL. In certain embodiments, the at least one additional excipient comprises carbomer, and the carbomer is present in the pharmaceutical composition in an amount of about 5 mg/mL to about 100 mg/mL. In some embodiments, the at least one additional excipient comprises HPMC, and the HPMC is present in the pharmaceutical composition in an amount of about 5 mg/mL to about 30 mg/mL. In certain embodiments, the at least one additional excipient comprises MCC, and the MCC is present in the pharmaceutical composition in an amount of about 5 mg/mL to about 30 mg/mL. In some embodiments, the at least one additional excipient comprises a combination of CMC and MCC, and the CMC-MCC combination is present in an amount of about 5 mg/mL to about 40 mg/mL, and wherein the CMC/MCC mixed weight ratio is about 11/89. In certain embodiments, the at least one additional agent comprises dextrose and the dextrose is present in the pharmaceutical composition in an amount of about 10 mg/mL to about 1 g/mL. In some embodiments, the at least one additional agent comprises maltodextrin and the maltodextrin is present in the pharmaceutical composition in an amount of about 10 mg/mL to about 1 g/mL.

In certain embodiments, edetate is present in the pharmaceutical composition an amount of about 0.05 mg/mL to about 25 mg/mL. In some embodiments, citrate is present in the pharmaceutical composition in an amount of about 0.1 mg/mL to about 30 mg/mL. In certain embodiments, polysorbate 80 is present in the pharmaceutical composition in an amount of 0.05 mg/mL to about 1 mg/mL.

In further or alternative embodiments, provided herein is a pharmaceutical composition comprising:
  a. budesonide in an amount of about 0.02 mg/mL to about 0.75 mg/mL,
  b. edetate in an amount of about 0.05 mg/mL to about 25 mg/mL,
  c. citrate in an amount of about 0.1 mg/mL to about 30 mg/mL,
  d. polysorbate 80 in an amount of 0.05 mg/mL to about 1 mg/mL,
  e. a preservative,
  f. a flavoring agent, a sweetener, or a combination thereof,
  g. at least one additional excipient, and
  h. an aqueous liquid vehicle.

In further or alternative embodiments, provided herein is a pharmaceutical composition comprising:
 a. budesonide in an amount of about 0.05 mg/mL to about 0.75 mg/mL,
 b. edetate in an amount of about 0.05 mg/mL to about 25 mg/mL,
 c. citrate in an amount of about 0.1 mg/mL to about 30 mg/mL,
 d. polysorbate 80 in an amount of 0.05 mg/mL to about 1 mg/mL,
 e. a preservative,
 f. a flavoring agent, a sweetener, or a combination thereof,
 g. at least one additional excipient, and
 h. an aqueous liquid vehicle.

In further or alternative embodiments, provided herein is a pharmaceutical composition comprising:
 a. budesonide in an amount of about 0.1 mg/mL to about 0.75 mg/mL,
 b. edetate in an amount of about 0.05 mg/mL to about 25 mg/mL,
 c. citrate in an amount of about 0.1 mg/mL to about 30 mg/mL,
 d. polysorbate 80 in an amount of 0.05 mg/mL to about 1 mg/mL,
 e. a preservative,
 f. a flavoring agent, a sweetener, or a combination thereof,
 g. at least one additional excipient, and
 h. an aqueous liquid vehicle.

In specific embodiments, a pharmaceutical composition provided herein has a total volume of about 1 mL to about 20 mL, or about 1 mL to about 15 mL.

Certain embodiments herein provide for a pharmaceutical composition comprising a physically and chemically stable composition comprising:
 a. a therapeutically effective amount of corticosteroid,
 b. a preservative,
 c. a buffer,
 d. a surface active agent or a surfactant,
 e. an optional preservative,
 f. an optional flavoring agent,
 g. an optional sweetener,
 h. at least one additional excipient, and
 i. a liquid vehicle.

In some embodiments, a pharmaceutical composition provided herein is suitable for single or multiple dose administration. In certain embodiments, a pharmaceutical composition described herein is in a multiple-unit container and comprising a plurality of unit doses. In some embodiments, a composition described herein remains substantially uniform after storage. In certain embodiments, a pharmaceutical composition described herein remains substantially uniform after storage for the shelf life of the formulation. In some embodiments, a pharmaceutical composition described herein has a solid, semi-solid, gel, cream, ointment, spreadable, flowable, or paste-like consistency. In certain embodiments, a pharmaceutical composition described herein obtains or regains substantial uniformity upon mild or moderate agitation, swirling, gentle swirling or shaking. In some embodiments, a pharmaceutical composition described herein obtains or regains substantial uniformity upon mild or moderate agitation, swirling, gentle swirling or shaking. In certain embodiments, after mild or moderate agitation, swirling, gentle swirling or shaking, the pharmaceutical composition described herein remains substantially uniform for a convenient period of time, including, by way of non-limiting example, for at least 1, 2, 4, 6, 12, 18, or 24 hours, or 2, 3, 4, 5 or more days.

In certain embodiments, a pharmaceutical composition described herein is a multiple dose formulation. In certain embodiments, each dose (e.g., from a multiple unit container containing a plurality of doses of the pharmaceutical composition) of the formulation is substantially uniform with regard to one another. In some embodiments, the first and final dose (e.g., from a multiple unit container containing a plurality of doses of the pharmaceutical composition) are substantially uniform.

In some embodiments, a pharmaceutical composition described herein comprises a corticosteroid that is readily dispersed throughout the composition upon agitation (e.g., mild or moderate). In certain embodiments, a pharmaceutical composition described herein comprises a corticosteroid that is readily dispersed throughout the composition upon mild or moderate agitation after storage. In some embodiments, a pharmaceutical composition described herein comprises a corticosteroid that is easily resuspended in the composition upon mild or moderate agitation. In certain embodiments, a pharmaceutical composition described herein comprises a corticosteroid that is easily resuspended in the composition upon mild or moderate agitation after storage. In some embodiments, a pharmaceutical composition described herein comprises a corticosteroid that is readily dispersed throughout the composition upon mild or moderate agitation. In certain embodiments, a pharmaceutical composition described herein comprises a corticosteroid that is readily dispersed throughout the composition upon mild or moderate agitation after storage. In certain embodiments, the ability of the compositions described herein are able to be easily resuspended and/or readily redispersed after storage under ambient conditions. In other embodiments, the storage is under an inert atmosphere, increased temperature and/or increased relative humidity. In certain embodiments, the ability of the compositions described herein are able to be easily resuspended and/or readily redispersed after storage for, by way of non-limiting example, 1 day, 2 days, 3 days, 1 week, 2 weeks, 3 weeks, 1 month, 3 months, 6 months, 1 year, 2 years, or the time of the shelf life.

In certain embodiments, a pharmaceutical composition described herein does not cake or aggregate during or after storage (e.g., the corticosteroid does not sediment and form a solid cake or fuse).

In some embodiments, a pharmaceutical composition described herein is a dispersion, suspension or solution. In certain embodiments, a pharmaceutical composition described herein is a solution, except that substantially all of the corticosteroid is dispersed or suspended as particles in the solution (e.g., less than about 36 μg of budesonide is in solution). In some embodiments, the at least one excipient does not enhance the solubility of the corticosteroid in the liquid vehicle.

In certain embodiments, a pharmaceutical composition described herein is a non-Newtonian fluid. In some embodiments, the non-Newtonian fluid is selected from, by way of non-limiting example, a plastic, a pseudo-plastic and a dilatant. In certain embodiments, the non-Newtonian fluid is pseudo-plastic. In some embodiments, the non-Newtonian fluid is thixotropic.

In certain embodiments, the corticosteroid is topically active (e.g., topically active on the esophageal surface). In some embodiments, the corticosteroid is budesonide. In other embodiments, the corticosteroid is fluticasone propionate. In some embodiments, the corticosteroid is a particle (e.g., a microparticle or a nanoparticle).

In certain embodiments, the additional excipient is selected from, by way of non-limiting example, maltodextrin, dextrose, hydroxyethylcellulose (HEC), hydroxypropylmethyl-cellulose (HPMC), carboxymethyl-cellulose (CMC), microcrystalline cellulose (MCC), carbomer and combinations thereof. In more specific embodiments, the at least one additional excipient comprises hydroxyethylcellulose (HEC), hydroxypropylmethyl-cellulose (HPMC), carboxymethyl-cellulose (CMC), microcrystalline cellulose (MCC), carbomer and combinations thereof, and the at least one additional excipient is present in the pharmaceutical composition in an amount of about 5 mg/mL to about 100 mg/mL. In some specific embodiments, the at least one additional excipient comprises, by way of non-limiting example, maltodextrin, dextrose and combinations thereof, and the at least one additional excipient is present in an amount of about 1 mg/mL to about 1.5 g/mL.

In certain embodiments, the liquid vehicle comprises an aqueous medium.

In some embodiments, a pharmaceutical composition described herein comprises corticosteroid particles suspended in the aqueous medium. In certain embodiments, the corticosteroid particles are microparticles having a mean diameter of, by way of non-limiting example, about 0.1 microns to about 50 microns. In some embodiments, at least 95%, at least 97%, at least 98%, or at least 99% of the corticosteroid particles are microparticles having a diameter of less than about 10 microns.

In certain embodiments, provided herein is a pharmaceutical composition wherein corticosteroid is present in an amount of about 0.01 mg/mL to about 1 mg/mL. In certain embodiments, the pharmaceutical composition has a total volume of about 1 mL to about 20 mL, about 1 mL to about 10 mL, or about 3 mL to about 7 mL, about 5 mL, or about 10 mL. In specific embodiments, a pharmaceutical composition described herein comprises about 0.25 mg to about 5 mg, about 0.3 to about 2 mg, or about 0.5 mg to about 5 mg.

In some embodiments, the at least one additional excipient comprises CMC, and the CMC is present in the pharmaceutical composition in an amount of about 5 mg/mL to about 30 mg/mL. In certain embodiments, the at least one additional excipient comprises carbomer, and the carbomer is present in the pharmaceutical composition in an amount of about 5 mg/mL to about 100 mg/mL. In some embodiments, the at least one additional excipient comprises HPMC, and the HPMC is present in the pharmaceutical composition in an amount of about 5 mg/mL to about 30 mg/mL. In certain embodiments, the at least one additional excipient comprises MCC, and the MCC is present in the pharmaceutical composition in an amount of about 5 mg/mL to about 30 mg/mL. In some embodiments, the at least one additional excipient comprises a combination of CMC and MCC, and the CMC-MCC combination is present in an amount of about 5 mg/mL to about 40 mg/mL, and wherein the CMC/MCC mixed weight ratio is about 11/89. In certain embodiments, the at least one additional agent comprises dextrose and the dextrose is present in the pharmaceutical composition in an amount of about 10 mg/mL to about 1 g/mL. In some embodiments, the at least one additional agent comprises maltodextrin and the maltodextrin is present in the pharmaceutical composition in an amount of about 10 mg/mL to about 1 g/mL.

In certain embodiments, any pharmaceutical composition described herein has a viscosity such that when a single dose of the pharmaceutical composition is orally administered to an individual, the pharmaceutical composition at least partially coats the esophagus and topically delivers a therapeutically effective amount of corticosteroid to the esophagus. In some embodiments, any pharmaceutical composition described herein has a mucoadhesive characteristic such that when a single dose of the pharmaceutical composition is orally administered to an individual, the pharmaceutical composition adheres to surface of the gastrointestinal tract (e.g., the mucosa and/or epithelium of the gastrointestinal tract or of a specific site of the gastrointestinal tract, such as the esophagus) of the individual for a time sufficient to allow topical delivery of a therapeutically effective amount of the corticosteroid to the esophagus.

In certain embodiments, provided herein is a method of treating, preventing or alleviating inflammation or symptoms associated with inflammation of the gastrointestinal tract comprising orally administering to an individual any pharmaceutical composition described herein.

In certain embodiments, a method provided herein comprises administering about 0.1 mg to about 20 mg, or about 0.3 mg to about 4 mg, or about 0.25 mg to about 5 mg of corticosteroid per day.

In certain embodiments, inflammation of the gastrointestinal tract is inflammation of the esophagus. In certain embodiments, administration of a pharmaceutical composition described herein is to an individual that has been diagnosed with eosinophilic esophagitis, an inflammatory bowel disease involving the esophagus, Crohn's disease, celiac disease, proximal gastrointestinal pathology (e.g., in individuals suffering from hypofunctioning gallbladder), eosinophilic gastrointestinal inflammation, eosinophilic duodenitis, duodenal eosinophilia, functional dyspepsia, intermediate esophagitis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, intermediate esophagitis, epithelial hyperplasia, basal cell hyperplasia, elongated papillae, dilated vessels in papillae, fungal esophagitis (e.g., Candida, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, or gastro enteritis. In specific embodiments, the individual has eosinophilic esophagitis. In some specific embodiments, the individual has been diagnosed with gastroesophageal reflux disease (GERD), nonerosive reflux disease (NERD), or erosive esophagitis. In some embodiments, the inflammation of the gastrointestinal tract is inflammation of the stomach and/or the small intestines, e.g., gastro enteritis.

In certain embodiments, the individual administered a pharmaceutical composition for the treatment, prevention or alleviation of inflammation or symptoms associated with inflammation of the gastrointestinal tract is a child or an infant. In various embodiments, the child or infant is less than 16 years old, less than 12 years old, less than 8 years old, less than 6 years old, less than 4 years old or less than 2 years old.

In some embodiments, provided herein is a kit comprising a multiple unit container and a plurality of unit doses of a pharmaceutical composition (e.g., any pharmaceutical composition described herein). In certain embodiments, each unit dose of the pharmaceutical composition comprises:
  a. a therapeutically effective amount of corticosteroid,
  b. edetate,
  c. citrate, d. polysorbate 80,
e. an optional preservative,
f. an optional flavoring agent,
g. an optional sweetener,
h. at least one additional excipient, and
i. a liquid vehicle.

In some embodiments, the at least one additional excipient comprises maltodextrin, dextrose, hydroxyethylcellulose (HEC), hydroxypropylmethyl-cellulose (HPMC), carboxymethyl-cellulose (CMC), microcrystalline cellulose (MCC), carbomer or combinations thereof.

In certain embodiments, a kit provided for herein comprises a stable pharmaceutical composition that is physically and chemically stable. In some embodiments, a kit provided for herein comprises, by way of non-limiting example, about 10 to about 60, about 14, or about 30 doses of the pharmaceutical composition. In certain embodiments, a kit provided for herein comprises, by way of non-limiting example, about 50 mL to about 500 mL, about 150 mL, about 330 mL or about 55 mL of the stable pharmaceutical composition. In some embodiments, any kit provided herein further comprises a metering device (e.g., a spoon, cup, pump, or the like) for administering the composition to an individual. In various embodiments, the metering device is incorporated into or separate from the multiple unit container.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In certain embodiments, provided herein are compositions for and methods of treating, preventing or alleviating inflammation or symptoms associated with inflammation of the gastrointestinal tract, including the esophagus, stomach and/or digestive tract. Provided herein are methods of treating, preventing or alleviating, for example, esophageal inflammation in an individual. In certain embodiments, these methods comprise orally administering to said individual a corticosteroid in association with at least one excipient.

In some embodiments, provided herein is a composition comprising a corticosteroid, dextrose, maltodextrin, edetate, citrate, polysorbate 80, an optional preservative, an optional flavoring agent, at least one additional excipient, and, a liquid vehicle. In specific embodiments, the composition comprises a preservative. In further or alternative embodiments, the composition comprises a flavoring agent. In further or alternative embodiments, the liquid vehicle is an aqueous liquid vehicle (e.g., water) or comprises an aqueous medium. In other embodiments, provided herein is a method for treating, preventing or alleviating inflammation or symptoms associated with inflammation of the gastrointestinal tract with a composition. In certain embodiments, methods provided herein comprise orally administering to an individual in need thereof a composition comprising a corticosteroid, dextrose, maltodextrin, edetate, citrate, polysorbate 80, an optional preservative, an optional flavoring agent, at least one additional excipient, and, a liquid vehicle. In specific embodiments, the composition comprises a preservative. In further or alternative embodiments, the composition comprises a flavoring agent. In further or alternative embodiments, the liquid vehicle is an aqueous medium (e.g., water). In certain embodiments, the pharmaceutical composition provided herein is stable. In specific embodiments, the pharmaceutical composition is chemically and/or physically stable.

An individual suitable for treatment with the compositions disclosed herein may, for example, have been diagnosed with a disease or condition including, but not limited to, eosinophilic esophagitis, inflammatory bowel diseases involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., Candida, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation or gastro enteritis. The composition may also be used in treating individuals diagnosed with other gastrointestinal disorders, including stomach and duodenal ulcers, hyperactive acidic discharge disorders, such as Zollinger-Ellison syndrome and laryngeal disorders. In some embodiments, the compositions or methods disclosed herein are used in methods of treating individuals diagnosed with other gastrointestinal disorders, including, by way of non-limiting example, Barrett's Esophagus, gastroesophageal reflux disease (GERD), nonerosive reflux disease (NERD), or erosive esophagitis. In some embodiments, the methods of treating, preventing or alleviating inflammation or symptoms of inflammation include methods of treating any of the gastrointestinal disorders described herein. In certain embodiments, these methods comprise orally administering to said individual a corticosteroid-containing compositions described herein.

Provided herein are methods for treating, preventing and alleviating any chronic inflammatory or malignant state that involves the gastrointestinal tract, such as the esophagus, and responds to steroid therapy. The methods and compositions of the present invention are useful, for example, for treating, preventing and alleviating inflammation and/or symptoms and associated with eosinophilic esophagitis, inflammatory bowel diseases involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., Candida, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, eosinophilic gastric outlet obstruction and related inflammation, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, Epidermolysis bullosa, post-surgery inflammation, and gastro enteritis. The present methods are also useful for treating, preventing or alleviating symptoms and/or inflammation associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application. As used herein, inflammation and/or symptoms associated with a disorder or disease disclosed herein includes inflammation and/or symptoms associated with, caused by and/or resulting from the disorder or disease. In some embodiments, provided herein is a method of reducing cytokine and/or chemokine release in the gastrointestinal tract, such as the esophagus (e.g., in the mucosa or epithelium thereof) by administering a composition described herein to the gastrointestinal tract (e.g., esophagus). In certain embodiments, provided is a method of decreasing eosinophil migration to the gastrointestinal tract (e.g., the esophagus) by administering a composition described herein to the gastrointestinal tract (e.g., the esophagus).

In specific embodiments, provided herein is a pharmaceutical composition comprising a physically and chemically stable composition comprising: (a) a therapeutically effective amount of corticosteroid; (b) edetate; (c) citrate; (d) polysorbate 80; (e) a preservative, a flavoring agent, a sweetener, or a combination thereof; (f) at least one additional excipient; and (g) a liquid vehicle. In specific embodiments, such compositions are suitable for single or multiple dose administration. In some specific embodiments, provide herein is a pharmaceutical composition comprising a physically and chemically stable composition comprising: (a) a therapeutically effective amount of corticosteroid; (b) an antioxidant; (c) a buffer; (d) a surfactant; (e) a preservative, a flavoring agent, a sweetener, or a combination thereof; (f) at least one additional excipient, and (g) a liquid vehicle. In specific embodiments, such formulations are suitable for single or multiple dose administration. In more specific embodiments, such compositions comprise a flavoring agent and/or a sweetener. In certain specific embodiments, provide herein is a pharmaceutical composition comprising a physically and chemically stable composition comprising: (a) a therapeutically effective amount of corticosteroid; (b) an optional antioxidant; (c) an optional buffer; (d) an optional surfactant; (e) an optional preservative; (f) an optional flavoring agent; (g) an optional sweetener; (h) at least one additional excipient, and (g) an optional vehicle (e.g., an aqueous vehicle). In specific embodiments, such formulations are suitable for single or multiple dose administration. In more specific embodiments, such compositions comprise a flavoring agent and/or a sweetener.

As used herein, unless otherwise stated, the use of the terms "a", "an" and "the" include both singular and multiple embodiments. As used herein, the term "individual" includes any animal. In some embodiments, the animal is a mammal. In certain embodiments, the mammal is a human. In specific embodiments, the human is an adult. In other embodiments, the human is a child (e.g., a child under 12 or a child under 6). In certain embodiments, the human is an infant. As used herein, the phrase "method of treating" or "method for treating" can, in some embodiments, encompass methods of preventing, reducing the incidences of, providing prophylactic treatment, treating and alleviating. As used herein, the phrase "an effective amount" and "a therapeutically effective amount" is an amount sufficient to elicit a change in the symptoms of or inflammation associated with gastrointestinal disorders, including but not limited to esophageal inflammation, eosinophilic esophagitis, GERD, NERD, or erosive esophagitis. As used herein, the term "or" includes "and" and "or".

As used herein, the phrase "treating inflammatory diseases involving the esophagus" includes treating symptoms of such diseases and treating inflammation associated with the diseases.

It is to be understood that any composition disclosed herein or method comprising administration of a composition disclosed herein that comprises a salt or an acid includes the disclosure of the disassociated form of the salt or acid. For example, if dissolved, sodium carboxymethylcellulose may disassociate into its sodium cationic part or parts and the corresponding carboxymethylcellulose anionic part.

Methods and Compositions

In certain embodiments, the corticosteroids used in the present invention include topical steroids including, for example, budesonide or fluticasone propionate. In some embodiments, corticosteroids are selected from, by way of non-limiting example, aclometasone, amcinonide, beclomethasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumethasone, flunisolide, fluocinolone acetonide, fluocinonide, fluocortin, fluocortolone, fluorometholone, fluperolone, fluticasone, fuprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, remexolone, tixocortol, triamcinolone and ulobetasol, and combinations, pharmaceutically acceptable salts and esters thereof. In a specific embodiment, the corticosteroid is budesonide. In another embodiment, the corticosteroid is an ester of fluticasone, e.g., fluticasone propionate.

Provided herein are methods and pharmaceutical compositions for treating, preventing or alleviating the symptoms of, and inflammation associated with, inflammatory diseases of the gastrointestinal tract, including but not limited to the upper gastrointestinal tract (e.g., the esophagus).

In certain embodiments, a corticosteroid (e.g., budesonide or fluticasone propionate) that is administered in oral form, is delivered to the esophagus in an effective dose to reduce the inflammation of the esophagus.

In one aspect, an exemplary corticosteroid is budesonide, 16,17-(butylidenebis(oxy))-11,21-dihydroxy-, (11-β,16-α)-pregna-1,4-diene-3,20-dione, or fluticasone propionate, S-(fluoromethyl)6α,9-difluoro-11β-17-dihydroxy-16α-methyl-3-oxoandrosta-1,4-diene-17β-carbothioate, 17 propionate or (6α,11β,16α,17β)-6,9-Difluoro-11-hydroxy-16-methyl-3-oxo-17-(1-oxopropoxy)androsta-1,4-diene-17-carbothioic acid S-(fluoromethyl)ester.

In certain embodiments, the corticosteroid(s) utilized herein are utilized as particles (e.g., corticosteroid particles suspended or dispersed in an aqueous medium). In specific embodiments, the particles are microparticles. In some embodiments, the microparticles have a mean diameter of about 0.1 microns to about 50 microns. In specific embodiments, the microparticles have a mean diameter of about 1 micron to about 20 microns. In certain embodiments, at least 95%, at least 98%, or at least 99% of the microparticles have a diameter of less than 10 microns.

In some embodiments, a composition or formulation described herein comprises less than 50% w/w, less than 40% w/w, less than 30% w/w, less than 20% w/w, less than 10% w/w, less than 8% w/w, less than 6% w/w, less than 5% W/w, less than 4% w/w, less than 3% w/w, less than 2% w/w, or about 2% w/w, less than 1% w/w, less than 0.5% w/w, less than 0.3% w/w, less than 0.2% w/w, or about 0.2% w/w of undissolved particles. In certain embodiments, a composition or formulation described herein is substantially free of non-corticosteroid particles.

In some embodiments, the active corticosteroid described herein is substituted with another active agent. In certain embodiments, the active agent is a therapeutic agent that targets the esophagus, e.g., for treating inflammation of the esophagus, mucositis, cancer of the esophagus, infections (e.g., bacterial or fungal infections) of the esophagus, esophageal wounds and/or contusions, or the like. In some embodiments, the active agent is a therapeutic agent that is systemically absorbed through the esophagus. In specific embodiments, the therapeutic agent that is systemically absorbed through the esophagus is an agent that is degraded or loses its efficacy in some when in the stomach, e.g., a therapeutic peptide.

In certain embodiments, pharmaceutical compositions disclosed herein and used herein comprise one or more excipients and/or one or more additional active agents. Excipients useful herein include, by way of non-limiting example, mucoadhesive agents, viscosity enhancing agents, binders, fillers (e.g., corn starch), lubricants, solvents, suspension agents, flavoring agents, coloring agents, sweeteners, preservatives, antioxidants, buffering agents, humectants, chelating agents, surfactants, and the like. As used herein, a mucoadhesive agent is an agent that adheres to a gastrointestinal surface (e.g., either or both of a gastrointestinal epithelia or mucosa).

Additional excipients are as described herein and are used in any suitable amounts, e.g., as described herein. Antioxidants, buffering agents, and surfactants are used in suitable amounts. In certain embodiments, the pharmaceutical composition provided herein is stable. In specific embodiments, the pharmaceutical composition is chemically and/or physically stable.

Provided in certain embodiments herein are compositions or formulations comprising a corticosteroid (e.g., budesonide or fluticasone propionate), one or more excipient that increases the interaction of the composition with a surface of the gastrointestinal tract (e.g., an agent that enhances viscosity, mucoadhesive character, adsorption to a mucosal layer, and/or absorption of an active through the surface layer), optionally one or more binder, optionally one or more filler, optionally one or more lubricant, optionally one or more solvent, optionally one or more suspension agent, optionally one or more flavoring agent, optionally one or more coloring agent, optionally one or more sweetener, optionally one or more preservative, optionally one or more antioxidant, optionally one or more buffering agent, optionally one or more humectant, optionally one or more chelating agent, and optionally one or more surfactant. In certain instances, the surface of the gastrointestinal tract is a mucosa and/or epithelium of the gastrointestinal tract or of a specific site of the gastrointestinal tract, such as the esophagus. In some embodiments, the composition described herein is a pharmaceutical composition comprising a corticosteroid, an antioxidant, a buffering agent, a surfactant, an optional preservative, an optional flavoring agent, at least one additional excipient, and, optionally, water.

Preservatives include, by way of non-limiting example, benzalkonium chloride, cetrimide (cetyltrimethylammonium bromide), benzoic acid, benzyl alcohol, methyl-, ethyl-, propyl- and butyl-esters of para-hydroxybenzoic acid, chlorhexidine, chlorobutanol, phenylmercuric acetate, borate and nitrate, potassium sorbate, sodium benzoate, sorbic acid, thiomersal (mercurithiosalicylate), combinations thereof, or the like. Compositions and formulations described herein optionally include about 0.1% w/w to about 5% w/w, about 0.1% w/w to about 3% w/w, about 0.1% w/w to about 1% w/w, about 0.1% w/w to about 0.5% w/w, about 0.2% w/w of one or more preservative(s).

Antioxidants include, by way of non-limiting example, ascorbyl palmitate, butylated hydroxyanisole, butylated hydroxytoluene, monothioglycerol, sodium ascorbate, sodium formaldehyde sulfoxylate, sodium metabisulfite, BHT, BHA, sodium bisulfite, vitamin E or a derivative thereof, propyl gallate, edetate (EDTA) (e.g., disodium edetate), Diethylenetriaminepentaacetic acid (DTPA), Triglycollamate (NT), combinations thereof, or the like. Compositions and formulations described herein optionally include of about 0.01% w/w to about 1% w/w, about 0.01% w/w to about 0.5% w/w, about 0.01% w/w to about 0.3% w/w, or about 0.01% w/w to about 0.1% w/w one or more antioxidant(s).

Buffering agents include, by way of non-limiting example, citrate buffers (i.e., citric acid and citrate), carbonates (e.g., calcium carbonate), hydroxides (e.g., magnesium hydroxide), phosphate buffers, acetate buffers, combinations thereof, or the like.

Humectants include, by way of non-limiting example, glycerine, propylene glycol, ethylene glycol, glyceryl triacetate, polyols (e.g., sorbitol, xylitol, maltitol, polydextrose), and the like. Compositions and formulations described herein optionally include about 0.1% w/w to about 10% w/w, about 1% w/w to about 10% w/w, about 1% to about 8% w/w, or about 5% w/w of a humectant. In certain embodiments, humectants inhibit or reduce precipitation and/or crystallization of one or more component of a composition or formulation described herein (e.g., a sweetener, mucoadhesive agent or a viscosity enhancing agent).

Chelating agents include, by way of non-limiting example, edetate (EDTA) (e.g., disodium edetate), Diethylenetriaminepentaacetic acid (DTPA), Triglycollamate (NT), or the like. Compositions and formulations described herein optionally include about 0.01% w/w to about 0.5% w/w, about 0.01% w/w to about 0.3% w/w, about 0.01% w/w to about 0.1% w/w, or about 0.05% w/w of one or more chelating agent. In some embodiments, antioxidants or chelating agents (e.g., EDTA) are present in an amount of about 0.05 mg/mL to about 25 mg/mL.

In certain embodiments, sweeteners include, by way of non-limiting example, sugar, glycerin, acesulfame potassium (AceK), mono-ammonium glycyrrhizinate (e.g., Magnasweet®), sucrose, lactose, glucose, fructose, arabinose, xylose, ribose, mannose, galactose, dextrose, sorbose, sorbitol, mannitol, maltose, cellobiose, xylitol and the like. In specific embodiments, the sweetener includes glycerin, acesulfame potassium and mono-ammonium glycyrrhizinate. Sweeteners are optionally included in any suitable amount including, by way of non-limiting example, about 0.01% w/w to about 30% w/w, about 0.1% w/w to about 5% w/w, about 5% w/w to about 20% w/w, about 0.5% w/w, about 0.8% w/w, about 1% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w or about 19% w/w. In some embodiments, flavoring agents include, by way of non-limiting example, peppermint, orange, bubble gum, wintergreen, grape and cherry. Any suitable amount of flavoring agent is optionally utilized including, e.g., about 0.01% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, up to 5% w/w, up to 10% w/w, or up to 50% w/w. In certain embodiments, a composition described herein has a reduced amount of sugar sweetener (e.g., less than 20% w/w, less than 15% w/w, less than 10% w/w, less than 9% w/w, less than 8% w/w, less than 7% w/w, less than 6% w/w, less than 5% w/w, less than 4% w/w, less than 3% w/w, or less than 2% w/w) and/or a preservative to ensure stability of the composition (e.g., to reduce microbe proliferation). In specific embodiments, glycyrrhizinate such as mono-ammonium glycyrrhizinate (e.g., Magnasweet®) is present in an amount of about 0.01% w/w to about 2.95% w/w. In certain embodiments, coloring agents include yellow agents (e.g., FD&C 5 and/or 6), red agents (e.g., FD&C Red 40, Red No. 3), blue, or the like.

Surfactants include, e.g., anionic, cationic, non-ionic, or zwitterionic surfactants, such as, by way of non-limiting example, polysorbate (e.g., polysorbate 20, polysorbate 60, polysorbate 40, polysorbate 80, polysorbate 81, polysorbate 85, polysorbate 120), bile acids or their salts (e.g., sodium taurocholates, sodium deoxytaurocholates, chenodeoxycholic acid, and ursodeoxycholic acid), nonoxynol or polyoxyethylene glycol fatty acid esters, pluronic or poloxamers such as Pluronic F68, Pluronic L44, Pluronic L101, combinations thereof, or the like. In specific embodiments, the surfactant is polysorbate 80. Compositions and formulations described herein optionally include any suitable amount of surfactant, e.g., about 0.001% w/w to about 0.5% w/w, about 0.001% w/w to about 0.3% w/w, about 0.001% w/w to about 0.1% w/w, or about 0.01% w/w of one or more surfactant.

In certain embodiments, the composition described herein is a pharmaceutical composition comprising a corticosteroid, edetate, citrate, polysorbate 80, an optional preservative, an optional flavoring agent, at least one additional excipient, and, optionally, water. In more specific embodiments, the composition comprises water. In further or alternative embodiments, the at least one additional excipient is selected from cellulose (including cellulose derivatives), dextrose, one or more maltodextrin, hydroxypropylmethyl-cellulose (HPMC), carboxymethyl-cellulose (CMC) (including, e.g., sodium carboxymethyl-cellulose (NaCMC)), microcrystalline cellulose (MCC), carbomer, hydroxyethyl cellulose (HEC) and combinations thereof. In a specific embodiment, the corticosteroid is selected from budesonide, fluticasone propionate and combinations thereof. In a more specific embodiment, the corticosteroid is budesonide. In another specific embodiment, the corticosteroid is fluticasone propionate. In a further or additional embodiment, the at least one additional excipient comprises or is hydroxypropylmethyl-cellulose (HPMC). In a specific embodiment, the at least one additional excipient comprises or is carboxymethyl-cellulose (CMC) (including, e.g., sodium carboxymethyl-cellulose (NaCMC)). In a specific embodiment, the at least one additional excipient comprises or is microcrystalline cellulose (MCC). In a specific embodiment, the at least one additional excipient comprises or is carbomer (i.e., a high molecular weight cross-linked polyacrylic acid). In a specific embodiment, the at least one additional excipient comprises or is a combination of CMC and MCC.

In specific embodiments, an excipient that increases the interaction of the composition with a surface of the gastrointestinal tract (e.g., the mucosa and/or epithelium of the gastrointestinal tract or of a specific site of the gastrointestinal tract, such as the esophagus) utilized in any composition or formulation described herein comprises at least one maltodextrin. In certain embodiments, the excipient that increases the interaction of the composition with a surface of the gastrointestinal tract (e.g., maltodextrin) is substantially or at least partially dissolved in a liquid vehicle. In some embodiments, any composition or formulation described herein comprises a first excipient that increases the interaction of the composition with a surface of the gastrointestinal tract (e.g., maltodextrin) that is substantially or at least partially dissolved in a liquid vehicle (or substantially soluble in saliva when orally administered) and a second excipient that increases the interaction of the composition with a surface of the gastrointestinal tract that is substantially insoluble in a liquid vehicle (or in saliva when orally administered). In some embodiments, an oral pharmaceutical composition described herein comprises less than about 0.1 g or less than about 1 g of maltodextrin for every mL of liquid vehicle in the oral pharmaceutical composition. In certain instances, a composition or formulation described herein comprises less than 2 g of maltodextrin/mL of composition, less than 1.5 g of maltodextrin/mL of composition, less than 1 g of maltodextrin/mL of composition, less than 0.5 g of maltodextrin/mL of composition, less than 0.25 g/mL of maltodextrin/mL of composition, about 0.05 g of maltodextrin/mL of composition to about 0.5 g of maltodextrin/mL of composition, about 0.05 g of maltodextrin/mL of composition to about 0.4 g of maltodextrin/mL of composition, about 0.05 g of maltodextrin/mL of composition to about 0.3 g of maltodextrin/mL of composition, about 0.1 g of maltodextrin/mL of composition to about 0.5 g of maltodextrin/mL of composition, about 0.1 g of maltodextrin/mL of composition to about 0.4 g of maltodextrin/mL of composition, about 0.1 g of maltodextrin/mL of composition to about 0.3 g of maltodextrin/mL of composition, about 0.2 g of maltodextrin/mL of composition to about 0.5 g of maltodextrin/mL of composition, about 0.2 g of maltodextrin/mL of composition to about 0.4 g of maltodextrin/mL of composition, or about 0.2 g of maltodextrin/mL of composition to about 0.3 g of maltodextrin/mL of composition. In some embodiments, any composition or formulation described herein comprises greater than about 7% w/w, greater than about 8% w/w, greater than about 9% w/w, greater than about 10% w/w, greater than about 11% w/w, greater than about 12% w/w, greater than about 13% w/w, greater than about 14% w/w, greater than about 15% w/w, greater than about 16% w/w, greater than about 17% w/w, greater than about 18% w/w, greater than about 19% w/w, greater than about 20% w/w, greater than about 21% w/w, greater than about 22% w/w, greater than about 23% w/w, greater than about 24% w/w, greater than about 25% w/w, greater than about 26% w/w, greater than about 27% w/w, greater than about 28% w/w, greater than about 29% w/w or greater than about 30% w/w of maltodextrin. In some embodiments, the maltodextrin is substantially dissolved in the liquid vehicle. In certain embodiments, the maltodextrin has a dextrose equivalents (DE) of greater than 4, greater than 5, greater than 10, greater than 11, greater than 12, greater than 13, greater than 14, greater than 15, about 15, about 4 to about 10, about 4 to about 9, about 4 to about 8, about 4 to about 7 (e.g., M150), about 11 to about 20, about 12 to about 19, about 13 to about 18, about 13 to about 17 (e.g., M440), or about 14 to about 16. In some embodiments, a composition described herein comprises a first maltodextrin and a second maltodextrin. In specific embodiments, the first maltodextrin has a DE of about 4 to about 10, about 4 to about 9, or about 4 to about 8 and the second maltodextrin has a DE of about 10 to about 20, about 12 to about 19, or about 13 to about 18. In some embodiments, at least one maltodextrin utilized in a composition described herein has a molecular weight high enough to increase the solubility of a corticosteroid, or to increase the suspendability of a corticosteroid particle.

As used herein, "edetate" includes all compounds of Formula I wherein each R is independently selected from an H and a negative charge (e.g., as a salt or as a disassociated salt or acid). In certain embodiments, edetate is selected from, by way of non-limiting example, disodium edetate, calcium edetate, ethylenediaminetetraacetic acid and the like.

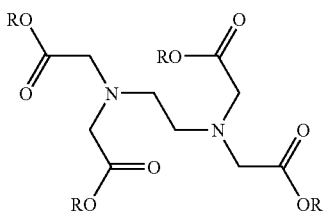

Formula I

As used herein, "citrate" includes all compounds of Formula II wherein each R is independently selected from an H and a negative charge (e.g., as a salt or as a disassociated salt or acid). In certain embodiments, citrate is selected from, by way of non-limiting example, sodium citrate, citric acid and the like.

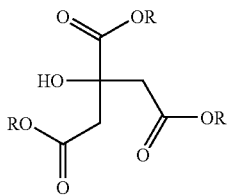

Formula II

In certain embodiments, sweeteners include, by way of non-limiting example, sucrose, lactose, glucose, fructose, arabinose, xylose, ribose, mannose, galactose, dextrose, sorbose, sorbitol, mannitol, maltose, cellobiose, xylitol and the like. In some embodiments, flavoring agents include, by way of non-limiting example, peppermint, orange, bubble gum, wintergreen, grape and cherry.

Preservatives include, by way of non-limiting example, benzalkonium chloride, methylparaben (e.g., sodium methylparaben), propylparaben, potassium sorbate and sodium benzoate. In specific embodiments, the preservative is potassium sorbate.

In certain embodiments, a composition provided herein comprises or is prepared by combining the components set forth in any of Tables 1-13. In various embodiments, one or more of maltodextrin, dextrose, HEC, CMC, MCC, Carbomer and HPMC are utilized therein. The compositions are optionally prepared in any volume (e.g., any volume described herein) comprising the components in a ratio as described in of Tables 1-13.

TABLE 1

Budesonide Composition #1

| Ingredient | Amount |
|---|---|
| Budesonide | 1 mg to 150 mg |
| CMC, MCC, Carbomer, HPMC and/or HEC | 0.5 g to 10 g |
| Dextrose | 0 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 2

Budesonide Composition #2

| Ingredient | Amount |
|---|---|
| Budesonide | 1 mg to 150 mg |
| CMC, MCC, Carbomer, HPMC and/or HEC | 0 g to 10 g |
| Dextrose | 1 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 3

Budesonide Composition #3

| Ingredient | Amount |
|---|---|
| Budesonide | 1 mg to 150 mg |
| CMC, MCC, Carbomer, HPMC and/or HEC | 0 g to 10 g |
| Dextrose | 0 g to 100 g |
| Maltodextrin | 1 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 4

Budesonide Composition #4

| Ingredient | Amount |
|---|---|
| Budesonide | 0.5 mg to 2 mg |
| CMC and MCC (e.g., Avicel RC-591) | 0.01 g to 0.3 g |
| Dextrose | 0.1 g to 1 g |
| Maltodextrin | 0.5 g to 2 g |
| EDTA (e.g., disodium edetate) | 1 mg to 10 mg |
| Citric Acid | 0.1 mg to 100 mg |
| Citrate (e.g., sodium citrate) | 0.1 mg to 200 mg |
| Polysorbate 80 (e.g., Tween 80) | 0.1 mg to 10 mg |
| Cherry Flavor | 1 mg to 100 mg |
| Sweetener | 100 mg to 1 g |

TABLE 4-continued

Budesonide Composition #4

| Ingredient | Amount |
| --- | --- |
| Sodium Benzoate | 1 mg to 50 mg |
| Potassium Sorbate | 1 mg to 50 mg |
| Water | q.s. to 5 mL |

TABLE 5

Budesonide Composition #5

| Ingredient | Amount |
| --- | --- |
| Budesonide | 0.5 mg to 2 mg |
| CMC and MCC (e.g., Avicel RC-591) | 0.02 g to 0.6 g |
| Dextrose | 0.2 g to 2 g |
| Maltodextrin | 1 g to 4 g |
| EDTA (e.g., disodium edetate) | 2 mg to 20 mg |
| Citric Acid | 0.2 mg to 200 mg |
| Citrate (e.g., sodium citrate) | 0.2 mg to 400 mg |
| Polysorbate 80 (e.g., Tween 80) | 0.2 mg to 20 mg |
| Cherry Flavor | 2 mg to 200 mg |
| Sweetener | 200 mg to 2 g |
| Sodium Benzoate | 2 mg to 100 mg |
| Potassium Sorbate | 2 mg to 100 mg |
| Water | q.s. to 10 mL |

TABLE 6

Budesonide Composition #6

| Ingredient | Amount (mg/mL) |
| --- | --- |
| Budesonide | 0.01 to 0.5 |
| CMC and MCC (e.g., Avicel RC-591) | 2 to 100 |
| Dextrose | 10 to 500 |
| Maltodextrin (M150) | 10 to 500 |
| EDTA (e.g., disodium edetate) | 0.01 to 10 |
| Citric acid | 0.1 to 10 |
| Citrate (e.g., sodium citrate) | 0.1 to 10 |
| Polysorbate 80 (e.g., Tween 80) | 0.01 to 1 |
| Flavoring agent (e.g., Cherry Flavor) | 0.1 to 100 |
| Glycerin | 10 to 100 |
| Acesulfame potassium | 0.1 to 40 |
| Magnasweet 110 | 0.1 to 40 |
| Sodium Benzoate | 0.1 to 10 |
| Potassium Sorbate | 0.1 to 10 |
| Water | q.s. to 1-15 mL |

TABLE 7

Budesonide Composition #7

| Ingredient | Amount (mg/mL) |
| --- | --- |
| Budesonide | about 0.05 to about 0.2 |
| CMC and MCC (e.g., Avicel RC-591) | 5 to 50 |
| Dextrose | 50 to 250 |
| Maltodextrin (M150) | 200 to 500 |
| EDTA (e.g., disodium edetate) | 0.1 to 1 |
| Citric acid | 0.5 to 5 |
| Citrate (e.g., sodium citrate) | 0.2 to 2 |
| Polysorbate 80 (e.g., Tween 80) | 0.01 to 0.4 |
| Flavoring agent (e.g., Cherry Flavor) | 1 to 10 |
| Glycerin | 30 to 80 |
| Acesulfame potassium | 1 to 10 |
| Magnasweet 110 | 1 to 10 |
| Sodium Benzoate | 0.5 to 4 |
| Potassium Sorbate | 0.5 to 4 |
| Water | q.s. to 1-15 mL |

TABLE 8

Budesonide Composition #8

| Ingredient | Amount (mg/mL) | Amount % w/w |
| --- | --- | --- |
| Budesonide | 0.05 | 0.004 |
| Avicel RC-591 | 23.6 | 2 |
| Dextrose | 118.0 | 10 |
| Maltodextrin (M150) | 306.8 | 26 |
| Disodium edetate | 0.59 | 0.05 |
| Citric acid | 1.77 | 0.15 |
| Sodium citrate | 0.59 | 0.05 |
| Polysorbate 80 | 0.12 | 0.01 |
| Cherry Flavor | 5.9 | 0.5 |
| Glycerin | 59.0 | 5 |
| Acesulfame potassium | 5.9 | 0.5 |
| Magnasweet 110 | 5.9 | 0.5 |
| Sodium Benzoate | 2.36 | 0.2 |
| Potassium Sorbate | 2.36 | 0.2 |
| Water | q.s. to 1, 2, 3, 4, 5, 6, 7, 8, 9, 10, 11, 12, 13, 14, or 15 mL | q.s. to 1, 2, 3, 4, 5, 6, 7, 8, 9, 10, 11, 12, 13, 14, or 15 mL |

TABLE 9

Budesonide Composition #9

| Ingredient | Amount (mg/mL) | Amount % w/w |
| --- | --- | --- |
| Budesonide | 0.2 | 0.17 |
| Avicel RC-591 | 23.6 | 2 |
| Dextrose | 118 | 10 |
| Maltodextrin (M150) | 306.8 | 26 |
| Disodium edetate | 0.59 | 0.05 |
| Citric acid | 1.77 | 0.15 |
| Sodium citrate | 0.59 | 0.05 |
| Polysorbate 80 | 0.12 | 0.01 |
| Cherry Flavor | 5.9 | 0.5 |
| Glycerin | 59 | 5 |
| Acesulfame potassium | 5.9 | 0.5 |
| Magnasweet 110 | 5.9 | 0.5 |
| Sodium Benzoate | 2.36 | 0.2 |
| Potassium Sorbate | 2.36 | 0.2 |
| Water | q.s. to 1, 2, 3, 4, 5, 6, 7, 8, 9, 10, 11, 12, 13, 14, or 15 mL | q.s. to 1, 2, 3, 4, 5, 6, 7, 8, 9, 10, 11, 12, 13, 14, or 15 mL |

TABLE 10

Fluticasone Propionate Composition #1

| Ingredient | Amount |
| --- | --- |
| Fluticasone Propionate | 0.5 mg to 150 mg |
| CMC, MCC, Carbomer, HPMC and/or HEC | 0.5 g to 10 g |
| Dextrose | 0 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 11

Fluticasone Propionate Composition #2

| Ingredient | Amount |
| --- | --- |
| Fluticasone Propionate | 0.5 mg to 150 mg |
| CMC, MCC, Carbomer, HPMC and/or | 0 g to 10 g |

TABLE 11-continued

Fluticasone Propionate Composition #2

| Ingredient | Amount |
| --- | --- |
| HEC | |
| Dextrose | 1 g to 100 g |
| Maltodextrin | 0 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 12

Fluticasone Propionate Composition #3

| Ingredient | Amount |
| --- | --- |
| Fluticasone Propionate | 0.5 mg to 150 mg |
| CMC, MCC, Carbomer, HPMC and/or HEC | 0 g to 10 g |
| Dextrose | 0 g to 100 g |
| Maltodextrin | 1 g to 100 g |
| EDTA (e.g., disodium edetate) | 5 mg to 200 mg |
| Citric Acid | 10 mg to 1 g |
| Citrate (e.g., sodium citrate) | 10 mg to 2 g |
| Polysorbate 80 (e.g., Tween 80) | 5 mg to 100 mg |
| Flavoring Agent | optional |
| Sweetener | optional |
| Preservative | optional |
| Water | q.s. to 100 mL |

TABLE 13

Corticosteroid Composition

| Ingredient | Amount % w/w |
| --- | --- |
| Corticosteroid | 0.001 to 1 |
| Sodium methylparaben | 0.0001 to 0.1 |
| Sorbitol | 5 to 30 |
| Sucrose | 1 to 40 |
| Corn starch | 1 to 10 |
| MCC | 0.1 to 5 |
| CMC (NaCMC) | 0.1 to 5 |
| Xanthan | 0.001 to 1 |
| Glycerin | 0.1 to 10 |
| Calcium carbonate | 0 to 30 |
| Magnesium hydroxide | 0 to 5 |
| Color (e.g., FD&C Red No. 3) | optional |
| Water | q.s. to 1, 2, 3, 4, 5, 6, 7, 8, 9, 10, 11, 12, 13, 14, or 15 mL |

In some embodiments, any pharmaceutical composition described herein is stable. In specific embodiments, the pharmaceutical composition is chemically and physically stable. In certain embodiments, chemical stability is evidenced by a pharmaceutical composition that comprises at least 80%, 90%, 95%, 98%, or 99% of the initial amount or label amount of corticosteroid therein for, by way of non-limiting example, 1 week, 2 weeks, 3 weeks, 1 month, 3 months, 6 months, 1 year, 2 years, or for the duration of the shelf life. In some embodiments, physical stability is evidenced by a pharmaceutical composition that is able to substantially obtain uniformity, remain substantially uniform (e.g., for at least 1 day, 3 days, 1 week, 2 weeks, 3 weeks, 1 month, 3 months, 6 months, 1 year, 2 years, etc.), or substantially regain uniformity (e.g., via mild or moderate agitation after being undisturbed for 1 day, 3 days, 1 week, 2 weeks, 3 weeks, 1 month, 3 months, 6 months, 1 year, 2 years, etc.). In certain embodiments, physical stability is evidenced by a composition that comprises at least 80%, 90%, 95%, 98%, or 99% of the initial amount or label amount of corticosteroid and/or optional additional active agent therein for, by way of non-limiting example, 2 days, 1 week, 2 weeks, 3 weeks, 1 month, 3 months, 6 months, 1 year, 2 years, or for the duration of the shelf life. In certain embodiments, uniformity as described herein is evidenced by the uniformity of the dispersion of the corticosteroid particles throughout the pharmaceutical composition, the uniformity of the dispersed mass of corticosteroid throughout the pharmaceutical composition, the uniformity of the concentration of one or more of the components in the composition throughout the pharmaceutical composition, and the like. In certain embodiments, mild or moderate agitation includes, by way of non-limiting example, shaking, shaking well, swirling, gentle swirling, and the like. In some embodiments, mild or moderate agitation includes agitation without a special apparatus. In some embodiments, uniformity of the pharmaceutical composition refers to dose uniformity (e.g., each dose delivered or withdrawn from the composition comprises a substantially similar amount of corticosteroid), or the concentration of corticosteroid in at least some or all of the doses from the multiple dose formulations are substantially similar. In certain embodiments, substantially similar includes, e.g., within 20%, 15%, 10%, 7%, 5%, 3%, 2%, or 1%.

In some embodiments, a pharmaceutical composition described herein comprises a corticosteroid that is readily dispersed throughout the composition upon agitation (e.g., mild or moderate). In certain embodiments, a pharmaceutical composition described herein comprises a corticosteroid that is readily dispersed throughout the composition upon mild or moderate agitation after storage. In some embodiments, a pharmaceutical composition described herein comprises a corticosteroid that is easily resuspended in the composition upon mild or moderate agitation. In certain embodiments, a pharmaceutical composition described herein comprises a corticosteroid that is easily resuspended in the composition upon mild or moderate agitation after storage. In some embodiments, a pharmaceutical composition described herein comprises a corticosteroid that is readily dispersed throughout the composition upon mild or moderate agitation. In certain embodiments, a pharmaceutical composition described herein comprises a corticosteroid that is readily dispersed throughout the composition upon mild or moderate agitation after storage. In certain embodiments, the ability of the compositions described herein are able to be easily resuspended and/or readily redispersed after storage under ambient conditions. In other embodiments, the storage is under an inert atmosphere, increased temperature and/or increased relative humidity. In certain embodiments, the ability of the compositions described herein are able to be easily resuspended and/or readily redispersed after storage for, by way of non-limiting example, 1 day, 2 days, 3 days, 1 week, 2 weeks, 3 weeks, 1 month, 3 months, 6 months, 1 year, 2 years, or the time of the shelf life.

In some embodiments, any pharmaceutical composition described herein optionally comprises a small amount of glycine, e.g., an amount that does not result in a substantial change in viscosity of the composition.

In some embodiments, a composition described herein is retained on the esophagus, or some portion thereof, after oral administration for at least 6 seconds, for at least 12 seconds, for at least 15 seconds, for at least 30 seconds, for at least 60 seconds, for at least 90 seconds, for at least 120 seconds, for at least 3 minutes, for at least 4 minutes, for at least 5 minutes, for at least 15 minutes, or for at least 30 minutes. In certain embodiments, the composition is retained on the esophagus after oral administration for about 15 seconds to about 120 seconds, or for about 30 to about 90 seconds.

In certain embodiments, a composition described has a viscosity sufficient to deliver an effective amount of the composition to the site of gastrointestinal inflammation, e.g., the esophagus. In some embodiments, the effective amount of the composition delivered to the esophagus is an amount sufficient to coat, or partially coat, the esophagus, and deliver the composition to the affected areas, including by way of example only, the lower esophagus, the esophageal-stomach juncture, the stomach and/or the duodenum. In certain embodiments, the viscosity of the oral dosage form is such that when administered orally, it is not so thick as to cause difficulty in swallowing, cause gagging, or be unpalatable. In certain embodiments, the viscosity of the oral dosage form is a viscosity that is sufficient to provide exposure of the corticosteroid to the esophagus for a sufficient period of time such that the symptoms of and/or inflammation associated with inflammatory diseases involving the gastrointestinal tract, including the esophagus, are reduced following administration of the corticosteroid containing oral dosage form.

Viscosity may be, for example, measured at room temperature, at about 20-25 degrees Celsius, or at about 37 degrees Celsius to mimic body temperature. In various embodiments of the present invention, the viscosity of the composition described herein is any viscosity suitable for delivery of the corticosteroid to the targeted and/or inflamed portion of the gastrointestinal tract. In some embodiments, the viscosity of the composition is at least about 2 centipoise (cP), at least about 3 cP, at least about 5 cP, at least about 10 cP, at least about 15 cP, at least about 20 cP, at least about 25 cP, at least about 30 cP, at least about 35 cP, at least about 40 cP, at least about 50 cP, at least about 200 cP, or at least about 225 cP. In some embodiments, the viscosity of the composition is at least about 100 cP. In certain embodiments, the viscosity of the composition, measured at 25 degrees Celsius, is about 50 cP to about 250,000 cP, about 50 cP to about 70,000 cP, about 50 cP to about 25,000 cP, about 50 cP to about 10,000 cP, about 50 cP to about 3,000 cP, or about 50 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition may range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g., as measured with a Brookfield viscometer at 25 degrees Celsius equipped with an ultra low adapter).

In some embodiments, the viscosity of the composition is measured at room temperature (about 25 degrees C.) with a shear rate of about 13.2 sec$^{-1}$. In certain embodiments, provided herein is a composition having a viscosity under such conditions that is at least about 2 centipoise (cP), at least about 3 cP, at least about 5 cP, at least about 10 cP, at least about 15 cP, at least about 20 cP, at least about 25 cP, at least about 30 cP, at least about 35 cP, at least about 40 cP, at least about 50 cP, at least about 200 cP, at least about 225 cP, at least about 250 cP, at least about 300 cP, or at least about 400 cP. In some embodiments, the viscosity of the composition under such conditions is about 50 cP to about 250,000 cP, about 50 cP to about 70,000 cP, about 50 cP to about 25,000 cP, about 50 cP to about 10,000 cP, about 50 cP to about 3,000 cP, about 50 cP to about 2,000 cP, about 250 cP to about 250,000 cP, about 250 cP to about 70,000 cP, about 250 cP to about 25,000 cP, about 250 cP to about 10,000 cP, about 250 cP to about 3,000 cP, or about 250 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition under such conditions may range from about 100 cP to about 200 cP, about 200 cP to about 300 cP, about 250 cP to about 600 cP or about 400 cP to about 600 cP. In specific embodiments, the viscosity of the formulation measured under such conditions is about 30 cP, about 40 cP, about 100 cP, about 200 cP, about 300 cP, about 400 cP, about 500 cP, or about 250,000 cP.

In some embodiments, the viscosity of the composition is measured at room temperature (about 25 degrees C.) with a shear rate of about 15 sec$^{-1}$ (e.g., with a gap between the spindle and the sample chamber wall of about 6 mm or greater). In certain embodiments, provided herein is a composition having a viscosity under such conditions that is at least about 2 centipoise (cP), at least about 3 cP, at least about 5 cP, at least about 10 cP, at least about 15 cP, at least about 20 cP, at least about 25 cP, at least about 30 cP, at least about 50 cP, at least about 100 cP, at least about 150 centipoise (cP), at least about 160 cP, at least about 170 cP, at least about 180 cP, at least about 190 cP, or at least about 200 cP. In some embodiments, the viscosity of the composition under such conditions is about 150 cP to about 250,000 cP, 160 cP to about 250,000 cP, 170 cP to about 250,000 cP, 180 cP to about 250,000 cP, or 190 cP to about 250,000 cP.

Viscosity can also be determined by any method that will measure the resistance to shear offered by the substance or preparation. Many viscometers are available to those in the pharmaceutical field, and include those built by, for example, Brookfield.

In some embodiments, a composition or formulation described herein comprises a viscosity enhancing agent that imparts on the composition a viscosity sufficient to provide increased residence on the esophagus while also allowing migration of the active agent(s) (solute or particles) when the composition is orally administered to an individual. In other words, in some embodiments, the viscosity is high enough to increase residence time of the composition on a surface of the gastrointestinal tract (e.g., the mucosa and/or epithelium of the gastrointestinal tract or of a specific site of the gastrointestinal tract, such as the esophagus), but not so high as to prevent migration of the active agent(s) within the composition, e.g., toward the surface of the gastrointestinal tract.

An increase in the interaction of the composition with the surface of the gastrointestinal tract (e.g., esophagus) may be measured by measuring the retention time of the material along a length of a gastrointestinal surface, wherein the retention time is increased in the presence of the excipients as compared to its absence. As used herein, in certain embodiments, a gastrointestinal surface includes a gastrointestinal mucosa and/or a gastrointestinal epithelium, all of which terms are used interchangeably herein. In another embodiment, an increased interaction may be measured by the decrease in physiological manifestations or symptoms of the disease or ailment to be treated, including a decrease in total eosinophil counts in a target sample.

In some embodiments, at least 50%, 20%, 10%, 9%, 8%, 7%, 6%, 5%, 4%, 3%, 2%, or 1% of the corticosteroid or composition described herein adheres to or resides upon a surface of the gastrointestinal tract (e.g., resides in the esophagus), or some portion thereof, at least 5 seconds, at least 6 seconds, at least 10 seconds, at least 12 seconds, at least 15 seconds, at least 30 seconds, at least 60 seconds, at least 90 seconds, at least 120 seconds, at least 3 minutes, at least 4 minutes, at least 5 minutes, at least 15 minutes, or at least 30 minutes after oral administration (e.g., drinking or swallowing). In certain embodiments, at least 50%, 20%, 10%, 9%, 8%, 7%, 6%, 5%, 4%, 3%, 2%, or 1% of the corticosteroid or composition adheres to, resides upon, or is retained on the esophagus after oral administration for about 15 seconds to about 120 seconds, or for about 30 to about 90 seconds. In some embodiments, a portion of the composition comprises about 90% or more, about 80% or more, about 70% or more, about 60% or more, about 50% or more, about 40% or more, about 30% or more, about 20% or more, about 10% or more, or about 5% or more.

In certain embodiments, adherence and/or absorption of a pharmaceutical composition or corticosteroid described herein to a gastrointestinal mucosal site (e.g., esophagus) may be determined in any suitable manner, e.g., by scintigraphy or by an assay. In some embodiments, such determinations are performed in vivo or in vitro. In certain embodiments, in vivo scintigraphy may include combining a pharmaceutical composition described herein with a detectable radioisotope, administering the labeled composition to a subject and detecting and/or measuring the adherence or residence of the pharmaceutical composition or corticosteroid to the gastrointestinal surface (e.g., esophagus) with a device (e.g., camera) that detects and/or measures radioactivity. In some embodiments, in vivo scintigraphy may include linking a corticosteroid described herein with a detectable radioisotope, formulating the labeled corticosteroid into a composition described herein, administering the composition to a subject and detecting and/or measuring the adherence or residence of the pharmaceutical composition or corticosteroid to the gastrointestinal surface (e.g., esophagus) with a device (e.g., camera) that detects and/or measures radioactivity. In certain embodiments, an in vitro assay for detecting adherence of a pharmaceutical composition or corticosteroid described herein to a gastrointestinal mucosal site (e.g., esophagus) may include applying a composition described herein to a distal portion of a strip of gastrointestinal mucosal tissue (e.g., porcine esophageal tissue) and subjecting the composition to a flow of artificial saliva in the direction of the opposite distal portion of the strip. Determination of adherence or residence of the composition and/or corticosteroid may be determined at a given time by detecting either the amount of composition and/or corticosteroid eluted or the amount of composition and/or corticosteroid remaining on the gastrointestinal surface (e.g., esophagus).

In certain embodiments, a composition described has a viscosity sufficient to deliver an effective amount of the composition to the site of gastrointestinal affliction, e.g., the esophagus. In some embodiments, the effective amount of the composition delivered to the esophagus is an amount sufficient to coat, or partially coat, a surface of the gastrointestinal tract, and deliver the composition to the affected areas, including by way of example only, the esophagus, the lower esophagus, the esophageal-stomach juncture, the stomach and/or the duodenum. In certain embodiments, the viscosity of the oral dosage form is such that when administered orally, it is not so thick as to cause difficulty in swallowing, cause gagging, and/or be unpalatable. In certain embodiments, the viscosity of the oral dosage form is a viscosity that is sufficient to provide exposure of the therapeutic agent to the esophagus for a sufficient period of time such that the disorder or symptoms of the disorder involving the gastrointestinal tract, including the esophagus, are reduced following administration of a pharmaceutical composition described herein formulated in or as an oral dosage form. In some instances wherein the pharmaceutical composition is in solid or semi-solid form, the composition described has a viscosity, when mixed with saliva or water (e.g., in certain instances wherein the composition is formulated as an effervescent tablet, sachet or home brew), the resulting composition has a viscosity sufficient to deliver an effective amount of a composition described herein to the site of gastrointestinal inflammation, e.g., the esophagus.

In certain embodiments, a pharmaceutical composition described herein is a non-Newtonian fluid or a Newtonian fluid. In some embodiments, a pharmaceutical composition described herein is a non-Newtonian fluid. In specific embodiments, the non-Newtonian fluid is a plastic, pseudoplastic or dilatant non-Newtonian fluid. In some specific embodiments, the non-Newtonian fluid is thixotropic. In certain embodiments, the non-Newtonian fluid composition thins with shear, and thickens upon the absence of shear. Thus, in some embodiments, provided herein is a fluid pharmaceutical composition that is suitable for easy pouring following mild or moderate agitation. Furthermore, in some embodiments, provided herein is a fluid pharmaceutical composition that while being suitable for easy pouring following mild or moderate agitation becomes viscous enough upon oral administration to allow the pharmaceutical composition to at least partially coat the esophagus and topically deliver a therapeutically effective amount of corticosteroid to the esophagus. In some embodiments, the at least one additional excipient is selected from a non-Newtonian viscosity enhancing agent (i.e., an agent that provides a composition herein with a non-Newtonian character). Non-Newtonian viscosity enhancing agents include, by way of non-limiting example, acacia (e.g., used in about 5-10% w/w of a pharmaceutical composition described herein), alginic acid (e.g., about 0.5-20% w/w), carbomer, CaCMC, NaCMC, carrageenan (e.g., about 0.3-12% w/w), ceratonia (e.g., about 0.1-1% w/w), chitosin (e.g., about 0.5-2% w/w), colloidal silicon dioxide (e.g., about 2-10% w/w), ethylcellulose (e.g., about 5-25% w/w), gelatin, guar gum (e.g., about 1-2.5% w/w), HEC, hydroxyethylmethyl cellulose (e.g., about 1-5% w/w), hydroxypropyl cellulose (e.g., about 1-10% w/w), HPMC, magnesium aluminum silicate (e.g., about 2-10% w/w), one or more maltodextrin, methylcellulose (e.g., about 1-2% w/w), polyethylene glycol (e.g., about 45-60% w/w), povidone (e.g., about 10-15% w/w), saponite, sodium alginate (e.g., about 1-5% w/w), sucrose (e.g., about 50-70% w/w), tragacanth (e.g., about 0.1-2% w/w), xanthan gum (e.g., about 0.1-1% w/w), an combinations thereof.

A Newtonian fluid can be described as a fluid whose viscosity is equal to the shear stress exerted by the fluid divided by the velocity gradient perpendicular to the direction of the shear. In certain embodiments, the at least one additional excipient is selected from a Newtonian viscosity enhancing agent (i.e., an agent that provides a composition herein with a Newtonian character). Newtonian viscosity enhancing agents include, by way of non-limiting example, glycerin (e.g., about 50-80% w/w), polydextrose (e.g., about 50-70% w/w), and combinations thereof.

In certain embodiments, following administration of a composition described herein to a gastrointestinal surface (e.g., of a surface of the upper gastrointestinal tract, or of the esophagus), at least 1%, 2%, 3%, 4%, 5%, 6%, 7%, 8%, 9%, 10%, 15%, 20%, 30%, 40%, 50%, 60%, 70%, 80%, 90% or 95% by weight of the corticosteroid or composition administered adheres to and/or is absorbed at a gastrointestinal surface (e.g., of a surface of the upper gastrointestinal tract, or of the esophagus) after at least 0.08, 0.17, 0.25, 0.5, 0.75, 1, 1.5, 2, 3, 4, 5, 6, 7, 8, 9, 10, 15, 20, 25, 30, 35, 40, 45, 50, 55 or 60 minutes following application of the composition to the gastrointestinal surface (e.g., of a surface of the upper gastrointestinal tract, or of the esophagus). In specific embodiments, the gastrointestinal surface is the site of gastrointestinal inflammation.

In specific embodiments, following oral administration of a composition described herein to the esophagus (e.g., following initial swallowing or drinking of the composition), at least 1%, 2%, 3%, 4%, 5%, 6%, 7%, 8%, 9%, 10%, 15%, 20%, 30%, 40%, 50%, 60%, 70%, 80%, 90% or 95% by weight of the corticosteroid or composition administered is present within the esophagus (e.g., as measured by gamma scintigraphy) after at least 5 seconds, 10 seconds, 15 seconds, 20 seconds, 25 seconds, 30 seconds, 40 seconds, 45 seconds, 50 seconds, or 1, 1.5, 2, 3, 4, 5, 6, 7, 8, 9, 10, 15, 20, 25, 30, 35, 40, 45, 50, 55 or 60 minutes following application of the composition to the esophagus. In certain instances, even small differences (e.g., increases) in adherence times (e.g., residence times) between formulations can result in therapeutically significant or clinically significant results or improvements.

In some embodiments, a pharmaceutical composition described herein is sufficiently spreadable and/or has an appropriate flow characteristic on a gastrointestinal surface (e.g., on a surface of the upper gastrointestinal tract, such as the esophagus). In certain embodiments, the spreadability and/or flow characteristic of the composition is suitable so as to allow a pharmaceutical composition or a unit dose of a pharmaceutical composition described herein to spread across and/or flow upon the gastrointestinal surface and at least partially coat the gastrointestinal surface. In some embodiments, by at least partially coating the gastrointestinal surface, topical delivery of the corticosteroid to the gastrointestinal site is achieved.

In certain embodiments, the pharmaceutical compositions provided herein are used to treat, prevent or alleviate inflammation or symptoms associated with inflammation involving the gastrointestinal tract, including the esophagus, stomach and/or digestive tract. In specific embodiments, the pharmaceutical composition is in liquid form. Liquid forms include, by way of non-limiting example, solutions, suspensions, syrups, slurries, dispersions, colloids and the like. In specific embodiments, the liquid is a suspension. In some embodiments, a pharmaceutical composition described herein is in liquid, semi-solid or solid form. In specific embodiments, a pharmaceutical composition described herein is in semi-solid form, e.g., a gel, a gel matrix, a cream, a paste, or the like. In some embodiments, semi-solid forms comprise a liquid vehicle.

The methods and compositions of the present invention are used by individuals of any age. By "individual" is meant any animal, for example, a mammal, or, for example, a human, including, for example, patients in need of treatment. In some embodiments, the individual is a human adult. In other embodiments, the individual is a human child or infant. In certain embodiments, the human child or infant is less than 16 years old, less than 12 years old, less than 8 years old, less than 6 years old, less than 4 years old or less than 2 years old.

Formulations

While any of the pharmaceutical compositions, methods and kits described herein are typically used in therapy for human patients, in certain embodiments, they are used in veterinary medicine to treat similar or identical diseases. In some embodiments, the compositions are used, for example, to treat mammals, including, but not limited to, primates and domesticated mammals. In some embodiments, the compositions, methods and kits are used, for example, to treat herbivores. The compositions of the present invention include geometric and optical isomers.

Pharmaceutical compositions suitable for use in the present invention include compositions wherein the active ingredient or ingredients are contained in an effective amount to achieve its intended purpose. In certain embodiments, the pharmaceutical compositions disclosed herein comprise corticosteroid in an amount sufficient to treat, prevent or alleviate inflammation or symptoms associated with inflammation involving the gastrointestinal tract, including the esophagus.

In certain embodiments, the exact dosage of corticosteroid depends upon, by way of non-limiting example, the form in which the composition is administered, the subject to be treated, the age, body weight and/or height of the subject to be treated, and/or the preference and experience of the attending physician. Thus, in some embodiments, the dosage of corticosteroid administered may vary from those disclosed herein. In certain embodiments, the optimal concentration of the corticosteroid in the composition depends upon, by way of non-limiting example, the specific corticosteroid used, the characteristics of the patient, and/or the nature of the inflammation for which the treatment is sought. In various embodiments, these factors are determined by those of skill in the medical and pharmaceutical arts in view of the present disclosure.

Generally, a therapeutically effective dose is desired. A therapeutically effective dose refers to the amount of the corticosteroid that results in a degree of amelioration of symptoms and/or inflammation relative to the status of such symptoms and/or inflammation prior to treatment. The dosage forms and methods of applying dosage forms containing effective amounts are within the scope of the instant invention. In various embodiments, the amount of corticosteroid (e.g., budesonide or fluticasone propionate) used in a method or in a composition described herein is from about 2.5 to 400 µg/kg of body weight per day, or for example, in the range of 5 to 300 µg/kg per day, or for example in the range of 5 to 200 µg/kg per day, or for example in the range of 5 to 100 µg/kg per day, or for example in the range of 10 to 100 µg/kg per day, or for example in the range of 10-50 µg/kg per day, or for example in the range of 10-100 µg/kg/day, or for example in the range of 5-50 µg/kg/day, or in an illustrative embodiment in the range of 10-60 µg/kg/day.

In an illustrative embodiment, a dosage or amount (including a divided dose) of corticosteroid is provided in a composition of sufficient volume to allow any of the compositions disclosed herein to reach the targeted and/or inflamed portion of the gastrointestinal tract, including, e.g., the esophagus, in an effective amount. In some embodiments, the effective amount of the composition delivered to the esophagus is an amount sufficient to coat or at least partially coat the esophagus, and deliver the composition to the affected areas, including by way of example only, the lower esophagus, the esophageal-stomach juncture, the stomach and/or the duodenum. In certain embodiments, a composition described herein as a volume of, for example about 1-20 mL, or for example about 1-50 mL, or for example about 1-40 mL, or for example about 1-30 mL, or for example about 1-25 mL, or for example about 5-25 mL, or for example about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example, about 5 mL, or for example about 6-14 mL, or for example about 8-12 mL, or for example, about 9-11 mL, or for example, about 10 mL. In more specific embodiments, about 0.05 mg to about 20 mg, about 0.05 mg to about 10 mg, about 0.1 mg to about 10 mg, 0.25 mg to about 6 mg, about 0.25 mg, about 0.375 mg, about 0.5 mg, about 0.75 mg, about 1 mg, about 1.25 mg, about 1.5 mg, or about 2 mg of corticosteroid (e.g., budesonide) is formulated into a single or unit dose of a pharmaceutical composition described herein, the single or unit dose having a total volume of about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example about 5 mL, or for example about 6-14 mL, or for example about 8-12 mL, or for example, about 9-11 mL, or for example, about 10 mL. As discussed herein, "liquid" encompasses slurries, solutions, suspensions, dispersions or any combination thereof, depending on the solubilities and amounts of the individual components and the vehicles and solvents used. In some embodiments, an appropriate palatable dosage is in a volume sufficient to coat or at least partially coat the esophagus, and in an illustrative embodiment, the volume is sufficient to coat or at least partially coat the esophagus and deliver the corticosteroid to the affected areas, including by way of example only, the lower esophagus, the esophageal-stomach juncture, the stomach and/or the duodenum. The composition may be delivered, for example, four times a day, three times a day, twice a day, once a day, every other day, three times a week, twice a week, or once a week. The dosage may, for example, be divided into multiple doses throughout the day, or be provided, for example, in four, three, two, or one dose a day. In certain instances, administration more frequent administration (e.g., b.i.d. versus once a day) provides for a shorter overall therapy or a quicker onset of symptom resolution. In one illustrative example, the dose is provided once a day.

In certain embodiments, a dose or composition described herein is administered with food. In some embodiments, a dose or composition described herein is administered without food. In certain embodiments, a dose or composition described herein is administered in a fed or fasted state. In some embodiments, a dose or composition described herein is administered in the morning, in the afternoon, in the evening, at night, or a combination thereof. In some embodiments, the dose is administered at night. In another aspect, the dose is administered about 30 minutes prior to bed, with no food or water given after administration of the compositions herein. In yet another embodiment of the instant invention, the dose is administered prior to bedtime, wherein after administration of the composition, the patient or individual is in a substantially supine position for at least 30 minutes, at least 1 hour, at least 2 hours, at least 4 hours or at least 8 hours.

In some embodiments, provided herein are methods of treating, preventing, or alleviating inflammation or symptoms associated with inflammation of the gastrointestinal tract, e.g., the esophagus, comprising administering to an individual in need thereof a single unit dose of a pharmaceutical composition described herein from a multidose container. In specific embodiments, administering a single unit dose from a multi dose container comprises (1) shaking a multidose container, the multidose container comprising at least one unit dose of a pharmaceutical composition described herein; (2) pouring (or otherwise dispensing) a single unit dose from the multidose container into an administration device (e.g., a device suitable for administering to a human individual, such as a spoon, cup or syringe); and (3) administering the single unit dose to the individual in need thereof. In more specific embodiments, shaking of the multidose container occurs until the fluid therein has a viscosity suitable for pouring (e.g., easy pouring). In some specific embodiments, the process further comprises waiting after pouring the single unit dose and prior to administering the single unit dose to the individual in need thereof. In specific embodiments, the wait time is a time sufficient to allow the viscosity of composition to achieve a desired level, e.g., a viscosity to improve the coating capabilities of the composition. In some embodiments, the wait time is, e.g., about 3 seconds, or more; about 5 seconds, or more; about 10 seconds, or more; about 15 seconds, or more; about 20 seconds, or more; about 25 seconds, or more; about 30 seconds, or more; about 40 seconds, or more; about 45 seconds, or more; about 50 seconds, or more; or about 60 seconds, or more. In other specific embodiments, the composition is administered immediately following pouring the composition into the administration device. In some embodiments, the process comprises shaking the multidose container well.

In some embodiments, initial treatment continues, for example, for about 3 days to 2 weeks for an acute condition, or about 4 weeks to about 16 weeks for a chronic condition, or about 8 weeks to about 12 weeks for a chronic condition. In various embodiments, longer therapy is needed, such as, for example, therapy similar to chronic therapy for persistent asthma. In some aspects of the present invention, patients are, for example, be treated for up to 6 months, or up to one year. In certain aspects, maintenance treatments last up to or longer than one year. In some embodiments, patients are treated on a maintenance basis or on an as needed basis during a problematic episode, depending on the severity of the condition. In certain embodiments, patients are treated on a rotating treatment basis, where treatment is provided for a period of time and then the patient is taken off of the drug for a period before treatment resumes again. When off the drug, the patient may be given no treatment, treatment with another medication, dietary therapy, or treatment with a reduced dosage. In certain embodiments, patients are given treatment with a higher dose of the composition until a desired reduced disease state is achieved, and then continued on a lower dose of the composition. In certain embodiments, a patient combines treatment with a composition described herein with a treatment with another medication, and/or dietary therapy. In certain embodiments, patients are given treatment with a higher dose of the composition until a desired reduced disease state is achieved, and then continued on a lower dose of the composition.

In some embodiments, methods of treatment described herein include intermittent or continuous treatments. In certain embodiments, a method of treating gastrointestinal inflammation described herein includes prophylactic treatment of gastrointestinal inflammation (e.g., a treatment that prevents symptoms and/or inflammation from occurring). In some embodiments, a method of treating gastrointestinal inflammation described herein includes a method of prolonging and/or maintaining remission of gastrointestinal inflammation by administering or continuing to administer a pharmaceutical composition as described herein after inflammation and/or symptoms of inflammation are in remission. In specific embodiments, prophylactic and/or remissive therapies optionally comprise administration of a composition described herein comprising a reduced amount of corticosteroid compared to the amount of corticosteroid utilized when the inflammation and/or symptoms of inflammation are not in remission.

In some embodiments, provided herein is a method of diagnosing an individual with gastrointestinal inflammation (e.g., EoE) by administering a pharmaceutical composition described herein; and determining the efficacy of such a treatment. In certain instances, the individual is a patient who has gastrointestinal inflammation and/or symptoms thereof that are refractory to at least one acid inhibitor (e.g., PPI and/or H2A). In some embodiments, effective treatment of the gastrointestinal inflammation with a composition described herein is a positive indication of EoE. In certain embodiments, this method of diagnosis is used instead of an esophageal biopsy.

In some embodiments, the corticosteroid is present in a pharmaceutical composition described herein in any effective amount. In some embodiments, an effective amount is an amount sufficient to reduce inflammation or symptoms of inflammation associated with an inflammatory disease or condition of the gastrointestinal tract (e.g., the esophagus) as compared to the level of inflammation or symptoms of inflammation associated with an inflammatory disease prior to administration of the effective amount. In certain embodiments, effective amount is an amount sufficient to maintain a reduction in inflammation or symptoms of inflammation achieved in any manner including, but not limited to, by the administration of an effective amount sufficient to achieve such a reduction. In some embodiments, the effective amount is about 50 µg to about 500 mg, about 50 µg to about 200 mg, about 50 µg to about 100 mg, about 50 µg to about 50 mg, about 250 µg to about 20 mg, about 250 µg to about 15 mg, about 250 µg to about 10 mg, about 0.05 mg to about 20 mg, about 0.1 mg to about 20 mg, about 0.05 mg to about 15 mg, about 0.05 mg to about 10 mg, about 0.05 mg to about 7.5 mg, about 0.05 mg to about 5 mg, about 0.3 mg to about 4 mg, about 0.3 mg to about 2 mg, about 0.25 mg to about 3 mg, about 0.25 mg to about 2.5 mg, about 0.5 mg to about 3 mg, about 0.5 mg to about 2 mg, about 0.5 mg to about 0.1 mg, about 0.5 mg to about 5 mg, about 0.5 mg to about 4 mg, about 1 mg to about 4 mg, about 1 mg to about 3 mg, about 2 mg to about 3 mg, or about 2 mg to about 4 mg. In specific embodiments, the effective amount of corticosteroid is about 0.05 mg, about 0.1 mg., about 0.15 mg., about 0.25 mg., about 0.3 mg., about 0.35 mg, about 0.4 mg, about 0.37 mg, about 0.375 mg, about 0.7 mg, about 0.8 mg, about 0.75 mg, about 1 mg, about 1.2 mg, about 1.25 mg, about 1.3 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, or about 7.5 mg or more. In certain embodiments, the corticosteroid is present in a pharmaceutical composition at a concentration of about 0.01 mg/mL to about 2 mg/mL of composition. In specific embodiments, the corticosteroid is present in a pharmaceutical composition at a concentration of about 0.01 mg/mL to about 1.5 mg/mL, about 0.02 mg/mL to about 1.5 mg/mL, about 0.04 mg/mL to about 1.5 mg/mL, about 0.03 mg/mL to about 1.5 mg/mL, about 0.05 mg/mL to about 1.5 mg/mL, or about 0.07 mg/mL to about 1.5 mg/mL. In more specific embodiments, the corticosteroid is present in a pharmaceutical composition at a concentration of about 0.07 mg/mL to about 1 mg/mL.

In some embodiments, a composition described herein comprises a corticosteroid (e.g., budesonide or fluticasone propionate), one or more excipient that increases the interaction of the composition with a surface of the gastrointestinal tract (e.g., an agent that enhances viscosity, mucoadhesive character, adsorption to a surface of the gastrointestinal tract, and/or absorption of an active through a surface of the gastrointestinal tract), optionally one or more binder, optionally one or more filler, optionally one or more lubricant, optionally one or more solvent (or vehicle), optionally one or more suspension agent, optionally one or more flavoring agent, optionally one or more coloring agent, optionally one or more sweetener, optionally one or more preservative, optionally one or more antioxidant, optionally one or more buffering agent, optionally one or more humectant, optionally one or more chelating agent, and optionally one or more surfactant. In specific embodiments, the composition described herein is a composition comprising a corticosteroid, dextrose, maltodextrin, edetate, citrate, polysorbate 80, an optional preservative, an optional flavoring agent, an optional sweetener, at least one additional excipient, and a liquid vehicle. In specific embodiments, the composition comprises a preservative. In further or alternative embodiments, the composition comprises a flavoring agent. In further or alternative embodiments, the liquid vehicle is an aqueous medium (e.g., water). In specific embodiments, corticosteroid particles (e.g., microparticles) are suspended in the aqueous medium.

In some embodiments, the corticosteroid is selected from, by way of non-limiting example, budesonide, fluticasone propionate and combinations thereof. In specific embodiments, corticosteroid is present in the composition in an amount of about 0.01 mg/mL to about 3 mg/mL, about 0.01 mg/mL to about 2 mg/mL, about 0.01 mg/mL to about 1.5 mg/mL, about 0.07 mg/mL to about 1.5 mg/mL, or about 0.07 mg/mL to about 1 mg/mL. In more specific embodiments, budesonide is present in an amount of about 0.01 mg/mL to about 3 mg/mL, about 0.01 mg/mL to about 1.5 mg/mL, or about 0.07 mg/mL to about 1 mg/mL. In other specific embodiments, fluticasone propionate is present in an amount of about 0.005 mg/mL to about 1.5 mg/mL, or about 0.01 mg/mL to about 1 mg/mL.

In some embodiments, the volume of a composition or dose of a composition described herein is an amount sufficient to substantially coat (e.g., at least 50%, at least 60%, at least 70%, at least 80%, at least 90%, at least 95%, at least 98% or at least 99% of) the length of the esophagus of an individual to whom the composition is administered. In certain embodiments, the volume of a composition or a dose of a composition described herein is about 0.05 mL/cm esophageal length to about 1 mL/cm esophageal length, about 0.1 mL/cm esophageal length to about 0.8 mL/cm esophageal length, about 0.2 mL/cm esophageal length to about 0.6 mL/cm esophageal length, or about 0.3 mL/cm esophageal length to about 0.5 mL/cm esophageal length, wherein the esophageal length is the esophageal length of the individual to whom the composition is administered. In some embodiments, the volume of a composition or dose of a composition described herein is based on the esophageal length of an individual (e.g., male, female, or both) that is in the $50^{th}$ percentile of height for their age. Therefore, in some embodiments, the volume of a composition or dose of a composition described herein is about 0.05 mL/cm esophageal length to about 1 mL/cm esophageal length, about 0.1 mL/cm esophageal length to about 0.8 mL/cm esophageal length, about 0.2 mL/cm esophageal length to about 0.6 mL/cm esophageal length, about 0.3 mL/cm esophageal length to about 0.5 mL/cm esophageal length, about 0.32 mL/cm esophageal length to about 0.41 mL/cm esophageal length, or about 0.3 mL/cm esophageal length to about 0.46 mL/cm esophageal length, wherein the esophageal length is the esophageal length of an individual having a height in the $50^{th}$ percentile for the age of the individual to whom the composition is administered. In certain instances, esophageal length is the actual esophageal length of the individual or is calculated based on the equation: esophageal length=1.048 (cm)+(0.167*height(cm)). In certain instances, for example, the $50^{th}$ percentile height (CDC 2000) for male children age 2 is 87 cm, age 3 is 95 cm, age 4 is 102 cm, age 5 is 109 cm, age 6 is 115 cm, age 7 is 122 cm, age 8 is 128 cm, age 9 is 134 cm, age 10 is 139 cm, age 11 is 144 cm, age 12 is 149 cm, age 13 is 156 cm, age 14 is 164 cm, age 15 is 170 cm, age 16 is 174 cm, age 17 is 175 cm, and age 18 is 176 cm.

Furthermore, in certain embodiments, the amount of a therapeutic agent (e.g., a corticosteroid such as budesonide) in a composition or a dose of a composition described herein is about 0.005 mg/cm esophageal length to about 0.3 mg/cm esophageal length, about 0.008 mg/cm esophageal length to about 0.2 mg/cm esophageal length, about 0.01 mg/cm esophageal length to about 0.15 mg/cm esophageal length, or about 0.015 mg/cm esophageal length to about 0.1 mg/cm esophageal length, wherein the esophageal length is the esophageal length of the individual to whom the composition is administered. In some embodiments, the volume of a composition or dose of a composition described herein is based on the esophageal length of an individual (e.g., male, female, or both) that is in the $50^{th}$ percentile of height for their age. Therefore, in some embodiments, the amount of a therapeutic agent (e.g., a corticosteroid such as budesonide) in a composition or dose of a composition described herein is about 0.005 mg/cm esophageal length to about 0.3 mg/cm esophageal length, about 0.008 mg/cm esophageal length to about 0.2 mg/cm esophageal length, about 0.01 mg/cm esophageal length to about 0.15 mg/cm esophageal length, or about 0.015 mg/cm esophageal length to about 0.1 mg/cm esophageal length, wherein the esophageal length is the esophageal length of an individual having a height in the $50^{th}$ percentile for the age of the individual to whom the composition is administered.

In some embodiments, any pharmaceutical composition or dose of a pharmaceutical composition described herein is provided or administered in a volume sufficient to provide a bolus when orally administered to an individual. In certain embodiments, the composition has a volume that does not systemically deliver excessive amounts of the active agent. In some embodiments, the pharmaceutical composition or dose is provided in a volume sufficient to provide a bolus when administered to an individual, wherein the size of the bolus at the distal end of the esophagus (e.g., the size of the bolus prior, e.g., immediately prior, to entering or passing the lower esophageal sphincter) is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10% or less than 5% of size of the bolus that entered the esophagus (e.g., the size of the bolus after, e.g., immediately after, passing the upper esophageal sphincter). In some embodiments, the size of the bolus is determined as a measure of diameter or of volume. In certain embodiments, diameter of the sphincter can be determined using gamma scintigraphy techniques. In specific embodiments, the volume of the composition or dose is adjusted given the length and/or diameter of the esophagus of the individual to whom the composition or dose is administered.

In some embodiments, the at least one additional excipient comprises or is HPMC. In specific embodiments, HPMC is present in the composition in an amount of about 1 mg/mL to about 100 mg/mL, about 30 mg/mL to about 70 mg/mL or about 5 mg/mL to about 50 mg/mL. In some embodiments, the at least one additional excipient comprises or is CMC. In specific embodiments, CMC is present in the composition in an amount of about 1 mg/mL to about 100 mg/mL, about 30 mg/mL to about 70 mg/mL or about 5 mg/mL to about 50 mg/mL. In some embodiments, the at least one additional excipient comprises or is MCC. In specific embodiments, MCC is present in the composition in an amount of about 1 mg/mL to about 100 mg/mL, about 30 mg/mL to about 70 mg/mL or about 5 mg/mL to about 50 mg/mL. In certain embodiments, the at least one additional excipient comprises or is carbomer. In specific embodiments, carbomer is present in the composition in an amount of about 2 mg/mL to about 250 mg/mL, or about 5 mg/mL to about 100 mg/mL. In some embodiments, the at least one additional excipient comprises or is HEC. In specific embodiments, HEC is present in the composition in an amount of about 1 mg/mL to about 100 mg/mL, about 30 mg/mL to about 70 mg/mL or about 5 mg/mL to about 50 mg/mL. In some embodiments, the at least one additional excipient comprises or is a combination of CMC and MCC (e.g., Avicel® RC-591). In specific embodiments, the CMC/MCC combination (e.g., Avicel® RC-591) is present in the composition in an amount of about 1 mg/mL to about 150 mg/mL, 1 mg/mL to about 75 mg/mL, or about 5 mg/mL to about 40 mg/mL. In certain embodiments, the CMC/MCC mixed weight ratio is between about 1/99 and about 99/1, about 20/80 and about 5/95, or about 15/85 and about 10/90. In a specific embodiment, the CMC is NaCMC and the CMC/MCC mixed weight ratio is about 11/89.

In certain embodiments, dextrose is present in the composition in an amount of about 10 mg/mL to about 1 g/mL. In some embodiments, maltodextrin is present in the composition in an amount of about 10 mg/mL to about 1.5 g/mL. In certain embodiments, edetate is present in a composition in an amount of about, 0.02 mg/mL to about 5 mg/mL, about 0.02 mg/mL to about 2 mg/mL, or about 0.05 mg/mL to about 2 mg/mL. In some embodiments, citrate is present in the composition in an amount of about 0.1 mg/mL to about 50 mg/mL, or about 0.2 mg/mL to about 30 mg/mL. In certain embodiments, polysorbate 80 is present in the composition in an amount of about 0.01 mg/mL to about 10 mg/mL, about 0.05 mg/mL to about 1 mg/mL, or about 0.05 to about 0.5 mg/mL.

In certain embodiments, amounts of component per mL refers to the amount of component in relation to the amount of total (or q.s.) volume of the composition as a whole, rather than the volume of any liquid component, such as water, alone. In specific embodiments, provided herein are compositions comprising the ingredients in about the amounts as set forth in any one of Examples 1-22, e.g., Example 19, Example 20, Example 21, or Example 22.

In certain embodiments, the compositions described herein further comprise excipients and/or auxiliaries suitable for enabling the compositions to be formulated tablets, pills, dragees, capsules, liquids, soft chews, creams, pastes, chewable tablets, gels or gel matrices, syrups, slurries, suspensions, gums, lozenges, and the like, for oral ingestion by a patient to be treated. In certain instances, oral formulations (e.g., suspensions, creams or gel matrices) are formulated such that upon oral administration, an interface layer between the oral formulation (e.g., suspension, cream or gel matrix) and a surface of the gastrointestinal tract (e.g., a mucosa or epithelium of the gastrointestinal tract) is formed. In some instances, an oral formulation (e.g., a suspension, cream or gel matrix) in contact with a surface of the gastrointestinal tract delivers a corticosteroid to the site of the gastrointestinal tract contacted with the formulation via the interface layer and as the oral formulations (e.g., suspensions, creams or gel matrices) near the interface layer is depleted of corticosteroid, a concentration gradient results. In certain instances, portions of the oral formulations (e.g., suspensions, creams or gel matrices) with high concentrations of corticosteroid relative to the portions of the oral formulations (e.g., suspensions, creams or gel matrices) proximate to the interface layer replenishes corticosteroid in the portion of the oral formulations (e.g., suspensions, creams or gel matrices) proximate to the interface layer. In certain instances, upon oral administration of an oral formulation described herein to an individual, an interface layer is formed between a mucosal membrane and a mixture of the oral formulation (e.g., chewable tablet) and saliva of the individual.

In certain embodiments, the pharmaceutical compositions described herein optionally comprise water. In certain embodiments, the pharmaceutical compositions described herein comprise water as a vehicle. In some embodiments, the vehicle is a combination of water and alcohol. In other embodiments, the vehicle is a non-aqueous liquid vehicle.

In some embodiments, a pharmaceutical composition or dosage form described herein is a suspension comprising a corticosteroid (e.g., budesonide). In some embodiments, compositions (e.g., suspensions) comprise a certain concentration of corticosteroid (e.g., budesonide) that is dissolved in the liquid medium (e.g., the solvent or liquid vehicle used, such as water, alcohol, aqueous alcohol, or the like). In certain embodiments, the amount of corticosteroid (e.g., budesonide) dissolved in the liquid medium (e.g., in an equilibrated sample) is greater than 4 µg/mL, greater than 5 µg/mL, greater than 10 µg/mL, greater than 15 µg/mL, greater than 20 µg/mL, greater than 21 µg/mL, greater than 22 µg/mL, greater than 23 µg/mL, greater than 24 µg/mL, greater than 25 µg/mL, about 25 µg/mL greater than 30 µg/mL about 25 µg/mL to about 80 µg/mL, about 30 µg/mL to about 80 µg/mL, about 30 µg/mL, about 35 µg/mL, about 40 µg/mL, about 45 µg/mL, about 50 µg/mL, about 55 µg/mL, about 60 µg/mL, about 65 µg/mL, or about 70 µg/mL. In some embodiments, the corticosteroid (e.g., budesonide) is present in the composition in combination with maltodextrin. In more specific embodiments, the maltodextrin has a DE of about 4-7, or about 13-17. In some embodiments, an acyclic oligosaccharide (e.g., maltodextrin) provided in a composition described herein is used as a solubility enhancing agent of the corticosteroid (e.g., budesonide). As used herein, an "acyclic oligosaccharide" refers to an oligosaccharide or polysaccharide that does not form a macrocycle (e.g., a starch conversion product such as maltodextrin or an aqueous soluble corn syrup, or a glycan, such as hyaluronic acid); individual saccharide monomeric units of the oligosaccharide may be cyclic. In some embodiments, compositions described herein comprise a corticosteroid (e.g., budesonide), a carboxymethyl cellulose and/or microcrystalline cellulose (e.g., Avicel® RC-591), and a liquid medium (e.g., water). In specific embodiments, compositions described herein comprise a corticosteroid (e.g., budesonide), a carboxymethyl cellulose and/or microcrystalline cellulose (e.g., Avicel® RC-591), maltodextrin, and a liquid medium (e.g., water). In more specific embodiments, the composition comprises greater than 4 µg/mL, greater than 5 µg/mL, greater than 10 µg/mL, greater than 15 µg/mL, greater than 20 µg/mL, or the like of budesonide dissolved in the liquid medium (e.g., water).

In certain embodiments, a solubility inhibitor is optionally utilized in a formulation herein in order to inhibit solvation or dissolution of corticosteroid. In some instances, inhibition of the solvation or dissolution of the corticosteroid allows the corticosteroid to retain chemical stability in the composition for an extended period of time (compared to a similar composition having a greater concentration of dissolved corticosteroid). In some embodiments, solubility inhibitors include, by way of non-limiting example, disaccharides and monosaccharides (e.g., dextrose). In certain embodiments, wherein an excipient that increases the interaction of the composition or corticosteroid with a surface of the gastrointestinal tract also increases solubility of corticosteroid in the vehicle of the composition (e.g., an aqueous medium), a solubility inhibitor is utilized to reduce or inhibit dissolution or solvation of the corticosteroid (e.g., such solvation or dissolution that is aided by the use of the excipient that increases the interaction of the composition or corticosteroid with the surface of the gastrointestinal tract).

In some embodiments, compositions (e.g., suspensions) comprise a certain concentration of budesonide that is dissolved in the liquid medium (e.g., the solvent or liquid vehicle used, such as water, alcohol, aqueous alcohol, or the like). In specific embodiments, the amount of R epimer of the dissolved budesonide (compared to the overall weight of the budesonide) is greater than 28% w/w, greater than 30% w/w, greater than 39% w/w, greater than 40%, about 39-50%, about 40-50%, less than 38% w/w, about 29%-37% w/w, less than 27% w/w, or the like. In some instances, the % epimers are obtained in a composition having an overall % R epimer (compared to overall budesonide) of about 50-55% w/w, or about 53-54% w/w. In some embodiments, maltodextrin (e.g., maltodextrin comprising a DE of about 4-7 or about 13-17) is utilized as a solubility enhancer herein. In further embodiments, maltodextrin is a solubility enhancing agent that selectively enhances the solubility of the R epimer over the S epimer (e.g., enhances the solubility of the R epimer to a greater extent than the S epimer) of budesonide. In other embodiments, maltodextrin is a solubility enhancing agent that selectively enhances the solubility of the S epimer over the R epimer (e.g., enhances the solubility of the R epimer to a greater extent than the S epimer) of budesonide. In certain instances, the R epimer of budesonide is less stable than the S epimer. In certain embodiments, compositions described herein are formulated to adjust the amount of R and/or S epimer of budesonide dissolved in the aqueous medium so as to increase or maximize stability (e.g., chemical stability) of the composition. In some instances, the concentration of corticosteroid is the concentration measured of an equilibrated sample. In certain instances, equilibration of the sample is accomplished once the concentration of the corticosteroid (e.g., budesonide) dissolved in the liquid is substantially stable, e.g., after 2 days, 3 days, 4 days, 5 days, a week, a month, or the like. In specific instances, equilibration of the sample is accomplished after 2 days.

In certain embodiments, the compositions provided herein are prepared utilizing any suitable source of active agents. In some embodiments, corticosteroid (e.g., budesonide) used in the compositions described herein are neat corticosteroid (e.g., budesonide). In some embodiments, the neat corticosteroid (e.g., budesonide) is neat, bulk corticosteroid. In certain embodiments, the neat corticosteroid (e.g., budesonide) is powder corticosteroid (e.g., budesonide). In specific embodiments, the neat corticosteroid (e.g., budesonide) is micronized corticosteroid (e.g., budesonide).

In some embodiments, the corticosteroid is administered in a commercially available formulation. In other embodiments, the corticosteroid is administered in a composition comprising a commercially available formulation of a corticosteroid and formulated as described herein. For example, in some embodiments, the corticosteroid containing composition provided herein comprises a commercially available formulation and an excipient, such as a diluents, a flavoring agent, a mucoadhesive agent, a viscosity enhancing agent, a binder, a filler, a lubricant, a solvent, a suspension agent, a coloring agent, a sweetener, a preservative, an antioxidant, a buffering agent, a humectant, a chelating agent, a surfactant, combinations thereof, or the like. In some embodiments, wherein the corticosteroid is budesonide, the commercially available formulation is Pulmicort Respules® (distributed by AstraZeneca, e.g., as set forth in NDA 20-929, which is hereby incorporated by reference in its entirety). In other embodiments, wherein the corticosteroid is budesonide, the commercially available formulation is Rhinocort Aqua® (distributed by AstraZeneca LP, Wilmington, Del. 19850, e.g., as set forth in NDA 20-746, which is, including all supplements, hereby incorporated herein by reference in its entirety). In still other embodiments, wherein the corticosteroid is budesonide, the commercially available formulation is Symbicort® (manufactured by AstraZeneca Dunkerque Production, Dunkerque, France, e.g., as set forth in NDA 21-929, which is, including all supplements, hereby incorporated herein by reference in its entirety). In some embodiments, wherein the corticosteroid is fluticasone, the commercially available formulation is Flonase®. In some embodiments, the ratio of commercially available formulation to the optional diluent is between about 1:0.5 and about 1:100. Diluents include any pharmaceutically acceptable oral diluent including, e.g., powder diluents (such as talc) and liquid diluents (such as water, ethanol and combinations thereof). In certain embodiments, the commercially available formulation is Entocort® (manufactured by Astra-Zeneca AB, S-151 85 Sodertalje, Sweden, distributed by Prometheus Laboratories Inc, San Diego, Calif. 92121, as set forth in NDA 21-324, which is, including all supplements, hereby incorporated herein by reference in its entirety). In certain embodiments, Entocort® formulations are dissolved and/or dispersed in an aqueous vehicle. In specific embodiments, the Entocort® formulation is dispersed in a liquid vehicle that has a pH sufficient to remove the enteric coating from the budesonide particles. In other embodiments, the Entocort® formulation is pre-treated with a solvent having a pH sufficient to remove the enteric coating from the budesonide particles therein, and the particles are subsequently formulated into a composition described herein.

In certain embodiments, a corticosteroid composition described herein comprises a corticosteroid, a commercially available formulation, and, optionally, one or more additional excipient. In some embodiments, a corticosteroid composition described herein comprises a corticosteroid formulated in a manner similar to a commercial formulation (e.g., lacking one or more of the active ingredients of the formulation), and, optionally, one or more additional excipient. The one or more additional excipients can be utilized to achieve a formulation as described herein. In specific embodiments, the commercially available formulation is Ultra XCID (manufactured by Matrixx Initiatives, Inc., Phoenix, Ariz.).

Diseases

In some embodiments, provided herein are methods of treating, preventing, or alleviating inflammation or symptoms associated with inflammation of the gastrointestinal tract, e.g., the esophagus. In specific embodiments, the method provided herein is a method of reducing or alleviating symptoms of inflammation of the gastrointestinal tract. In more specific embodiments, the inflammation of the gastrointestinal tract is eosinophilic esophagitis (EE or EoE). In some embodiments, the method provided herein is a method of treating inflammation associated with eosinophilic esophagitis (EE or EoE). In certain embodiments, the method provided herein is a method of treating dysphagia associated with eosinophilic esophagitis (EE or EoE). In some embodiments, the method provided herein is a method of treating inflammation and dysphagia associated with eosinophilic esophagitis (EE or EoE). In certain embodiments, provided herein are methods of treating diseases or conditions of the gastrointestinal tract (e.g., a disease or condition of the upper gastrointestinal tract, including a disease or condition of the esophagus), by administering a composition described herein.

In some embodiments, administration of the composition described herein treats, prevents, or alleviates inflammation or symptoms associated with the inflammatory disease or condition. Diseases or conditions of the gastrointestinal tract include, by way of non-limiting example, any chronic inflammatory or malignant state that involves the gastrointestinal tract (e.g., the upper gastrointestinal tract, esophagus, stomach and/or digestive tract) and responds to steroid therapy. In certain instances, the diseases or conditions treated by the compositions described herein include diseases or conditions of the upper gastrointestinal tract (including pre-colonic disease and disorders), the esophagus, the stomach, and/or the digestive tract. The methods of the present invention are useful, for example, for treating, preventing and alleviating the inflammation associated with or symptoms of eosinophilic esophagitis, inflammatory bowel diseases involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., Candida, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, acute esophageal inflammation secondary to caustic/irritant ingestion, persistent/recurrent esophageal strictures secondary to caustic/irritant, conditions due to ingestion, systemic diseases, congenital diseases, post-surgery inflammation, and gastro enteritis. The methods of the present invention are also useful, for example, for treating, preventing and alleviating inflammation associated with or symptoms of gastroesophageal reflux disease (GERD), nonerosive reflux disease (NERD), Barrett's Esophagus, and/or erosive esophagitis.

It will be appreciated that reference herein to treatment extends to prophylaxis as well as the treatment of inflammation or other symptoms.

In certain embodiments, provided herein is a method of treating, preventing or alleviating inflammation of the gastrointestinal tract, including, by way of non-limiting example, the esophagus, stomach and/or digestive tract, in an individual comprising orally administering to said individual any of the compositions described herein. In certain embodiments, the oral dosage form comprises a liquid vehicle and is formulated as, e.g., a slurry, suspension, syrup, dispersion, solution, etc.

In one aspect, a patient is administered a corticosteroid such as, for example, budesonide or fluticasone propionate.

In some embodiments, the inflammation treated by the methods and compositions described herein is associated with eosinophilic inflammation and/or neutrophilic inflammation. In some embodiments, individuals (e.g., patients) to be treated with compositions described herein include those that have been diagnosed with eosinophilic esophagitis, an inflammatory bowel disease involving the esophagus, Crohn's disease, celiac disease, proximal gastrointestinal pathology (e.g., in individuals suffering from hypofunctioning gallbladder), eosinophilic gastrointestinal inflammation, celiac disease, eosinophilic duodenitis, duodenal eosinophilia, functional dyspepsia, intermediate esophagitis, epithelial hyperplasia, basal cell hyperplasia, elongated papillae, dilated vessels in papillae, fungal esophagitis (e.g., Candida, turolopsis, histoplasma *Aspergillus*, etc.), viral esophagitis (e.g., HSV, CMV, V2V), bacterial esophagitis (e.g., tuberculosis, actinomycosis, syphilis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, or gastro enteritis. In one non-limiting example, the patient has eosinophilic esophagitis. In some embodiments, individuals (e.g., patients) to be treated with the compositions described herein include those that have been diagnosed with gastroesophageal reflux disease (GERD), nonerosive reflux disease (NERD), Barrett's Esophagus, and/or erosive esophagitis. In some embodiments, the patient is an adult. In other embodiments, the patient is a child or infant. In various aspects, a patient is a child or infant less than 16 years old, less than 12 years old, less than 8 years old, less than 6 years old, less than 4 years old or less than 2 years old.

In some embodiments, a composition is in a unit dose formulation for oral administration of a patient. In some embodiments, a unit dose of the corticosteroid is administered from a metered dose device. In some embodiments, the metered dose device delivers a metered unit dose of a composition described herein to the mouth or throat of an individual in need thereof. In certain embodiments, the metered dose device is a metered inhaler, which is utilized to administer a metered unit dose to the mouth or throat of an individual (the individual swallows rather than inhales the metered unit dose). In certain embodiments, a metered dose device dispenses a metered unit dose of a composition described herein into a receptacle (e.g., a cup), which is then utilized to orally administer the metered unit dose to the mouth or throat.

In some embodiments, provided herein is a multiple unit container comprising about 2 to about 180, about 10 to about 60, about 14, or about 30 unit doses of any pharmaceutical composition described herein. In more specific embodiments, each dose comprises about 1 mL to about 25 mL, about 1 mL to about 20 mL, about 7 mL to about 25 mL, about 10 to about 20 mL, about 15 mL, about 20 mL, about 3 to about 7 mL, about 5 mL, about 8 mL to about 12 mL, or about 10 mL. In still more specific embodiments, each dose comprises about 0.1 to about 20 mg, about 0.1 to about 10 mg, about 0.1 to about 7.5 mg, about 0.1 to about 5 mg, about 0.3 to about 4 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg of corticosteroid. In certain embodiments, provided herein is a multiple unit container comprising about 10 mL to about 1500 mL, about 50 mL to about 600 mL, about 150 mL, about 300 mL, about 600 mL, or about 1,200 mL of any pharmaceutical composition described herein. In specific embodiments, the multidose container comprises about 330 mL or about 55 mL of a composition described herein. In some embodiments, a kit provided herein comprises any multidose container as described herein, a pharmaceutical composition as described herein (e.g., in a volume described), and a delivery or metered device (e.g., a syringe, a cup, a spoon, or the like). In specific embodiments, the delivery device is incorporated into the container (e.g., an nebulizer, a aerosolizer, a pump, or the like). In certain embodiments, the pharmaceutical composition contained within any of the multiple unit containers described herein is physically and chemically stable.

In certain aspects, about 0.1 mg to about 20 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.3 mg to about 4 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) corticosteroid per day is administered to a patient. In some embodiments, the corticosteroid is present in a unit dose in an amount of between about 0.25 mg and about 5 mg. In some embodiments, the amount of corticosteroid administered daily or in a unit dose is between about 0.1 mg and about 20 mg. In some embodiments, the amount of corticosteroid administered daily or in a unit dose is between about 0.3 mg and about 4 mg. In certain embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, or between about 2 and about 3 mg.

In some embodiments, the dose or volume of a composition administered herein is adjusted based on the efficacy of treatment. In certain embodiments, a diagnosis of eosinophilic esophagitis (EE or EoE) is achieved by administering a composition described herein and determining the efficacy of the treatment. In certain embodiments, a composition described herein and separately determined to be effective in treating eosinophilic esophagitis (EE or EoE) is utilized. Efficacy of treatment can be determined in any suitable manner including, e.g., symptom score assessment, gastrointestinoscopy (e.g., esophagogastroduodenoscopy), gastrointestinal (e.g., esophageal) biopsy, histological evaluation, or a combination thereof. Processes of diagnosing eosinophilic esophagitis (EE or EoE) and/or determining efficacy of treatment include any suitable process including, by way of non-limiting example, processes as set forth in Aceves et al, J Allergy Clin Immunol, February 2008; abstract 270, or Aceves et al., Am J Gastroenterol., October 2007, 102(10):2271-9, both of which are incorporated herein in their entirety.

In some embodiments, a process for determining efficacy of a treatment (e.g., for eosinophilic esophagitis) described herein is a clinical symptom score assessment comprising (i) administering a composition described herein to an individual diagnosed with or suspected of having eosinophilic esophagitis; and (ii) evaluating one or more symptom of the individual. In certain embodiments, prior to administering the composition, the process comprises evaluating the one or more symptom of the individual. Symptoms that are optionally scored include, by way of non-limiting example, nausea, vomiting, pain, and heartburn. Total score or change in score is optionally utilized to diagnose a disorder and/or determine efficacy of treatment.

In certain embodiments, a process for determining efficacy of a treatment described herein comprises (i) administering a composition described herein to an individual diagnosed with or suspected of suffering from inflammation of the gastrointestinal tract (e.g., eosinophilic esophagitis); (ii) endoscoping the gastrointestinal surface of the individual; (iii) biopsying the gastrointestinal surface tissue; and (iv) evaluating the biopsied tissue and optionally determining an endoscopy score of the tissues biopsied. In specific embodiments, the process further comprises comparing the evaluated biopsied tissue and/or the endoscopy score obtained prior to administration of the composition to the biopsied tissue and/or endoscopy score subsequent to administration of the composition.

In some embodiments, provided herein is a process of diagnosing an individual with gastrointestinal inflammation by (i) detecting and/or measuring symptoms of the individual prior to administering to the individual a composition described herein; (ii) administering to the individual any composition described herein; (iii) detecting and/or measuring symptoms of the individual following administration of the composition; and (iv) comparing the symptoms measured or detected prior to and following administration of a composition described herein. If the symptoms exhibited by the individual are reduced (e.g., by a statistically significant or clinically relevant amount), a positive diagnosis occurs. In specific embodiments, the process of diagnosing an individual with gastrointestinal inflammation is diagnosing an individual with eosinophilic esophagitis.

Combinations

As discussed herein, compositions and formulations described comprise at least one corticosteroid (e.g., budesonide or fluticasone propionate). In some embodiments, a composition or formulation described herein further comprises at least one additional active agent. In specific embodiments, a composition or formulation described herein comprises a therapeutically effective amount of a corticosteroid and a therapeutically effective amount of at least one additional active agent. In some embodiments, the at least one additional active agent is an agent that treats, prevents, or alleviates the symptoms of and/or inflammation associated with inflammatory diseases involving the gastrointestinal tract (e.g., esophagus). It is to be understood that in certain instances, when the corticosteroid is combined with an additional active agent, the therapeutically effective amount of the corticosteroid is less than it when the additional active agent is absent.

Furthermore, provided herein are methods of preventing or alleviating gastrointestinal (e.g., esophageal) inflammation in an individual comprising orally administering to the individual a corticosteroid in association or combination with at least one additional active agent. In certain embodiments, the corticosteroid and the at least one additional active agent is in a single dosage form. In other embodiments, the corticosteroid and the at least one additional active agent are in separate dosage forms and are administered in any manner, including, by way of non-limiting example, simultaneously, sequentially, or at different times. For example, in certain embodiments, several doses of a corticosteroid composition are administered over a period of time, after which administration of the corticosteroid composition is discontinued and administration of at least one additional active agent is administered at least once.

In some embodiments, the at least one additional active agent utilized in a composition, formulation or method described herein is an agent that treats, prevents, or alleviates the symptoms of and/or inflammation associated with inflammatory diseases involving the gastrointestinal tract (e.g., esophagus). In more specific embodiments, the at least one additional active agent is not a second corticosteroid. In certain embodiments, the at least one additional active agent is an acid inhibitor (e.g., an H2 antagonist and/or a PPI). In certain embodiments, the at least one additional active agent is, by way of non-limiting example, a proton pump inhibitor (PPI), a histamine (e.g., H1, H2, and/or H3) receptor ligand (e.g., antagonist), a transient lower esophageal sphincter relaxation (TLESR)-reducing agent, a prokinetic serotonergic agent, a potassium-competitive acid blocker (P-CAB), a mucosal protectant, an anti-gastrin agent, a leukotriene antagonist, a mast cell inhibitor, a mast cell stabilizer, an immunomodulator, a biologic, an anti-asthmatic agent, a non-steroidal anti-inflammatory drug (NSAID), a chemotherapeutic, mGluR$_5$ antagonists, acetylcholine modulator, $5HT_4$ receptor agonist, $5HT_3$ receptor antagonist, $5HT_1$ receptor antagonist, antibiotics, or a combination thereof. In certain embodiments, the at least one additional active agent is an antacid (e.g., calcium carbonate and/or magnesium hydroxide).

PPIs useful herein include, by way of non-limiting example, omeprazole, hydroxyomeprazole, esomeprazole, tenatoprazole, lansoprazole, pantoprazole, rabeprazole, dontoprazole, habeprazole, perprazole, ransoprazole, pariprazole, leminoprazole, S-tenatoprazole-Na, and dexlansoprazole.

In some embodiments, the at least one additional active agent is an H2 receptor ligand (e.g., H2 receptor antagonist). In certain embodiments, H2 receptor antagonists useful herein include, by way of non-limiting example, cimetidine, ranitidine, famotidine and nizatidine. In some embodiments, the therapeutic agent is a H3 receptor ligand (e.g., agonist or antagonist). In certain embodiments, suitable H3 receptor agonists include, by way of non-limiting example, (R)-α-methyl-histamine. In some embodiments, the therapeutic agent is a H1 receptor ligand (e.g., antagonist).

In certain embodiments, the at least one additional active agent is a TLESR-reducing agent. Suitable TLESR-reducing agents include, by way of non-limiting example, GABAB agonists (e.g., baclofen), cholecystokinin (CCK-A or CCK-1) antagonists, anticholinergic agents, NO synthase inhibitors, and combinations thereof.

In some embodiments, the at least one additional active agent is a prokinetic serotonergic agent. In certain embodiments, suitable prokinetic serotonergic agents include, by way of non-limiting example, 5-HT$_4$ receptor agonists (e.g., selective 5-HT$_4$ receptor agonists). 5-HT$_4$ receptor agonists include, by way of non-limiting example, cisapride, mosapride, tegaserod, and ATI-7505.

In some embodiments, the at least one additional active agent is a potassium competitive acid blocker (P-CAB). In certain embodiments, suitable P-CAB include, by way of non-limiting example, soraprazan (BY359), revaprazan (YH1885), AZD0865, CS-526 and combinations thereof.

In certain embodiments, the at least one additional active agent is a mucosal protectant. In some embodiments, suitable mucosal protectants include, by way of non-limiting example, sucralfate. In some embodiments, mucosal protectants include one or more of prostaglandin E$_2$ (PGE$_2$), epidermal growth factor (EGF) and/or transforming growth factor-α (TGF-α), or analogs thereof. In a specific embodiment, the mucosal protectant comprises the PGE$_2$ analog trimoprostil.

In certain embodiments, the at least one additional active agent is an anti-gastrin agent. In some embodiments, suitable anti-gastrin agents include, by way of non-limiting example, cholecystokinin (CCK-B or CCK-2) antagonists. Cholecystokinin (CCK-B or CCK-2) antagonists include, by way of non-limiting example, Z-360.

In some embodiments, the therapeutic agent is a wound healing agent, an agent that promotes cell survival, an agent that promotes cell proliferation, an antifungal agent, an antibacterial agent, an antibiotic, or a combination thereof.

In further embodiments, the at least one additional active agent is a promotility agent. In some embodiments, promotility agents include, by way of non-limiting embodiments, metoclopramide, cisapride, bethanechol, or the like.

In some embodiments, the at least one additional active agent is a chemotherapeutic agent. In some embodiments, chemotherapeutic agents include, by way of non-limiting example, 5-fluorouracil, cisplatin, docetaxel, irinotecan, mitomycin, paclitaxel, vindesine, vinorelbine, and the like.

In certain embodiments, the at least one additional active agent is a mast cell inhibitor. In some embodiments, suitable mast cell inhibitors include, by way of non-limiting example, cromolyn, cromolyn sodium, nedocromil, and the like. In certain embodiments, the therapeutic agent is a leukotriene antagonist. In some embodiments, suitable leukotriene antagonists include, by way of non-limiting example, montelukast, zafirlukast, zileuton, and the like. In some embodiments, mast cell inhibitors described herein (e.g., montelukast) are present in a composition or dose of a composition described herein in an amount sufficient to provide to an individual about 0.1 to about 20 mg/day, about 0.3 to about 4 mg/day, about 10 mg/day to about 500 mg/day, about 20 mg/day to about 40 mg/day, about 20 mg/day to about 100 mg/day, or any other therapeutically effective amount.

In some embodiments, the at least one additional active agent is a non-steroidal anti-inflammatory drug (NSAID). In specific embodiments, the NSAID is ketoprofen. In various other embodiments, the therapeutic agent is an anti-inflammatory agent, e.g., one as set forth in WO 2008/070129, which reference is hereby incorporated by reference in its entirety.

In some embodiments, the at least one additional active agent is an immunomodulator or immunosuppressant. In specific embodiments, the immunomodulator is 6-mercaptopurine (6 MP), azathioprine, suplatast tosylate, mycophenolate mofetil, lactobacillus, calcineurin inhibitors (e.g., tacrolimus, cyclosporine, or the like), or the like.

In certain embodiments, the at least one additional active agent is a biologic. In specific embodiments, the biologic is an anti IL5, an anti TNF (e.g., TNF-α), an IFN (e.g., IFN-α), an anti-eotaxin-1 antibody, an anti IL-3, an anti IgE, omalizumab, reslizumab, mepolizumab, daclizumab, SCH55700, or the like.

In some embodiments, chemotherapeutic agents include, by way of non-limiting example, imatinib, imatinib mesylate, dasatinib, AMN107, cladribine, or the like.

In some embodiments, the at least one additional active agent is an antispasmodic, an agent for treating chest pain (e.g., nitrates, nitroglycerine, or the like), a drug normally administered sublingually (e.g., vitamins, minerals, or the like), mepoliz, esomepraz, STI571, imatinib, an anti-CD25 (e.g., daclizumab), tyrosine kinase inhibitors, somatostatin, somatostatin analogs, an anti-CCR-3, an anti-TIM-3, ketotifen, a platelet derived growth factor receptor (PDGFR) inhibitor, or the like.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these publications or documents.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies which are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

While certain embodiments have been shown and described herein, it will be apparent to those skilled in the art that such embodiments are provided by way of example only. Numerous variations, changes, and substitutions will now occur to those skilled in the art and are considered to be within the scope of the disclosure herein. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Budesonide Formulation

An exemplary composition described herein is prepared by combining the following:

| Ingredient | Amount |
| --- | --- |
| Budesonide | 7.5 mg to 100 mg |
| Avicel (RC-591) | 0.5 g to 4 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 2

Budesonide Formulation

An exemplary composition described herein is prepared by combining the following:

| Ingredient | Amount |
| --- | --- |
| Budesonide | 7.5 mg to 100 mg |
| CMC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 3

Budesonide Formulation

An exemplary composition described herein is prepared by combining the following:

| Ingredient | Amount |
| --- | --- |
| Budesonide | 7.5 mg to 100 mg |
| Carbomer | 0.5 g to 10 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 4

Budesonide Formulation

An exemplary composition described herein is prepared by combining the following:

| Ingredient | Amount |
| --- | --- |
| Budesonide | 7.5 mg to 100 mg |
| HPMC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 5

Budesonide Formulation

An exemplary composition described herein is prepared by combining the following:

| Ingredient | Amount |
| --- | --- |
| Budesonide | 7.5 mg to 100 mg |
| MCC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 ml to about 10 mL (e.g., about 5 mL) and administered orally to an individual to treat, prevent or alleviate inflammation or symptoms of inflammation of the gastrointestinal tract (e.g., the esophagus).

Example 6

Budesonide Formulation

An exemplary composition described herein is prepared by combining the following:

| Ingredient | Amount |
| --- | --- |
| Budesonide | 7.5 mg to 100 mg |
| Dextrose | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 7

Budesonide Formulation

An exemplary composition described herein is prepared by combining the following:

| Ingredient | Amount |
| --- | --- |
| Budesonide | 7.5 mg to 100 mg |
| Maltodextrin | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 8

Budesonide Formulation

An exemplary composition described herein is prepared by combining the following:

| Ingredient | Amount |
| --- | --- |
| Budesonide | 7.5 mg to 100 mg |
| Dextrose | 1 g to 100 g |
| Maltodextrin | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 9

Budesonide Formulation

An exemplary composition described herein is prepared by combining the following:

| Ingredient | Amount |
| --- | --- |
| Budesonide | 7.5 mg to 100 mg |
| HEC | 0.5 g to 5 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 10

Fluticasone Propionate Formulation

An exemplary composition described herein is prepared by combining the following:

| Ingredient | Amount |
| --- | --- |
| Fluticasone Propionate | 1 mg to 100 mg |
| Avicel (RC-591) | 0.5 g to 4 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 11

Fluticasone Propionate Formulation

An exemplary composition described herein is prepared by combining the following:

| Ingredient | Amount |
| --- | --- |
| Fluticasone Propionate | 1 mg to 100 mg |
| CMC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 12

Fluticasone Propionate Formulation

An exemplary composition described herein is prepared by combining the following:

| Ingredient | Amount |
| --- | --- |
| Fluticasone Propionate | 1 mg to 100 mg |
| Carbomer | 0.5 g to 10 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 13

Fluticasone Propionate Formulation

An exemplary composition described herein is prepared by combining the following:

| Ingredient | Amount |
| --- | --- |
| Fluticasone Propionate | 1 mg to 100 mg |
| HPMC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 14

Fluticasone Propionate Formulation

An exemplary composition described herein is prepared by combining the following:

| Ingredient | Amount |
| --- | --- |
| Fluticasone Propionate | 1 mg to 100 mg |
| MCC | 0.5 g to 3 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 15

Fluticasone Propionate Formulation

An exemplary composition described herein is prepared by combining the following:

| Ingredient | Amount |
| --- | --- |
| Fluticasone Propionate | 1 mg to 100 mg |
| Maltodextrin | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 16

Fluticasone Propionate Formulation

An exemplary composition described herein is prepared by combining the following:

| Ingredient | Amount |
| --- | --- |
| Fluticasone Propionate | 1 mg to 100 mg |
| Dextrose | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 17

Fluticasone Propionate Formulation

An exemplary composition described herein is prepared by combining the following:

| Ingredient | Amount |
| --- | --- |
| Fluticasone Propionate | 1 mg to 100 mg |
| Dextrose | 1 g to 100 g |
| Maltodextrin | 1 g to 100 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 18

Fluticasone Propionate Formulation

An exemplary composition described herein is prepared by combining the following:

| Ingredient | Amount |
| --- | --- |
| Fluticasone Propionate | 1 mg to 100 mg |
| HEC | 0.5 g to 5 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 18

Fluticasone Propionate Formulation

An exemplary composition described herein is prepared by combining the following:

| Ingredient | Amount |
| --- | --- |
| Fluticasone Propionate | 1 mg to 100 mg |
| HEC | 0.5 g to 5 g |
| Disodium Edetate | 5 mg to 200 mg |
| Citric Acid | 10 mg to 1 g |
| Sodium Citrate | 10 mg to 2 g |
| Tween 80 | 5 mg to 100 mg |
| Flavoring Agent | optional |
| Sweetener | optional |
| Preservative | optional |
| Water | q.s. to 100 mL |

The composition is divided into a unit dose of about 1 mL to about 10 mL (e.g., about 5 mL) and administered orally to an individual to treat, prevent or alleviate inflammation or symptoms of inflammation of the gastrointestinal tract (e.g., the esophagus).

Example 19

Budesonide Formulation

An exemplary composition described herein is prepared by combining the following:

| Ingredient | Amount |
| --- | --- |
| Budesonide | 1 mg |
| Avicel | 100 mg |
| Dextrose | 0.5 g |
| Maltodextrin (M150) | 1.3 g |
| EDTA | 2.5 mg |
| Tween 80 | 0.5 mg |
| Cherry Flavor | 25 mg |
| Glycerin | 250 mg |
| AceK | 37.5 mg |
| Magnasweet | 25 mg |
| Sodium Benzoate | 10 mg |
| Potassium Sorbate | 10 mg |
| Aqueous Citric Acid Buffer | q.s. to 5 mL |

The composition is administered orally to an individual to treat, prevent or alleviate inflammation or symptoms of inflammation of the gastrointestinal tract (e.g., the esophagus).

Example 20

Budesonide Formulation

An exemplary composition described herein is prepared by combining the following:

| Ingredient | Amount |
| --- | --- |
| Budesonide | 1 mg |
| Avicel | 200 mg |
| Dextrose | 1 g |
| Maltodextrin (M150) | 2.6 g |
| EDTA | 5 mg |
| Tween 80 | 1 mg |
| Cherry Flavor | 50 mg |
| Glycerin | 500 mg |
| AceK | 75 mg |
| Magnasweet | 50 mg |
| Sodium Benzoate | 10 mg |
| Potassium Sorbate | 10 mg |
| Aqueous Citric Acid Buffer | q.s. to 10 mL |

The composition is administered orally to an individual to treat, prevent or alleviate inflammation or symptoms of inflammation of the gastrointestinal tract (e.g., the esophagus).

Example 21

Budesonide Formulation

An exemplary composition described herein is prepared by combining the following:

| Ingredient | Amount (mg/mL) |
| --- | --- |
| Budesonide | 0.05 |
| Avicel RC-591 | 23.6 |
| Dextrose | 118 |
| Maltodextrin (M150) | 306.8 |
| Disodium edetate | 0.59 |
| Citric acid | 1.77 |
| Sodium citrate | 0.59 |
| Polysorbate 80 | 0.12 |
| Cherry Flavor | 5.9 |
| Glycerin | 59 |
| Acesulfame potassium | 5.9 |
| Magnasweet 110 | 5.9 |
| Sodium Benzoate | 2.36 |
| Potassium Sorbate | 2.36 |
| Water | q.s. to 1, 2, 3, 4, 5, 6, 7, 8, 9, 10, 11, 12, 13, 14, or 15 mL |

The composition is administered orally to an individual to treat, prevent or alleviate inflammation or symptoms of inflammation of the gastrointestinal tract (e.g., the esophagus).

Example 22

Budesonide Formulation

An exemplary composition described herein is prepared by combining the following:

| Ingredient | Amount (mg/mL) |
| --- | --- |
| Budesonide | 0.2 |
| Avicel RC-591 | 23.6 |
| Dextrose | 118 |
| Maltodextrin (M150) | 306.8 |
| Disodium edetate | 0.59 |
| Citric acid | 1.77 |
| Sodium citrate | 0.59 |
| Polysorbate 80 | 0.12 |
| Cherry Flavor | 5.9 |
| Glycerin | 59 |
| Acesulfame potassium | 5.9 |
| Magnasweet 110 | 5.9 |
| Sodium Benzoate | 2.36 |
| Potassium Sorbate | 2.36 |
| Water | q.s. to 1, 2, 3, 4, 5, 6, 7, 8, 9, 10, 11, 12, 13, 14, or 15 mL |

The composition is administered orally to an individual to treat, prevent or alleviate inflammation or symptoms of inflammation of the gastrointestinal tract (e.g., the esophagus).

Example 23

In certain instances, the formulations described in the examples set forth herein are scaled to an amount sufficient to provide any desired amount, e.g., about 150 mL or 300 mL of total composition volume, either by scaling up a composition described in the examples herein, e.g., to about 150 mL, or by scaling to a larger volume and dividing the scaled composition into smaller portions, e.g., portions comprising about 150 mL. The portions, e.g., those comprising about 150 mL or 300 mL, may then be placed into a multi dose container. A plurality of doses may then be dispensed and administered to an individual to treat, prevent or alleviate inflammation or symptoms of inflammation of the gastrointestinal tract (e.g., the esophagus).

Example 24

Budesonide solubility of certain formulations is described. To determine the solubility of budesonide in the liquid medium of a formulation, particulates of the formulation are filtered. Samples are centrifuged at 12,000 rpm and 20° C. using Whatman centrifuge filters, 0.45 µm (Nylon). Filtration time vary depending on sample, but are generally between 5 minutes and 1 hour. Prior to centrifugation, samples are equilibrated, if necessary, to achieve a substantially equilibrated concentration of budesonide. Determined is the concentration of budesonide in the liquid medium and the % (w/w) of the budesonide dissolved that is the R epimer. Formulation A is prepared by combining two Pulmicort Respules® (0.5 mg budesonide in 2 mL each) with 10 g of Splenda® (distributed by McNeil Nutritionals, LLC Fort Washington, Pa. 19034-2299; about 1 g per packet) and equilibrating for about 48 hours. Formulation B is prepared by combining two Pulmicort Respules® (0.5 mg budesonide in 2 mL each) with about 9 g of maltodextrin having a DE of about 17 and a trace amount of sucralose, and equilibrating for about 48 hours. For Formulations C—I, excess budesonide particles were combined with water, and optionally maltodextrin, and equilibrated over 5 days. Formulation C is saturated budesonide in water. Formulation D is an aqueous composition comprising 2.5% (w/w) maltodextrin (M440, DE 4-7). Formulation E is an aqueous composition comprising 5% (w/w) maltodextrin (M440, DE 4-7). Formulation F is an aqueous composition comprising 10% (w/w) maltodextrin (M440, DE 4-7). Formulation G is an aqueous composition comprising 7.5% (w/w) of maltodextrin (M150, DE 13-17). Formulation H is an aqueous composition comprising 15% (w/w) of maltodextrin (M150, DE 13-17). Formulation I is an aqueous composition comprising 30% (w/w) of maltodextrin (M150, DE 13-17). Formulation J is the aqueous composition of Example 22, comprising 26% (w/w) of maltodextrin (M150, DE 13-17). Formulation K is an aqueous composition comprising 20% w/w of dextrose, equilibrated for 48 hours. Formulation L is an aqueous composition comprising 40% w/w of dextrose, equilibrated for 48 hours. Formulation M is prepared by combining excess budesonide and GUM® Rincinol® P.R.N.™ and filtering. Results are set forth in Table 10.

TABLE 10

| | Budesonide Solubility | | |
| --- | --- | --- | --- |
| Formulation | Solubility (µg/mL) | % R epimer (w/w) | Filtration time (min) |
| A | 20 | 37 | 5 |
| B | 70 | 48 | 5 |
| C | 19 | 28 | 5 |
| D | 23 | 33 | 5 |
| E | 34 | 26 | 5 |
| F | 50 | 25 | 5 |
| G | 31 | 32 | 5 |
| H | 45 | 31 | 5 |
| I | 67 | 43 | 5 |
| J | 25 | | 5 |
| K | 16 | 24 | 5 |

TABLE 10-continued

Budesonide Solubility

| Formulation | Solubility (μg/mL) | % R epimer (w/w) | Filtration time (min) |
|---|---|---|---|
| L | 11 | 24 | 5 |
| M | 34 | 29 | 5 |
| Rhinocort Aqua ® | 4.0 | 27.9 | 30 |
| Pulmicort Respules ® | 19.0 | 27.1 | 5 |

For Formulation A, the unequilibrated concentration of budesonide was 28 μg/mL, 38.7% w/w of the dissolved budesonide being the R epimer. For Formulation B, the unequilibrated concentration of budesonide was 48 μg/mL, 45.3% w/w of the dissolved budesonide being the R epimer.

Example 25

This example details the efficacy and safety of once daily and twice daily use of budesonide formulations of Examples 21 and 22 in 5 mL, 7 mL, 10 mL, 12 mL, 15 mL, and 17.5 mL doses in inducing and maintaining remission of disease activity in children with EE. A number of children (e.g., 20 per budesonide dose frequency, amount, and volume) are evaluated to determine the highest eosinophil count (eos/hpf) and the mean highest eosinophil count for the group. Evaluation of the highest eosinophil count (eos/hpf) and the mean highest eosinophil count for the group is also determined following therapy. Symptom scores and mean symptom scores are also determined before and after therapy.

In some instances, individuals who received previous therapy with proton pump inhibitor, elimination diet based upon skin or blood allergy testing, or elimination diet or refused elimination diet, but continued to have ≥24 eos/hpf on esophageal biopsy are included in the review. Patients are defined as having food or aeroallergen sensitization if RAST and/or skin prick testing are positive. No changes are made to longstanding therapy used for treating chronic conditions such as asthma or eczema and none of the children receive concurrent immune-modulatory treatment.

Endoscopy is performed using the Olympus P160 endoscope (by RD) and pan-esophageal, gastric and duodenal biopsies are taken. Eosinophilic esophagitis (EE or EoE) is diagnosed when ≥24 eos/hpf are found in at least one of the esophageal sites biopsied. Two mucosal biopsies re taken from the proximal esophagus (3 cm below the crycopharyngeus muscle), distal esophagus (3 cm above the gastroesophageal junction (GEJ), and mid-esophagus (midpoint between the crycopharyngeus muscle and the GEJ). Biopsies are processed routinely and evaluated by a pediatric pathologist (RN). The highest number of eosinophils per ×400 high power field are counted. Basal zone hyperplasia (BZH) is reported when basal zone cells extend towards the luminal surface of the epithelium (>25% of epithelial thickness).

Follow-up endoscopy with biopsies are taken after 3-4 months treatment. Counting the highest number of eos/hpf within biopsies determined the response to therapy and patients are categorized into responders (0-7 eos/hpf), partial-responders (8-23 eos/hpf) and non-responders (≥24 eos/hpf).

An EE (EoE) Endoscopy Score is devised to compare findings before and after treatment. It is calculated from procedure reports and photographs. Four categories, (1) pallor and diminished vascular markings; (2) furrowing with "thickened" mucosa; (3) white mucosal plaques; (4) concentric rings or strictures. For each category, one point is allocated if 1 or 2 esophageal sites are involved, and two points for pan-esophageal involvement. The maximum score is 8.

Patients receive a formulation described herein for between 0.25 and 2 mg daily and are instructed not to ingest any solids or liquids for 30 minutes afterwards. No dietary changes are made in patients already on dietary restrictions.

A modified symptom score based on children with acid-peptic disease is used routinely in the EE (EoE) clinic. The symptom categories include (1) heartburn or regurgitation; (2) abdominal pain or unexplained irritability in younger children; (3) nausea or vomiting; (4) anorexia or early satiety; (5) dysphagia or odynophagia, (6) nocturnal wakening with symptoms; (7) gastrointestinal bleeding (previous 4 months). Each category scored 0-2 points with a maximum of 14 points. Zero points are awarded if the symptom is absent; one point if the symptom is mild, did not interfere with daily activities; 2 points if the symptoms are severe enough to interrupt daily activities. Previous GI bleeding is considered mild (1 point) if there is no associated hemodynamic compromise or anemia, and severe (2 points) if bleeds are multiple, caused anemia, or required blood transfusion.

All statistical analysis is carried out using NCSS Statistical Softward Package. Two-tailed p values are calculated using paired t-tests to compare the means of patient values for eos/hpf, EE (EoE) Endoscopy Scores and Symptom Scores before and after budesonide therapy. Two-tailed unpaired t-tests are utilized in order to compare variables grouped by responders versus non-responders. Spearman's correlation coefficients are generated using GraphPad Prism software. Results with p values <0.05 are considered statistically significant. Both mean and median statistics re generated, both are equivalent and mean statistics are presented.

Subjects. Chart reviews are undertaken on a number of children. All children have >24 eos/hpf on repeat esophageal biopsy before starting therapy.

Treatment. Patients received the described formation for a designated amount of time (e.g., 1 week, 2 weeks, 1 month, 2 months, 3 months, 4 months, 6 months, or the like) before repeat endoscopy. Various patients received budesonide in amounts ranging from 0.25 to 2 mg/day.

Histology. Before treatment the mean highest eosinophil count is measured for all patients, including distal, mid and proximal esophageal sites. All sites are likewise evaluated aver the designated amount of time, and again if desired.

Upper Gastrointestinal Endoscopy. Before treatment, the mean EE (EoE) Endoscopy Score for all patients is determined. Following treatment the mean EE (EoE) Endoscopy Score is repeated. Decreases in endoscopy scores (e.g., of >95%, >90%, >85%, >75%, >50%, >25%, or the like) in an individual indicate successful treatment.

Symptom Score. Before treatment the mean symptom score for all patients is determined. It is again determined following treatment. Decreases in symptom scores (e.g., of >95%, >90%, >85%, >75%, >50%, >25%, or the like) in an individual indicate successful treatment (alone or in combination with the above referenced decreases in endoscopy scores).

Adults: these parameters are repeated in adults to determine efficacy and safety therein.

REFERENCES

1. Liacouras C A, Ruchelli E. Eosinophilic esophagitis. Cuff. Opin. Pediatr. 2004; 16:560-6.
2. Kelly K J, Lazenby A J, Rowe P C, et al. Eosinophilic esophagitis attributed to gastroesophageal reflux: improvement with an amino acid-based formula. Gastroenterology 1995; 109: 1503-12.
3. Fogg M I, Ruchelli E, Spergel J M. Pollen and eosinophilic esophagitis. J. Allergy Clin. Immunol. 2003; 112:796-7.
4. Mishra A, Hogan S P, Brandt E B, Rothenberg M E. An etiological role for aeroallergens and eosinophils in experimental esophagitis. J. Clin. Invest. 2001; 107:83-90.
5. Spergel J M, Beausoleil J L, Mascarenhas M, Liacouras C A. The use of skin prick tests and patch tests to identify causative foods in eosinophilic esophagitis. J. Allergy Clin. Immunol. 2002; 109:363-8.
6. Ruchelli E, Wenmer W, Voytek T, et al. Severity of esophageal eosinophilia predicts response to conventional gastroesophageal reflux therapy. Pediatr. Dev. Pathol. 1999; 2:15-8.
7. Steiner S J, Gupta S K, Croffie J M, Fitzgerald J F. Correlation between number of eosinophils and reflux index on same day esophageal biopsy and 24 hour esophageal pH monitoring. Am. J. Gastroenterol. 2004; 99:801-5.
8. Orenstein S R, Shalaby T M, Di Lorenzo C, et al. The spectrum of pediatric eosinophilic esophagitis beyond infancy: a clinical series of 30 children. Am. J. Gastroenterol. 2000; 95:1422-30.
9. Rothenberg M E, Mishra A, Collins M H, Putnam P E. Pathogenesis and clinical features of eosinophilic esophagitis. J. Allergy Clin. Immunol. 2001; 108:891-4.
10. Ravelli A M, Villanacci V, Ruzzenenti N, et al. Dilated Intercellular Spaces: A Major Morphological Feature of Esophagitis. J. Pediatr. Gastroenterol. Nutr. 2006; 42:510-515.
11. Steiner S J, Kernek K M, Fitzgerald J F. Severity of Basal Cell Hyperplasia Differs in Reflux Versus Eosinophilic Esophagitis. J. Pediatr. Gastroenterol. Nutr. 2006; 42:506-509.
12. Mueller S, Aigner T, Neureiter D, Stolte M. Eosinophil infiltration and degranulation in oesophageal mucosa from adult patients with eosinophilic oesophagitis: a retrospective comparative study on pathologic biopsy. J. Clin. Pathol. 2006; 59:1175-80.
13. Croese J, Fairley S K, Masson J W, et al. Clinical and endoscopic features of eosinophilic esophagitis in adults. Gastrointest. Endosc. 2003; 58:516-22.
14. Aceves S, Newbury, R O, Dohil R, Schwimmer J, Bastian J. Distinguishing Eosinophilic Esophagitis in pediatric patients: clinical, endoscopic, and histologic features of an emerging disorder. Journal of Clinical Gastroenterology 2006; 41(3):252-6.
15. Straumann A, Simon H U. Eosinophilic esophagitis: escalating epidemiology? J. Allergy Clin. Immunol. 2005; 115: 418-9.
16. Cheman S, Smith N M, Forbes D A. Rapidly increasing prevalence of eosinophilic oesophagitis in Western Australia. Arch. Dis. Child 2006; 91:1000-4.
17. Sant'Anna A M, Rolland S, Fournet J C, et al. Eosinophilic Esophagitis in Children: Symptoms, Histology and pH Probe Results. J. Pediatr. Gastroenterol. Nutr. 2004; 39:373-377.
18. Potter J W, Saeian K, Staff D, et al. Eosinophilic esophagitis in adults: an emerging problem with unique esophageal features. Gastrointest. Endosc. 2004; 59:355-61.
19. Parfitt J R, Gregor J C, Suskin N G, et al. Eosinophilic esophagitis in adults: distinguishing features from gastroesophageal reflux disease: a study of 41 patients. Mod. Pathol. 2006; 19:90-6.
20. Desai T K, Stecevic V, Chang C H, et al. Association of eosinophilic inflammation with esophageal food impaction in adults. Gastrointest. Endosc. 2005; 61:795-801.
21. Straumann A, Spichtin H P, Grize L, et al. Natural history of primary eosinophilic esophagitis: a follow-up of 30 adult patients for up to 11.5 years. Gastroenterology 2003; 125:1660-9.
22. Spergel J M, Andrews T, Brown-Whitehom T F, et al. Treatment of eosinophilic esophagitis with specific food elimination diet directed by a combination of skin prick and patch tests. Ann. Allergy Asthma Immunol. 2005; 95:336-43.
23. Kagalwalla A F, Sentongo T A, Ritz S, et al. Effect of six-food elimination diet on clinical and histologic outcomes in eosinophilic esophagitis. Clin. Gastroenterol. Hepatol. 2006; 4:1097-102.
24. Markowitz J E, Spergel J M, Ruchelli E, Liacouras C A. Elemental diet is an effective treatment for eosinophilic esophagitis in children and adolescents. Am. J. Gastroenterol. 2003; 98:777-82.
25. Liacouras C A, Wermer W J, Brown K, Ruchelli E. Primary eosinophilic esophagitis in children: successful treatment with oral corticosteroids. J. Pediatr. Gastroenterol. Nutr. 1998; 26:380-5.
26. Teitelbaum J E, Fox V L, Twarog F J, et al. Eosinophilic esophagitis in children: immunopathological analysis and response to fluticasone propionate. Gastroenterology 2002; 122:1216-25.
27. Faubion W A, Jr., Perrault J, Burgart L J, et al. Treatment of eosinophilic esophagitis with inhaled corticosteroids. J. Pediatr. Gastroenterol. Nutr. 1998; 27:90-3.
28. Aceves S S, Dohil R, Newbury R O, Bastian J F. Topical viscous budesonide suspension for treatment of eosinophilic esophagitis. J. Allergy Clin. Immunol. 2005; 116: 705-6.
29. Noel R J, Putnam P E, Collins M H, et al. Clinical and immunopathologic effects of swallowed fluticasone for eosinophilic esophagitis. Clin. Gastroenterol. Hepatol. 2004; 2:568-75.
30. Remedios M, Campbell C, Jones D M, Kerlin P. Eosinophilic esophagitis in adults: clinical, endoscopic, histologic findings, and response to treatment with fluticasone propionate. Gastrointest. Endosc. 2006; 63:3-12.
31. Dohil R, Newbury R O, Sellers Z M, et al. The evaluation and treatment of gastrointestinal disease in children with cystinosis receiving cysteamine. J. Pediatr. 2003; 14:224-30.
32. Cheung K M, Oliver M R, Cameron D J, et al. Esophageal eosinophilia in children with dysphagia. J. Pediatr. Gastroenterol. Nutr. 2003; 37:498-503.
33. Fox V L, Nurko S, Furuta G T. Eosinophilic esophagitis: it's not just kid's stuff. Gastrointest. Endosc. 2002;
34. Budin C, Villard-Truc F, Rivet C, et al. [Eosinophilic esophagitis: 3 case reports]. Gastroenterol. Clin. Biol. 2005; 29:73-5.
35. Noel R J, Putnam P E, Rothenberg M E. Eosinophilic esophagitis. N. Engl. J. Med. 2004; 351:940-1.
36. Guajardo J R, Plotnick L M, Fende J M, et al. Eosinophil-associated gastrointestinal disorders: a world-wide-web based registry. J. Pediatr. 2002; 141:576-81.
37. Liacouras C A, Spergel J M, Ruchelli E, et al. Eosinophilic esophagitis: a 10-year experience in 381 children. Clin. Gastroenterol. Hepatol. 2005; 3:1198-206.

38. Liacouras C A. Eosinophilic esophagitis: treatment in 2005. Curr. Opin. Gastroenterol. 2006; 22:147-152.
39. Spergel J M. Eosinophilic esophagitis in adults and children: evidence for a food allergy component in many patients. Curr. Opin. Allergy Clin. Immunol. 2007; 7:274-8.
40. Plaza-Martin, A M, Jimenez-Feijoo R, Andaluz C, Giner-Munoz M T, Martin-Mateos M A, Piquer-Gibert M, Sierra-Martinez J I. Polysensitization to aeroallergens and food in eosinophilic esophagitis in a pediatric population. Alergol. Imnaunopathol. 2007; 35:35-7.
41. Nicolazzo, J A, Reed, B L, Finnin, B C. Buccal penetration enhancers—how do they really work? J. Controlled Release 2005; 105:1-15.
42. Furuta, G T, Liacouras, C A, Collins, M H, Sandeep, K G, Justinich, C, Putnam, P E, Bonis, P, Hassall, E, Straumann, A, Rothenberg, M E. Eosiniophilic esophagitis in children and adults: A systematic review and consensus recommendations for diagnosis and treatment. Gastroenterology 2007; 133:1342-1363.
43. Aceves, S S, Bastian J F, Newbury, R O, Dohil, R. Oral viscous budesonide: A potential new therapy for eosinophilic esophagitis. Amer. Journal of Gastroenterology 2007; 102:1-9.
44. Rothenberg M E. Eosinophilic gastrointestinal disorders. J. Allergy Clin. Immunol. 2004; 113:11-28.
45. Garrett J K, Jameson S C, Thomson B, Collins M H, Wagoner L E, Freese, D K, et al. Anti-interleukin-5 (mepolizumab) therapy for hypereosinophilic syndromes. J. Allergy Clin. Immunol. 2004; 113:115-9.

What is claimed is:

1. An oral liquid pharmaceutical composition comprising a stable dispersion or suspension comprising:
    a. budesonide in an amount of about 0.02 mg/mL to about 0.75 mg/mL of the composition,
    b. disodium edetate in an amount of about 0.05 mg/mL to about 25 mg/mL of the composition,
    c. a buffer, wherein the buffer is chosen from the group consisting of sodium citrate, citric acid, a carbonate buffer, a hydroxide buffer, a phosphate buffer, an acetate buffer, or combinations thereof,
    d. polysorbate 80 in an amount of about 0.01 mg/mL to about 1 mg/mL of the composition,
    e. a preservative, wherein the preservative is potassium sorbate present in an amount of about 0.2 mg/mL to about 10 mg/mL of the composition, sodium benzoate present in an amount of about 0.2 mg/mL to about 10 mg/mL of the composition, or a combination thereof,
    f. a flavoring agent, a sweetener, or a combination thereof,
    g. dextrose in an amount of 0-250 mg/mL of the composition,
    h. at least one additional excipient comprising maltodextrin present in an amount of about 10 mg/mL to about 1 g/mL of the composition, and one or more of hydroxyethylcellulose (HEC), hydroxypropylmethyl-cellulose (HPMC), carboxymethyl-cellulose (CMC), microcrystalline cellulose (MCC), carbomer, and combinations thereof, present in an amount of about 5 mg/mL to about 100 mg/mL of the composition; and
    i. water,
    wherein the composition is physically and chemically stable, wherein during and after storage the particles of the dispersion or suspension do not cake or aggregate, wherein the composition remains substantially uniform for at least 1 day, and wherein the composition is suitable for single or multiple dose administration, the composition having a viscosity of at least 50 cP.

2. The pharmaceutical composition of claim 1 present in a multiple-unit container and comprising a plurality of unit doses.

3. The pharmaceutical composition of claim 1, wherein the composition remains substantially uniform after storage.

4. The pharmaceutical composition of claim 1, wherein the composition regains substantial uniformity upon mild or moderate agitation, swirling, gentle swirling or shaking.

5. The pharmaceutical composition of claim 1, wherein after storage the composition regains substantial uniformity upon mild or moderate agitation, swirling, gentle swirling or shaking.

6. The pharmaceutical composition of claim 5, wherein after mild or moderate agitation, swirling, gentle swirling or shaking, the composition remains substantially uniform for a convenient period of time.

7. The pharmaceutical composition of claim 2, wherein the composition is a multiple dose formulation.

8. The pharmaceutical composition of claim 7, wherein each dose from the container of the formulation is substantially uniform with regard to each other.

9. The pharmaceutical composition of claim 7, wherein the first and final dose from the container are substantially uniform.

10. The pharmaceutical composition of claim 1, wherein the budesonide is readily dispersed throughout the composition upon mild or moderate agitation.

11. The pharmaceutical composition of claim 1, wherein the budesonide is readily dispersed throughout the composition upon mild or moderate agitation after storage.

12. The pharmaceutical composition of claim 1, wherein the budesonide is easily resuspended in the composition upon mild or moderate agitation.

13. The pharmaceutical composition of claim 1, wherein the budesonide is easily resuspended in the composition upon mild or moderate agitation after storage.

14. The pharmaceutical composition of claim 1, wherein the budesonide is readily dispersed throughout the composition upon mild or moderate agitation after storage for one week.

15. The pharmaceutical composition of claim 1, wherein the budesonide is readily dispersed throughout the composition upon mild or moderate agitation after storage for one month.

16. The pharmaceutical composition of claim 1, wherein the budesonide does not cake after storage.

17. The pharmaceutical composition of claim 1, wherein the composition is substantially free of non-budesonide particles.

18. The pharmaceutical composition of claim 1, wherein the at least one excipient does not enhance the solubility of the budesonide in the water.

19. The pharmaceutical composition of claim 1, wherein the pharmaceutical composition is a non-Newtonian fluid.

20. The pharmaceutical composition of claim 19, wherein the non-Newtonian fluid is selected from the group consisting of plastic, pseudo-plastic and dilatant.

21. The pharmaceutical composition of claim 20, wherein the non-Newtonian fluid is pseudo-plastic.

22. The pharmaceutical composition of claim 21, wherein the non-Newtonian fluid is thixotropic.

23. The pharmaceutical composition of claim 1, wherein the budesonide comprises a plurality of microparticles.

24. The pharmaceutical composition of claim 1, wherein the budesonide comprises a plurality of nanoparticles.

25. The pharmaceutical composition of claim 1, wherein the pharmaceutical composition comprises budesonide particles suspended in the composition.

26. The pharmaceutical composition of claim 25, wherein the budesonide particles are microparticles having a mean diameter of about 0.1 microns to about 50 microns.

27. The pharmaceutical composition of claim 25, wherein at least 95% of the budesonide particles are microparticles having a diameter of less than about 10 microns.

28. The pharmaceutical composition of claim 1, wherein the pharmaceutical composition has a volume of about 1 mL to about 20 mL.

29. The pharmaceutical composition of claim 28, wherein the pharmaceutical composition has a volume of about 3 mL to about 12 mL.

30. The pharmaceutical composition of claim 1, wherein the at least one additional excipient comprises CMC, and wherein the CMC is present in an amount of about 5 mg/mL to about 30 mg/mL.

31. The pharmaceutical composition of claim 1, wherein the at least one additional excipient comprises carbomer, and wherein the carbomer is present in an amount of about 5 mg/mL to about 100 mg/mL.

32. The pharmaceutical composition of claim 1, wherein the at least one additional excipient comprises HPMC, and wherein the HPMC is present in an amount of about 5 mg/mL to about 30 mg/mL.

33. The pharmaceutical composition of claim 1, wherein the at least one additional excipient comprises MCC, and wherein the MCC is present in an amount of about 5 mg/mL to about 30 mg/mL.

34. The pharmaceutical composition of claim 1, wherein the at least one additional excipient comprises a combination of CMC and MCC, wherein the CMC-MCC combination is present in an amount of about 10 mg/mL to about 40 mg/mL, and wherein the CMC/MCC mixed weight ratio is about 11/89.

35. The pharmaceutical composition of claim 1, wherein the maltodextrin has a dextrose equivalents of about 13 to about 18.

36. The pharmaceutical composition of claim 1, wherein the buffer comprises sodium citrate present in an amount of about 0.1 mg/mL to about 30 mg/mL.

37. The pharmaceutical composition of claim 1, wherein the buffer is sodium citrate present in an amount of about 0.1 mg/mL to about 30 mg/mL and citric acid present in an amount of about 0.1 mg/mL to about 10 mg/mL.

38. The pharmaceutical composition of claim 37, wherein the additional excipient is selected from hydroxyethylcellulose (HEC), hydroxypropylmethyl-cellulose (HPMC), carboxymethyl-cellulose (CMC), microcrystalline cellulose (MCC), carbomer and combinations thereof, and wherein the additional excipient is present in an amount of about 5 mg/mL to about 100 mg/mL.

39. The pharmaceutical composition of claim 1, wherein the additional excipient is maltodextrin present in an amount of about 1 mg/mL to about 1.5 g/mL.

40. The pharmaceutical composition of claim 1, wherein the pharmaceutical composition has a total volume of about 1 mL to about 20 mL.

41. A kit comprising a multiple unit container and a plurality of doses of the stable oral pharmaceutical composition of claim 1.

42. The kit of claim 41, wherein the kit comprises about 2 to about 60 doses of the pharmaceutical composition.

43. The kit of claim 41, wherein the kit comprises about 330 mL of the stable pharmaceutical composition.

44. The kit of claim 41, wherein the kit comprises about 50 ml to about 600 mL of the stable pharmaceutical composition.

45. The kit of claim 41, wherein the kit further comprises a metering device for administering the composition to an individual.

46. The kit of claim 45, wherein the metering device is incorporated into the multiple unit container.

47. The pharmaceutical composition of claim 1, wherein the maltodextrin has a dextrose equivalents of greater than 5.

48. The pharmaceutical composition of claim 1, wherein the pharmaceutical composition is chemically stable, comprising at least 90% of the initial amount of budesonide after being stored for 3 weeks.

* * * * *